United States Patent [19]
Kluger et al.

[11] Patent Number: 5,240,464
[45] Date of Patent: Aug. 31, 1993

[54] ORGANIC MATERIALS HAVING SULFONAMIDO LINKED POLY(OXYALKYLENE) MOIETIES AND THEIR PREPARATION

[75] Inventors: Edward W. Kluger, Pauline, S.C.; Max A. Weaver, Kingsport, Tenn.; Jeffery R. Harris; David J. Moody, both of Spartanburg, S.C.

[73] Assignee: Milliken Research Corporation, Spartanburg, S.C.

[21] Appl. No.: 896,508

[22] Filed: Jun. 2, 1992

Related U.S. Application Data

[63] Continuation of Ser. No. 491,419, Mar. 9, 1990, abandoned.

[51] Int. Cl.$^5$ ................................................. D06P 5/00
[52] U.S. Cl. .......................................... 8/506; 8/403; 8/497; 8/508; 8/509; 8/510; 8/512; 8/513; 8/514; 8/516; 8/519; 8/657; 8/662; 8/675
[58] Field of Search ...................................... 8/497, 506

[56] References Cited

U.S. PATENT DOCUMENTS

| | | | |
|---|---|---|---|
| 2,817,655 | 12/1957 | Schetty et al. | 534/592 X |
| 2,995,412 | 8/1961 | Kleb | 540/133 |
| 3,157,633 | 11/1964 | Kuhn | 534/887 X |
| 3,287,470 | 11/1966 | Pugin et al. | 540/143 |
| 3,380,987 | 4/1968 | Palm | 534/573 P |
| 4,640,690 | 2/1987 | Baumgartner et al. | 8/506 |
| 4,732,570 | 3/1988 | Baumgartner et al. | 8/506 |
| 4,871,371 | 10/1989 | Harris | 534/729 X |

FOREIGN PATENT DOCUMENTS

| | | | |
|---|---|---|---|
| 63-264674 | 11/1988 | Japan . | |
| 229330 | 1/1926 | United Kingdom | 534/592 |
| 1477396 | 6/1977 | United Kingdom . | |
| 1566948 | 9/1977 | United Kingdom . | |

*Primary Examiner*—A. Lionel Clingman
*Attorney, Agent, or Firm*—Timothy J. Monahan; Terry T. Moyer

[57] ABSTRACT

The process for chemically modifying metal-free, organic material for improving one or more properties thereof such as water dispersibility, compatibility with other organics, or increased chemical reactivity, wherein the process includes providing material with from 1–6 sulfonylhalide groups or sulfonate ester groups or mixtures thereof, and contacting the material under sulfonamido forming conditions with one or more reactants containing one or more poly(oxyalkylene) moieties, each of the reactants having from 1 to 4 functional amine groups, and each of the poly(oxyalkylene) moieties being comprised of from about 4 to about 200 epoxide reactant residues at least about 50 mole percent of which residues contain 2–4 carbons.

18 Claims, No Drawings

ORGANIC MATERIALS HAVING SULFONAMIDO LINKED POLY(OXYALKYLENE) MOIETIES AND THEIR PREPARATION

FIELD OF INVENTION

This application is a continuation of Ser. No. 07/491,419 filed Mar. 9, 1990 and abandoned.

This invention concerns organic materials particularly metal free organic compounds which are either colorants, U.V. absorbers, stabilizers, plasticizers, or the like, or which are reactive intermediates for their manufacture, which compounds have linked thereto through sulfonamido groups, one or more poly(oxyalkylene) moieties which impart to or improve one or more chemical or physical properties of the compounds such as liquidity, solvent solubility, compatibility with liquids, with thermosettable resinous materials, or with thermoplastic polymeric materials, primary hydroxyl enrichment, hydroxyl reactivity enhancement, branching density, melting point lowering, improved pH stability, or non-fiber or non-skin staining.

The utility and desirability in a general sense for incorporating certain poly(oxyalkylene) materials into organic compounds, particularly into colorant compounds, are disclosed in the literature such as in U.S. Pat. Nos. 4,761,502; 4,284,729; 4,751,254; 4,812,141; 4,167,510; 4,141,684; 3,157,633; and 4,640,690, the disclosures of which are hereby incorporated by reference. All of these patents teach the linking of the poly(oxyalkylene) moiety to the chromophore through amino groups since the standard method for associating the poly(oxyalkylene) with a compound is through the reaction of the epoxy reactant with an amino group on the compound. However, such a reaction is not always convenient as such amino groups are not easily placed on many organic compounds.

In regard to the new colorant compositions of the present invention, an important utility for one embodiment is for the tinting or deeper coloring of natural and synthetic polymeric or resinous materials or substrates, especially polyurethanes and other thermosetting resins and polyolefins, wherein the chemical structures of the colorants are readily tailored to meet, in exceptional manner, the physical and chemical requirements of the specific industrial application.

Some of the desired physical and chemical characteristics of such colorants in addition to having at least substantial tinctorial power, include one or more of excellent clarity and light fastness, high heat stability, crystal structure and shade immutability, availability as liquids or at least good resin compatibility at typical processing temperatures for easy blending with the substrate, easy clean-up from processing, homogeneity of dispersal in the substrate, non-nucleating propensity of the colorant, and resistance to migration, settling, streaking, plating, subliming, blooming or the like of the colorant from the substrate.

Another embodiment of the invention has particular utility as polymeric tint compositions useful for providing coloration to aqueous systems used in the industrial sanitary supply market. More particularly, certain of the present compositions are useful for coloring liquids and are non-staining, water-washable, stable at high pH ranges, non-hazardous and biodegradable. More specifically, the present colorants have a desired or specific range of absorption, such as yellow colorants having an absorption range of 400-430 nanometers.

In regard to this particular utility, industrial sanitary supplies include hard surface detergent cleaners, toilet sanitizers, deodorant formulations, soaps, emulsifiers, and detergents. Currently, acid dyes are the colorants of choice in this market and are typically bright colors which offer a wide range of pH stability to the industrial cleaners. Some of the more common of these colorants are C.I. Acid Yellow 17, FD&C Yellow 5, and FD&C Red 40. Such acid dyes, however, have numerous disadvantages, including that they are typically powders which have poor flow characteristics and are potential dusting hazards leading to contamination of the work environment. These dyes are also not entirely fugitive from the surfaces they come in contact with and thus tend to stain clothing, counter tops, hands, and the like. Compatibility problems of these dyes with sanitary chemicals have also been known to occur due to the insolubility and ionic nature of the dyes.

The present organic materials on the other hand, for the most part are polymeric, amorphous liquids. The liquid colorant system eliminates the dusting problems and enhances the fugitivity from various substrates. The polymeric nature also renders the colorant more compatible with the various cleaning chemicals due to its unique internal emulsifying constituents. The present colorants also exhibit improved pH stability and have shades very similar to C.I. Acid Yellow 17, FD&C Yellow 5, and FD&C Red 40. Other advantages are the non-staining characteristics to hands, clothing, and other substrates as well as being water-washable, non-hazardous, and biodegradable.

Objects therefore of the present invention are: to provide organic materials, especially colorants which are improved in one or more properties such as liquidity, solvent solubility, pH stability, compatibility with liquids, with thermosettable resinous materials, or with thermoplastic polymeric materials, primary hydroxyl enrichment, hydroxyl reactivity enhancement, melting point lowering, or non-fiber or non-skin staining; and to provide a highly simplified method for their manufacture.

SUMMARY OF THE INVENTION

These and other objects have been attained in accordance with the present invention defined in its process embodiment as the process for chemically modifying metal-free, organic material for improving one or more properties thereof such as water dispersibility, compatibility with other organics, or increased chemical reactivity, said process comprising providing said material having from 1-6 sulfonylhalide groups or sulfonate ester groups or mixtures thereof, and contacting the same under sulfonamido forming conditions with one or more reactants containing one or more poly(oxyalkylene) moieties, each said reactant having from 1 to 6 functional amine groups, and being comprised of from about 4 to about 200 epoxide reactant residues of 2-4 carbons.

In certain preferred embodiments: said poly(oxyalkylene) moiety contains a total of from about 3.0 to about 30 mole percent of epoxide residue linking groups selected from one or more of divalent or trivalent, straight or branched aliphatic hydrocarbon of 2-15 carbons, alkylenedioxy, alkylenetrioxy, or groups containing one or more of N, O or S or combinations thereof;

said residue linking groups are selected from —NR$_1$—, —NR$_1$SO$_2$NR$_1$— or —NH—C(=O)—NH—, wherein R$_1$ is selected from hydrogen, a poly(oxyalkylene) moiety as defined, or unsubstituted or substituted alkyl, aryl, or cycloalkyl;

said amine groups have the formula HN(R$_1$)— wherein R$_1$ is selected from hydrogen, a poly(oxyalkylene) moiety as defined, or unsubstituted or substituted alkyl, aryl, or cycloalkyl; and said organic material contains one or more of the unsubstituted or substituted reaction residues of anthraquinone compounds, condensed anthraquinone compounds, electron rich aromatic active hydrogen compounds capable of undergoing electrophilic substitution reactions, aromatic mono-, bis- or tris-azo compounds, mono- or bi-carbocyclic aromatic compounds, heterocyclic aromatic compounds containing one or more of N, O or S or combinations thereof, triphenodioxazine compounds, or triarylmethane compounds.

In general, the present compositions comprise a metal-free organic compound of the formula A'[SO$_2$N(R$_1$)—Y]$_{1-6}$ having one or more improved properties of water dispersibility, compatibility with other organics, or increased chemical reactivity, wherein: A' is organic material; Y is an unsubstituted or substituted polymeric segment of from about 30 to 100 weight percent total of one or more poly(oxyalkylene) moieties each of which is comprised of the reaction residues of from about 4 to about 200 epoxide reactants at least about 50 mole percent of which contain 2-4 carbons; and R$_1$ is selected from hydrogen, Y, or unsubstituted or substituted alkyl, aryl or cycloalkyl.

Certain other preferred embodiments of the method and composition are given in the appended claims.

In the above definitions: Y can be terminated by H, or by or contain as branch substitutes, 1-3 groups or moieties selected from alkyl, cycloalkyl, acyl, or aryl; any of the above recited hydrocarbon groups, moieties or substituents may themselves be substituted, for example, or may contain multiple substituents selected from alkyl, halogen, alkoxycarbonyl, hydroxy, alkoxy, alkylenedioxy, urea or substituted urea, amino or substituted amino, acylamino or substituted acylamino, acyloxy or the like substituents which are known in the art; and each aliphatic hydrocarbon portion or moiety of the groups, moieties or substituents recited above, where not otherwise specified, contains from 1-20, preferably 1-12 carbons. In certain other preferred embodiments the poly(oxyalkylene) moiety carries substantial hydroxyl functionality, and for certain utilities the hydroxyl functionality is most preferably patterned in a more dense or spatially confined manner.

It is noted and is shown in the various examples of the preformed poly(oxyalkylene) containing reactants that the poly(oxyalkylene) moieties which naturally terminate with hydrogen at the end of the epoxide polymerization have been reacted further with materials such as ammonia. Also, additional groups can be added during poly(oxyalkylene) preparation by selection of the various nucleophiles to be reacted with the epoxide reactants. Also such groups, e.g., ketals may be subsequently hydrolyzed and the hydroxy groups further reacted such as by acylation, or amination. Such groups are shown in the reactant examples given below and are exemplified by alkoxy, phenoxy, dihydroxyalkyl, hydroxyalkyl, cyclic acetal (dihydroxy compound reacted with ketone), aminoalkyl, acyloxyalkyl or diacyloxyalkyl.

It is noted that one of the primary purposes of the present invention is to provide polymeric colorants which color thermoplastic and thermosetting resins without settling, streaking, subliming, or migrating and which provide uniform coloring throughout the entire resin. Also, the present polymeric colorants often provide improved clarity over conventional pigments. In addition, it is highly desirable that the colorants be easily removed from the equipment used to add the colorant to the resin. We have found that the present colorants can be used to color homogeneously a variety of thermoplastic and thermosetting resins and that aqueous cleaning is greatly facilitated as compared to conventional colorants.

DISCUSSION OF PRIOR ART

U.S. Pat. No. 2,730,534 shows anthraquinone dyestuffs useful for dyeing textile fibers and which contain —SO$_2$NH(CH$_2$CH$_2$O)$_n$—H groups where n equals 1, 2 or 3. These compounds, however, are solids and quite insoluble in water and thus are primarily useful as disperse dyestuffs. Also, it is known to prepare polymeric colorants containing sulfonamido groups which link the chromophore to a polymeric portion. See U.S. Pat. Nos. 4,051,038; 4,144,252; and 4,167,422. In these colorants, however, the polymeric portion consists of a polyvinyl amine residue and exhibit poor solubility in water. Thus, they must be reacted further to incorporate additional sulfonic groups thereinto for enhancing their water solubility.

In regard to the prior art polymeric colorants being solids, the liquid nature of the present compounds allows them to be blended uniformly into a variety of thermoplastic or thermosetting resins. In contrast, the solid prior art colored polymeric compositions be converted into fine particles, dispersed properly in some medium and then blended homogeneously with the resin to be colored.

STATEMENT OF MORE SPECIFIC EMBODIMENTS OF INVENTION

More specific aspects of the invention include that the organic material contains one or more of the unsubstituted or substituted reaction residues of anthraquinone compounds, condensed anthraquinone compounds, electron rich aromatic active hydrogen compounds capable of undergoing electrophilic substitution reactions, aromatic azo compounds, mono-or bi-carbocyclic aromatic compounds, heterocyclic aromatic compounds containing one or more of N, O or S or combinations thereof, triphenodioxazine compounds, or triarylmethane compounds.

Furthermore, it is preferred that colorant intermediates to have the formula A"[SO$_2$N(R$_1$)—Y]$_{1-6}$, and wherein in the process the said organic material has the formula A(SO$_2$X)$_{1-6}$, wherein X is halogen or lower alkoxy, Y is the residue of said reactant, and A is an organic residue selected from unsubstituted or substituted: anilines; 1,2,3,4-tetrahydroquinolines; 2,3-dihydroindoles; 2,3-dihydro-1,4-benzoxazines(benzomorpholines); naphthylamines; 2-aminothiophenes; phenols; naphthols; 2-aminothiazoles; indoles; imidazothiazoles; 5-pyrazolones; 2-pyridones or acetoacetarylides.

A particularly useful moiety for A includes those residues of the formulae

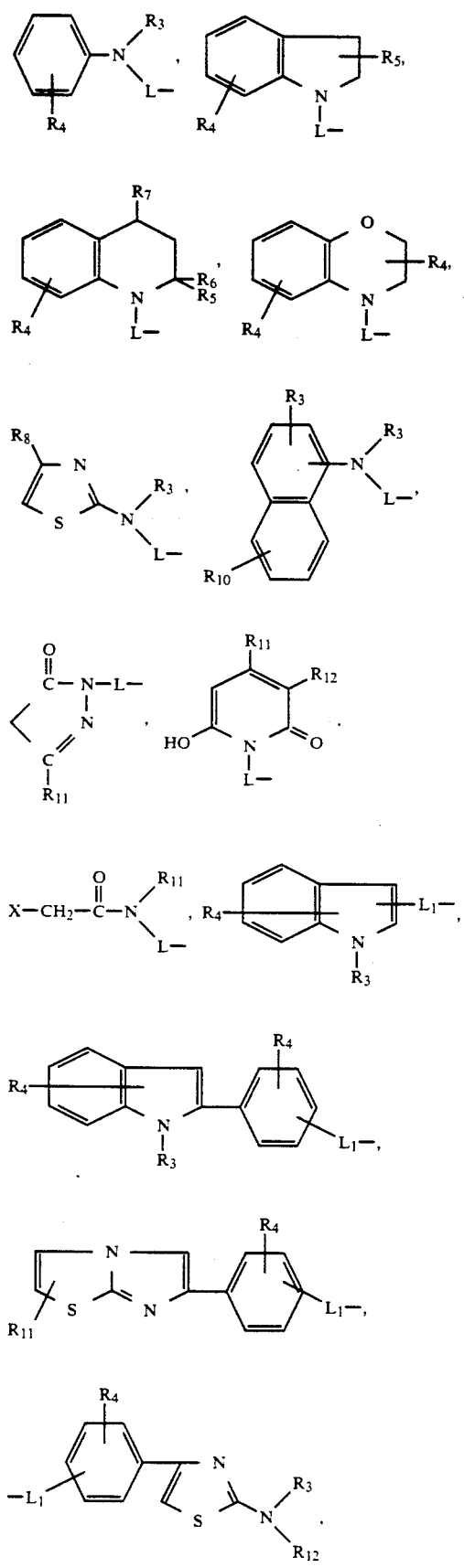
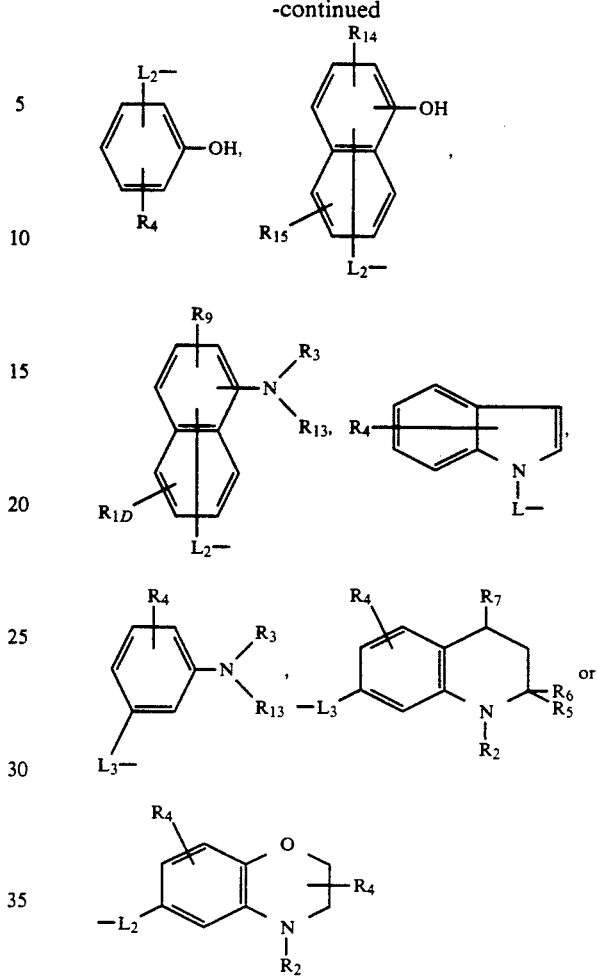

wherein:

L is selected from unsubstituted or substituted: alkylene; arylene; aralkylene; alkylene —Z— alkylene; alkylene —Z— arylene; arylene —Z— arylene; aralkylene —Z— arylene; or aralkylene —Z— aralkylene; wherein Z is selected from O, S, $SO_2$, $N(R_2)$, $SO_2N(R_2)$ or $N(R_2)CON(R_2)$, and $R_2$ is selected from hydrogen or unsubstituted or substituted alkyl, cycloalkyl or aryl;

$L_1$ is a covalent bond;

$L_2$ is selected from L and $L_1$;

$L_3$ is selected from -Z-alkylene, -Z-aralkylene, -Z-arylene, or alkylene-Z-arylene;

X' is selected from cyano, alkanoyl, aroyl, alkoxycarbonyl or unsubstituted or substituted carbamoyl;

$R_3$ is selected from: hydrogen; unsubstituted or substituted alkyl, cycloalkyl or aryl; or —L—$SO_2N(R_1)Y$;

$R_4$ is hydrogen or 1-3 groups selected from lower alkyl, lower alkoxy or halogen;

$R_5$, $R_6$, and $R_7$ are selected from hydrogen or lower alkyl;

$R_8$ is selected from hydrogen, or unsubstituted or substituted lower alkyl, cycloalkyl or aryl;

$R_9$ and $R_{10}$ are independently selected from hydrogen, or 1-3 groups selected from lower alkyl, lower alkoxy, $SO_3H$, hydroxyl or halogen;

$R_{11}$ is selected from hydrogen, lower alkyl, cycloalkyl or aryl;

$R_{12}$ is selected from cyano, carboxylic acid ester, or unsubstituted or substituted carbamoyl;

$R_{13}$ is selected from one of the groups represented by $R_3$;

$R_{14}$ is selected from hydrogen or 1-3 groups selected from lower alkyl, alkoxy, halogen, $SO_3H$, carboxy, carboxylic acid ester or unsubstituted or substituted carbamoyl; and $R_{15}$ is selected from hydrogen or 1-3 groups selected from lower alkyl, lower alkoxy, hydroxy, unsubstituted or substituted amino, alkanoylamino, aroylamino or $SO_3H$.

In the above definitions, the alkoxy and alkylene groups and preferably straight chained or branched chains containing 1 to about 12 carbon atoms. The cycloalkyl groups contain five to seven carbon atoms and the aryl groups consist preferably of unsubstituted and substituted phenyl, benzothiazolyl, benzoxazolyl, thiazolyl, benzimidazolyl, 1,3,4-thiadiazolyl, 1,2,4-thiadiazolyl, 1,3,4-oxadiazolyl, thienyl, naphthyl, pyridyl, quinolyl, or pyrimidinyl.

In a certain prefered embodiment: the poly(oxyalkylene) moiety is linked to a plurality of A' materials through sulfonamido groups;

A' contains one or more of the unsubstituted or substituted reaction residues of anthraquinone compounds, condensed anthraquinone compounds, electron rich aromatic active hydrogen compounds capable of under going electrophilic substitution reactions, aromatic mono-, bis- or tris- azo compounds, aromatic methine compounds, aromatic azamethine compounds, mono-or bicarbocycyclic aromatic compounds, heterocyclic aromatic compounds containing at least one or more of N, O or S or combinations thereof, triphenodioxazine compounds, or triarylmethane compounds; and A' is the reaction residue of a compound selected from unsubstituted or substituted: anilines; 1,2,3,4-tetrahydroquinolines; 2,3-dihydroindoles; 2,3-dihydro-1,4-benzoxazines; naphthylamines; phenols; 2-aminothiophenes; naphthols; 2-aminothiazoles; indoles; imidazothiazoles; 5-pyrazolones; 2-pyridones or acetoacetarylides.

Preferred condensed anthraquinones include those selected from substituted or unsubstituted: anthraquinone; 7H-Dibenz[f,ij]isoquinoline-7-one (anthrapyridine); 7H-Benzo[e]perimidine-7-one(anthrapyrimidine); 14H-Naphtho[2,3-a]phenothiazine-8,13-dione(phthaloylphenothiazine); 14H-Naphtho[2,3-a]phenoxazine-8,13-dione(phthaloylphenoxazine); 1H-Anthra(2,1-b)(1,4)-thiazine-7,12-dione; 1H-Anthra(2,1-b)(1,4)-thiazine-7,12-dione-S,S-dioxide; 7H-Benz[de]anthracen-7-one(benzanthrone); 13-Naphtho[2,3-c]acridine-5,8,14-trione(phthaloylacridone); 8H-Naphtho[2,3-c]thioxanthene-5,8,13-trione; Anthrapyridazone; Anthrapyrazole; Anthraisothiazole; Naphtho[1'2'3',:4,5-]quino[2,1-b]quinazoline-5,10-dione. 3H-Dibenz[f,ij]isoquinoline-2,7-dione(anthrapyridone) or 14H-Naphtho[2,3-a]phenothiazine-8,13-dione-S,S-dioxide.

It is further preferred that:

the poly(oxyalkylene) moiety contains from about 3 to about 30 mole percent of epoxide reactant residue linking groups selected from divalent or trivalent, straight or branched aliphatic hydrocarbon of 2-15 carbons, alkylenedioxy, alkylenetrioxy, or groups containing one or more of N, O or S or combinations thereof; and the linking groups are selected from $-NR_1-$, $-NR_1SO_2NR_1-$, or $-NHCONH-$.

A group of particularly useful intermediates are wherein A' is selected from those residues of the formulae

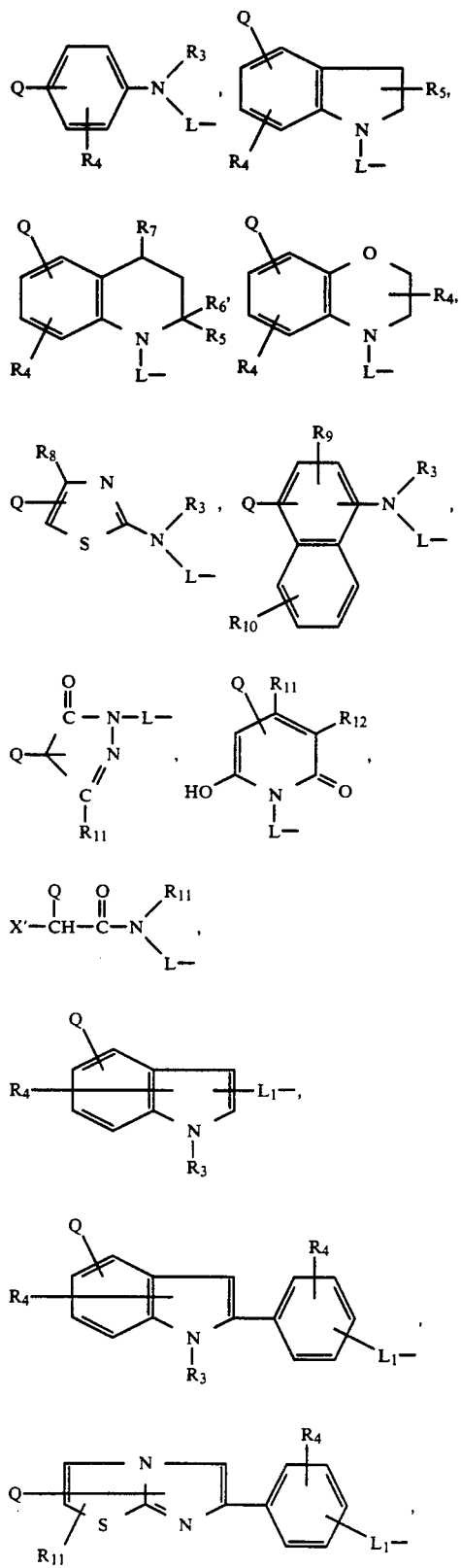

-continued

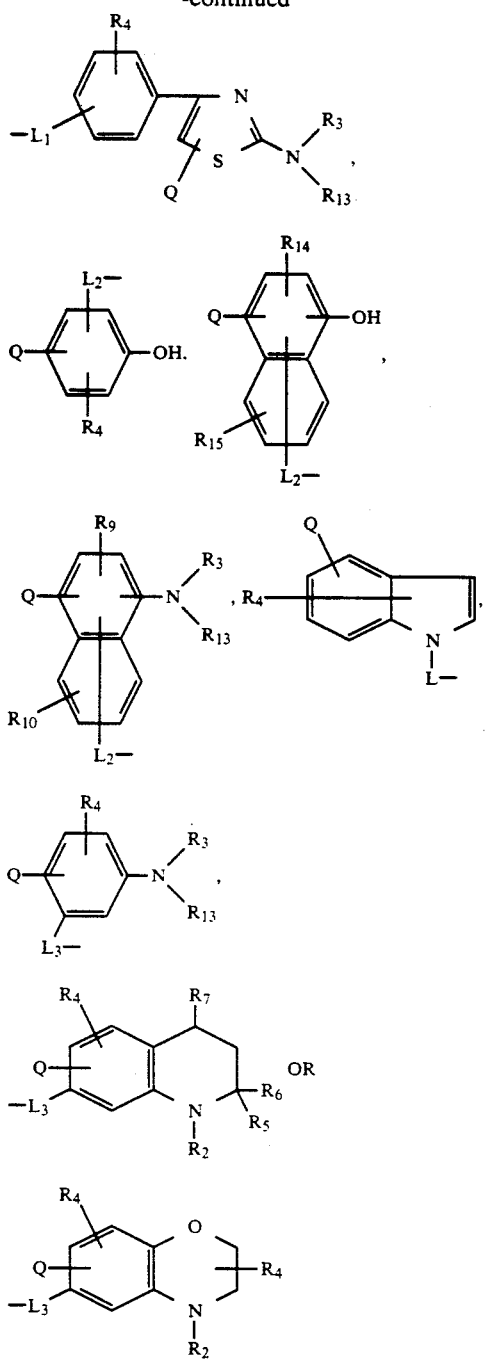

wherein:

L is selected from unsubstituted or substituted: alkylene; arylene; aralkylene; alkylene-Z-alkylene; alkylene-Z-arylene; arylene-Z-arylene; aralkylene-Z-arylene; or aralkylene-Z-aralkylene; wherein Z is selected from O, S, $SO_2$, $N(R_2)$, $SO_2N(R_2)$ or $N(R_2)CON(R_2)$, and $R_2$ is selected from hydrogen or unsubstituted or substituted alkyl, cycloalkyl or aryl;

$L_1$ is a covalent bond;

$L_2$ is selected from L and $L_1$;

$L_3$ is selected from -Z-alkylene, -Z-aralkylene, -Z-arylene, or alkylene-Z-arylene;

X' is selected from cyano, alkanoyl, aroyl, alkoxycarbonyl or unsubstituted or substituted carbamoyl;

$R_3$ is selected from: hydrogen; unsubstituted or substituted alkyl, cycloalkyl or aryl; or $-L-SO_2N(R_1)Y$;

$R_4$ is hydrogen or 1-3 groups selected from lower alkyl, lower alkoxy or halogen;

$R_5$, $R_6$ and $R_7$ are selected from hydrogen or lower alkyl;

$R_8$ is selected from hydrogen, or unsubstituted or substituted lower alkyl, cycloalkyl or aryl;

$R_9$ and $R_{10}$ are independently selected from hydrogen or 1-3 groups selected from lower alkyl, lower alkoxy, $SO_3H$, hydroxyl or halogen;

$R_{11}$ is selected from hydrogen, lower alkyl, cycloalkyl or aryl;

$R_{12}$ is selected from cyano, carboxylic acid ester, or unsubstituted or substituted carbamoyl;

$R_{13}$ is selected from one of the groups represented by $R_2$;

$R_{14}$ is selected from hydrogen or 1-3 groups selected from lower alkyl, alkoxy, halogen, $SO_3H$, carboxy, carboxylic acid ester or unsubstituted or substituted carbamoyl; and $R_{15}$ is selected from hydrogen or 1-3 groups selected from lower alkyl, lower alkoxy, hydroxy, unsubstituted or substituted amino, alkanoylamino, aroylamino or $SO_3H$.

Q is selected from: hydrogen; $-N=O$; $-NH_2$; $-NH-NH_2$; $NO_2$; $COR_2$ wherein $R_2$ is selected from hydrogen, unsubstituted or substituted alkyl, cycloalkyl, or aryl; $N_2{}^+X^-{}_2$ wherein $X^-$ is a counterion; $-N=CH-R_2'$, wherein $R_2'$ is selected from alkyl, cycloalkyl or aryl; or $-CH=N-R_2'$, A highly preferred group of intermediates are wherein A is the residue of a mono- or bi-cyclic aromatic compound selected from unsubstituted or substituted nitrophenyl or acylaminophenyl, an unsubstituted or substituted nitronaphthyl or acylaminonaphthyl, or an unsubstituted or substituted heterocyclic aromatic compound selected from: benzothiazole; thiazole; 1,3,4-thiadiazole; 1,2,4-thiadiazole; isothiazole; 2,1-benzisothiazole; thienyl; or pyrazole, and containing at least one acylamino group.

Preferred intermediates wherein A' is an acylamino heterocyclic residue are those of the formulae:

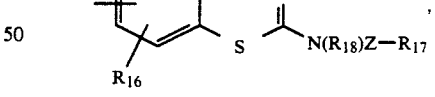

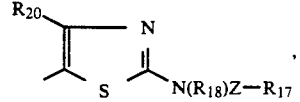

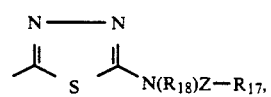

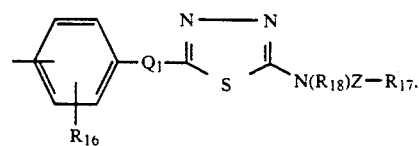

-continued

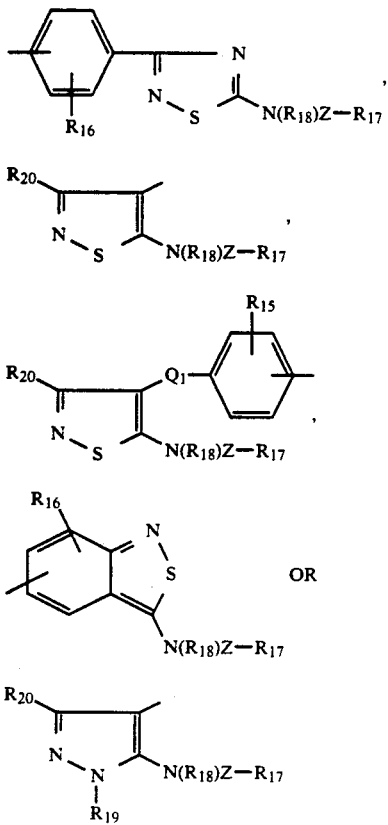

wherein:

$R_{16}$ is hydrogen or 1-3 groups selected from lower alkyl, lower alkoxy or halogen; and Z is selected from —CO— —OCO— or $SO_2$;

$R_{17}$ is selected from lower alkyl; lower alkoxy; alkylamino; arylamino; cycloalkyl; phenyl; phenyl substituted with lower alkyl, and lower alkoxy or halogen; and when Z is —CO—, $R_{17}$ can also be hydrogen;

$R_{18}$ is selected from hydrogen, lower alkyl or cycloalkyl;

$R_{19}$ is selected from hydrogen, lower alkyl or cycloalkyl, $COR_{17}$ or $SO_2R_{17}$;

$R_{20}$ is selected from hydrogen, lower alkyl, cycloalkyl or aryl; and $Q_1$ is selected from a covalent bond, oxygen, sulfur, alkyleneoxy, alkylenethio, oxyalkyleneoxy, oxyalkylenethio or thioalkylenethio.

Certain particularly preferred compositions are those of the following formulae I-VII:

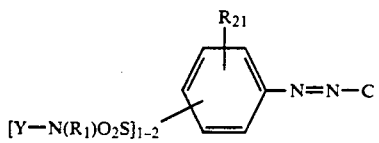 (I)

wherein:

$R_{21}$ is hydrogen or 1-3 groups selected from lower alkyl, lower alkoxy or halogen; and C is a colorant coupling component residue selected from pyrazolones, phenols, 2-naphthols, pyridones or acetoacetarylides;

those wherein the coupling component contains at least one sulfonic acid group or salt thereof;

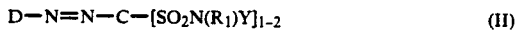 (II)

wherein:

D is a carbocyclic or heterocyclic diazotizable amine residue;

C is an azo colorant coupling component residue, selected from anilines, indoles, 1,2,3,4-tetrahydroquinolines, 2,3-dihydro-1,4-benzoxazines(benzomorpholines), naphthylamines, 2-aminothiazoles, 2-aminothiophenes, actoacetarylides, 2,3-dihydroindoles, imidazothiazoles, phenols, naphthols, pyrazolones or pyridones;

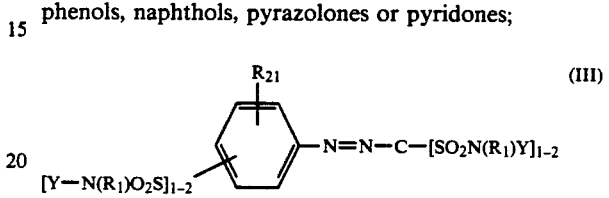 (III)

wherein:

$R_{21}$ is hydrogen or 1-3 groups selected from lower alkyl, lower alkoxy or halogen; and C is an azo colorant coupling component residue selected from anilines, indoles, 1,2,3,4-tetrahydroquinolines, 2,3-dihydro-1,4-benzoxazines(benzomorpholines), naphthylamines, thiazoles, acetoacetarylides, 2-aminothiophenes, 2,3-dihydroindoles, imidazothiazoles, phenols, naphthols, pyrazolones or pyridones;

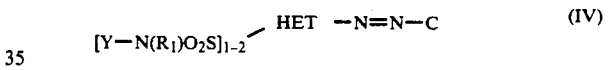 (IV)

wherein:

HET is the residue of a diazotizable heterocyclic amine component selected from 2-aminothiazoles, 2-aminobenzothiazoles, 2-amino-1,3,4-thiadiazoles, 5-amino-1,2,4-thiadiazoles, 5-aminoisothiazoles, 3-amino-2,1-benzisothiazoles, 2 or 3-aminothiophenes, 3 or 4-aminophthalimides, 4-aminonaphthalimides or 5-aminopyrazoles;

C is an azo colorant coupling component residue selected from anilines, indoles, 1,2,3,4-tetrahydroquinolines, 2,3-dihydro-1,4-benzoxamines(benzomorpholines), naphthylamines, 2-aminothiazoles, acetonacetarylides, 2-aminothiophenes, 2,3-dihydroindoles, imidazothiazoles, phenols, naphthols, pyrazolones or pyridones;

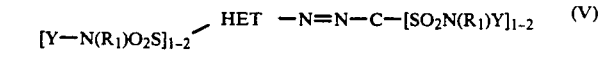 (V)

wherein:

HET is the residue of a diazotizable heterocyclic amine component selected from 2-aminothiazole, 2-aminobenzothiazoles, 2-amino-1,3,4-thiadiazoles, 5-amino-1,2,4-thiadiazoles, 5-aminoisothiazoles, 3-amino-2,1-benzisothiazoles, 2 or 3-aminothiophenes, 3 or 4-aminophthalimides, 4-aminonaphthalimides or 5-aminopyrazoles;

C is an azo colorant coupling component residue selected from anilines, indoles, 1,2,3,4-tetrahydroquinolines, 2,3-dihydro-1,4-benzoxazines(benzomorpholines), naphthylamines, 2-aminothiazoles, acetoacetarylides, 2-aminothiophenes, 2,3-dihydroindoles, imidazothiazoles, phenols, naphthols, pyrazolones or pyridones;

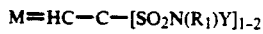

$$M=HC-C-[SO_2N(R_1)Y]_{1-2} \quad (VI)$$

wherein:

M is an active methylene residue, and C is the residue of a reactant selected from substituted or unsubstituted: anilines; naphthylamines; 1,2,3,4-tetrahydroquinolines; 2,3-dihydro-1,4-benzoxazines; 2-aminothiazoles; 2,3-dihydroindoles; or 2-aminothiophenes; and

$$M=N-C-[SO_2N(R_1)Y]_{1-2} \quad (VII)$$

wherein:

M is an active methylene residue, and C is the residue of a reactant selected from substituted or unsubstituted: anilines; naphthylamines; 1,2,3,4-tetrahydroquinolines; 2,3-dihydro-1,4-benzoxazines; 2-aminothiazoles; 2,3-dihydroindoles; or 2-aminothiophenes.

PRACTICE OF THE INVENTION, MATERIALS, REACTION CONDITIONS AND EXAMPLES

The types of organic materials to which the present invention is applicable are essentially limited only by the practicality of providing the material with one or more halogenosulfonyl or sulfonate ester groups without adversely affecting the properties of or deteriorating the material.

The halogenosulfonation of these materials may be done on the organic material itself or on one or more intermediates thereof by any of the known halogenosulfonation methods.

The halosulfonyl compounds may also be prepared from the intermediate sulfonic acids or salts thereof by reacting with known halogenating agents such as phosphorous pentachloride, phosphorous trichloride, phosphorous oxychloride, phosphorous tribromide, phosphorous oxybromide or thionyl chloride or mixtures thereof. A convenient synthetic method for preparing 2-(fluorosulfonylethyl) compounds involves the reaction of known vinylsulfonyl fluoride with organic compounds, e.g., anilines and aminoanthraquinones.

The intermediate sulfonate ester containing reactants may be prepared by reaction of the corresponding halosulfonyl compounds with alkali metal alkoxides (e.g. sodium methoxide) or with alcohols in the presence of base to generate the alkoxide "in situ".

In general, the organic material containing one or more said sulfonylhalide groups are reacted with amine reactants containing the poly(oxyalkylene) moiety by combining the two reactants in roughly equal stoichiometric amounts or with a slight excess of the amine reactant at temperatures from about 0°-100° C., with temperatures of about 30°-60° C. being preferred. Reaction solvents include water, alcohols, ketones, glycols, glycol ethers, pyridine, N,N-dimethylformamide, N-methyl-2-pyrrolidinone, ethers or mixtures thereof, preferably with an acid acceptor present such as alkali hydroxides, alkali carbonates, alkali bicarbonates, or tertiary amines.

Commercially available and preferred amines from which the present preferred colorants are prepared are the JEFFAMINE series described in Texaco Chemical Company, New Product Development brochures as the M, D, ED, DU, BUD, T, MNPA: and EDR series: the disclosures of which are incorporated herein by reference and copies of which are transmitted herewith.

The preferred aliphatic amines finding special utility in the present invention are as follows:

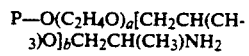

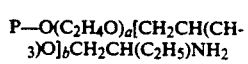

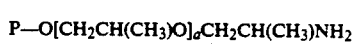

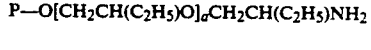

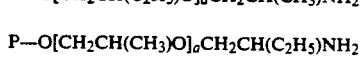

$$P-O[CH_2CH(CH_3)O]_aCH_2CH(C_2H_5)NH_2$$

wherein a=1-19; b=2-31; and P is selected from $CH_3$, $C_2H_5$, n-$C_3H_7$, n-$C_4H_9$, n-$C_5H_{11}$, or n-$C_6H_{13}$.

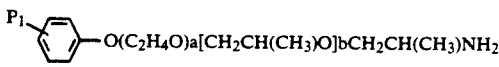

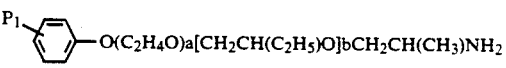

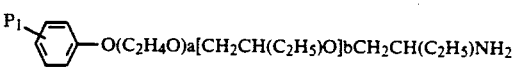

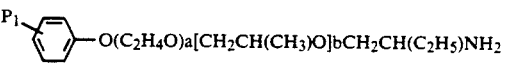

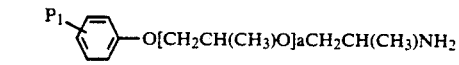

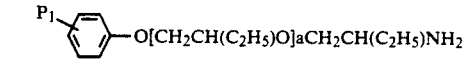

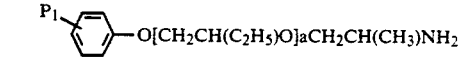

wherein a=1-19; b=2-31; and $P_1$ is selected from $CH_3$, $C_2H_5$, $C_4H_9$, $C_9H_{19}$, $OCH_3$, $OC_2H_5$, or $OC_4H_9$.

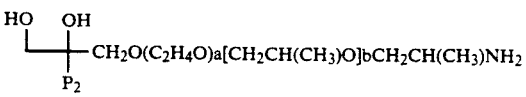

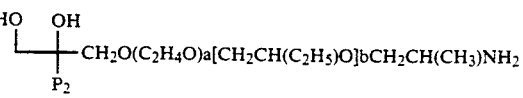

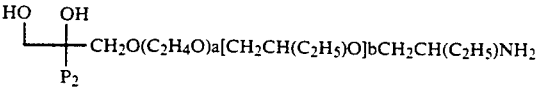

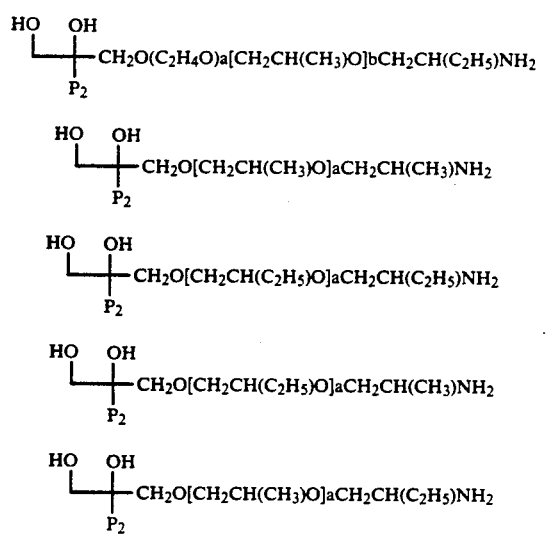
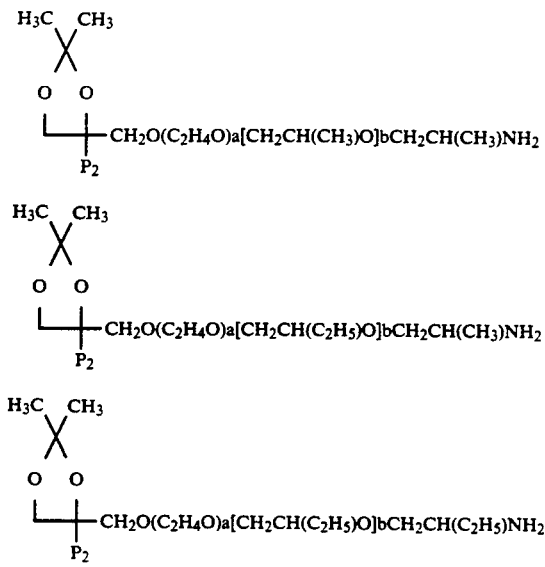
wherein a=1-19; b=2-31; and P₂ is selected from hydrogen, CH₃, or C₂H₅.
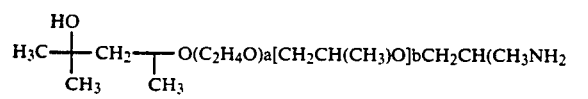
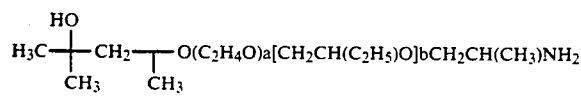
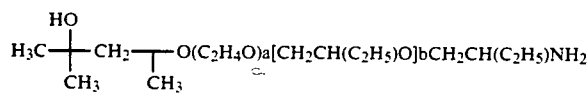
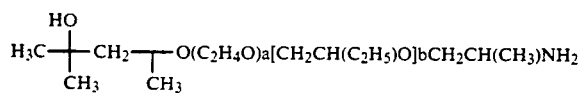
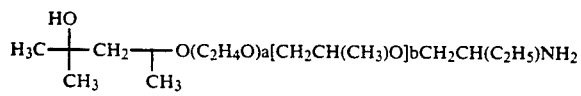
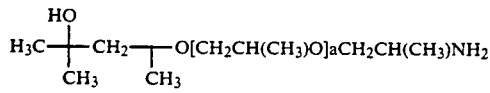
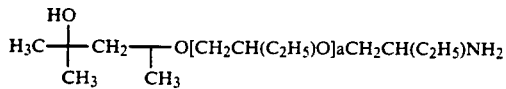
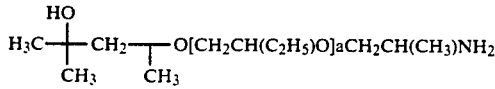
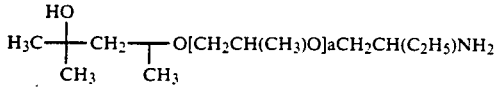
wherein a=1-19; b=2-31.

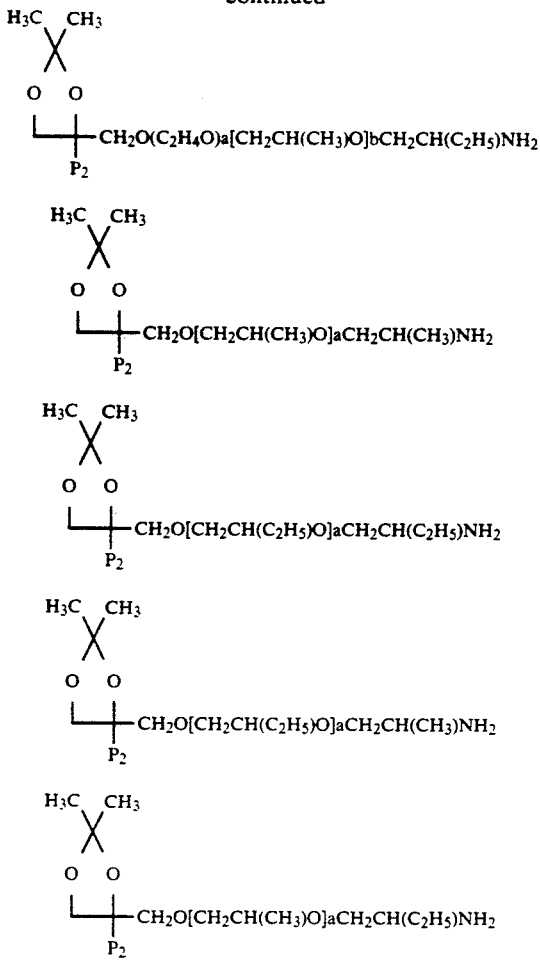

wherein a=1-19; b=2-31; and P₂ is recited above.

H₂NCH(CH₃)CH₂[OCH(CH₃)CH₂]ₐ(OCH₂CH₂)-
ᵦ[OCH₂CH(CH₃)]꜀NH₂

H₂NCH(CH₃)CH₂[OCH(C₂H₅)CH₂]ₐ(OCH₂CH₂)-
ᵦ[OCH₂CH(CH₃)]꜀NH₂

H₂NCH(CH₃)CH₂[OCH(C₂H₅)CH₂]ₐ(OCH₂CH₂)-
ᵦ[OCH₂CH(C₂H₅)]꜀NH₂

H₂NCH(C₂H₅)CH₂[OCH(C₂H₅)CH-
₂]ₐ(OCH₂CH₂)ᵦ[OCH₂CH(C₂H₅)]꜀NH₂

H₂NCH(C₂H₅)CH₂[OCH(CH₃)CH₂]ₐ(OCH₂CH₂)-
ᵦ[OCH₂CH(C₂H₅)]꜀NH₂

H₂NCH(CH₃)CH₂[OCH(CH₃)CH₂]ₐNH₂

H₂NCH(C₂H₅)CH₂[OCH(C₂H₅)CH₂]ₐNH₂ wherein b=4-132; and a+c=2-5.

H₂N(CH₃)CHCH₂[OCH₂CH(CH₃)]ₐHN-
(CO)NH[CH(CH₃)CH₂O]ᵦCH₂CH(CH₃)NH₂

H₂N(C₂H₅)CHCH₂[OCH₂CH(C₂H₅)]ₐHN-
(CO)NH[CH(C₂H₅)CH₂O]ᵦCH₂CH(C₂H₅)NH₂

H₂N(CH₃)CHCH₂[OCH₂CH(C₂H₅)]ₐHN-
(CO)NH[CH(C₂H₅)CH₂O]ᵦCH₂CH(CH₃)NH₂

H₂N(C₂H₅)CHCH₂[OCH₂CH(CH₃)]ₐHN-
(CO)NH[CH(CH₃)CH₂O]ᵦCH₂CH(C₂H₅)NH₂ wherein a=2-68 and b=2-68.

HOCH(CH₃)CH₂NHCH(CH₃)CH-
₂[OCH₂CH(CH₃)]ₐNHCH₂CH(CH₃)OH wherein a is 2.6.

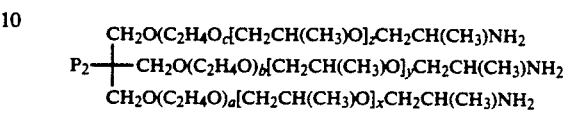

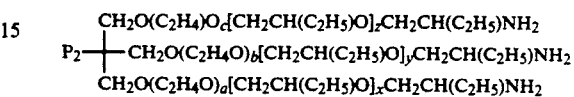

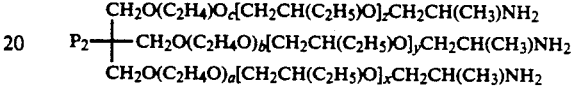

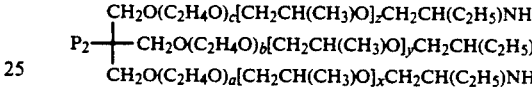

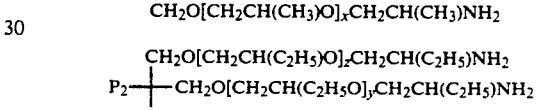

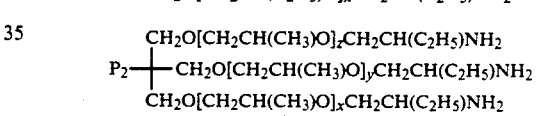

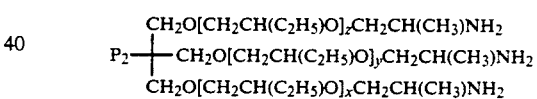

wherein a+b+c=1-80; and x+y+z=5-85; and P₂ is recited above.

The preferred aromatic amines finding special utility in the manufacture of the preferred colorants of the present invention are prepared according to Routes 1-6.

Route 1

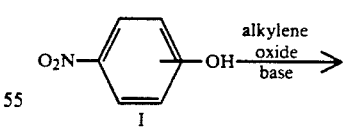

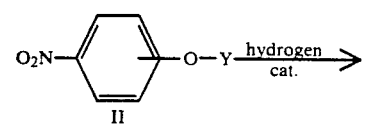

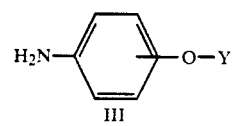

Route 1 involves the hydroxyalkylation of a nitrophenol (I) with an alkylene oxide in the presence of a base catalyst. Suitable alkylene oxides include, for example, ethylene oxide, propylene oxide, butylene oxide, and mixtures of two or more of such compounds.

The hydroxyalkylation reaction may be accomplished by the reaction of alkylene oxide at about 80°-150° C. The alkylene oxide is added in the presence of an inert gas such as nitrogen until the desired amount of alkylene oxide has been absorbed. This reaction is carried out with or without solvents. If solvents are desired, toluene, xylenes, nitrobenzene, dioxane are just a few solvents that may be used.

Useful basic catalysts are e.g. potassium hydroxide, lithium hydroxide, calcium hydroxide, and barium hydroxide. The amount of basic catalyst can vary but is usually in the range of from about 0.2% to about 2% by weight. In addition, certain tertiary organic amines are useful catalysts, such as dimethylaminocyclohexane, triethylamine, and benzyldimethylamine. The poly(oxyalkylated) nitro intermediates (II) are converted into aromatic amines (III) by catalytic hydrogenation. Any suitable reduction catalyst may be used. For example, catalysts such as Raney nickel, nickel oxides, finely divided metals such as iron, cobalt, platinum, ruthenium, osmium, and rhodium may be used. Furthermore, metal catalysts supported on pumice, asbestos, Kieselguhr, alumina, silica gel or charcoal work equally as well. The amount of catalyst can vary usually from about 0.025 to 15 percent by weight based on the nitro intermediate (II) used.

Reduction temperatures of about 20° C. to about 90° C., although temperatures of 40° C. to 90° C. are preferred since they may provide faster reaction times and higher yields of the aromatic amines (III). During the reduction of the nitro intermediates (II), pressures ranging from about 500 to about 1800 psi of hydrogen may be used.

The reduction reaction is usually carried out in the presence of a suitable solvent. Solvents include lower alcohols such as methyl alcohol, ethyl alcohol, and isopropyl alcohol; ethers such as dioxane; hydrocarbons such as benzene, toluene, xylenes, cyclohexanes, and petroleum ether; and mixtures of lower alcohols and water such as about equal parts by weight of ethyl alcohol and water. The amount of solvent is an amount of about 30 to about 80 percent by weight.

Route 2

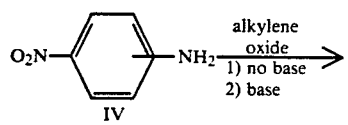

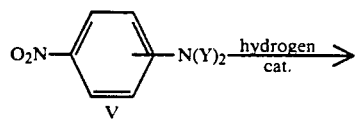

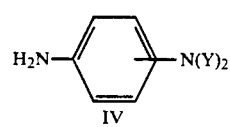

Route 2 involves the hydroxyalkylation of a nitroaniline (IV) with an alkylene oxide in a two-step procedure. The first step can be carried out in the presence or absence of a acid catalyst. Suitable alkylene oxides include, for example, ethylene oxide, propylene oxide, butylene oxide, cyclohexane oxide, glycidol, and mixtures of two or more of such compounds.

In the first step, hydroxyalkylation may be accomplished by the reaction of the alkylene oxide at about 80°-150° C. The alkylene oxide is added in the presence of an inert gas such as nitrogen until two or more equivalents of the desired amount of alkylene oxide have been absorbed. This reaction is carried out with or without solvents. If solvents are desired, toluene, xylenes, nitrobenzene, dioxane are just a few solvents that may be used. Alternatively, an acid catalyst can be employed to effect the hydroxyalkylation. For example, formic acid and acetic acid are just a few of such inert acids that may be used. Generally, acid-catalyzed hydroxyalkylation is performed at a lower temperature to avoid the formation of by-products. Temperatures from about 40° C. to about 120° C. can be employed depending on the basicity of the nitroaniline (IV) to be hydroxyalkylated. The amount of acid may vary widely. Generally from about 0.5 to 10 percent by may be employed.

In the second step, the nitropolyoxyalkylene intermediate (V) is prepared by the use of base catalysts such as potassium hydroxide, lithium hydroxide, calcium hydroxide, and barium hydroxide. The amount of basic catalyst can vary but is usually in the range of from about 0.2% to about 2% by weight. The reaction temperature can vary but may generally be in the range from 100° C. to about 150° C.

The corresponding aromatic amines (VI) are then prepared by conversion of the poly(oxyalkylene) nitro intermediates (V) by catalyst reduction as described in Route 1 above.

Route 3

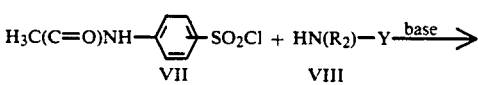

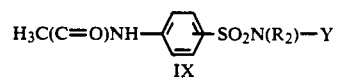

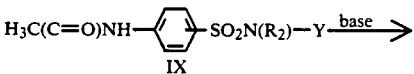

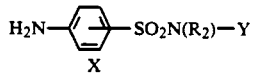

Route 4

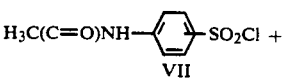

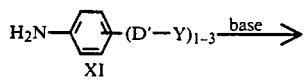

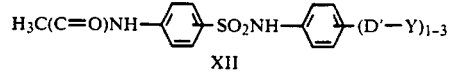

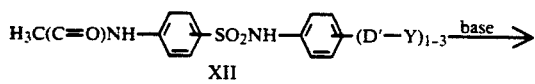

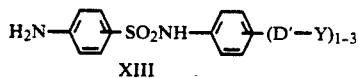

Route 3 involves the condensation of an acetamido sulfonyl chloride intermediate (VII) with at least a stoichiometric quantity of a aliphatic poly(oxyalkylene) amine (VIII) and a inorganic base at a temperature of from about 0° C. to about 100° C. to form an acetamidopoly(oxyalkylene) intermediate (IX).

Further heating at 80° C. to 100° C. hydrolyzes the corresponding acetamidopoly(oxyalkylene) intermediate (IX) into the aromatic poly(oxyalkylene) amine (X).

Similarly, Route 4 involves the condensation of an acetamidosulfonyl chloride intermediate (VII) with at least a stoichiometric quantity of a aromatic poly(oxyalkylene) amine (XI) and a inorganic base at a temperature of from about 0° C. to about 100° C. to form an acetamidopoly(oxyalkylene) intermediate (XII). Further heating at 80° C. to 100° C. hydrolyzes the corresponding acetamidopoly(oxyalkylene) intermediate (XII) into the aromatic poly(oxyalkylene) amine (XIII).

Route 5

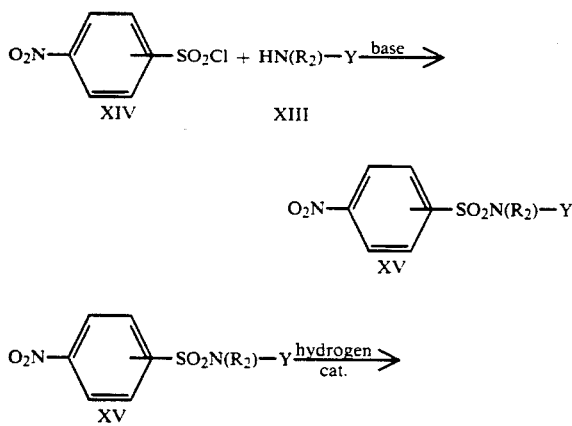

Route 6

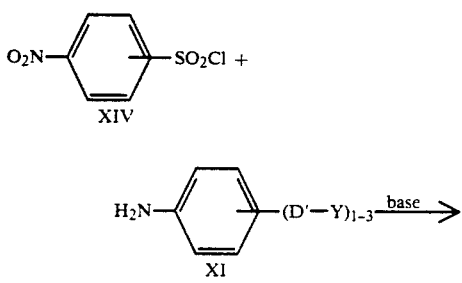

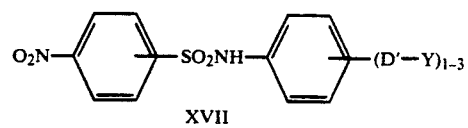

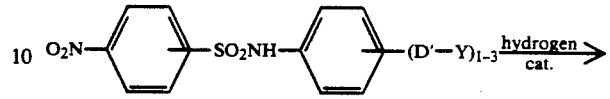

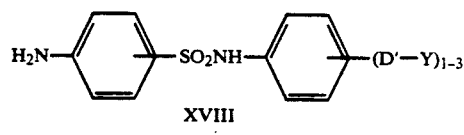

Route 5 involves the condensation of an nitrosulfonyl chloride intermediate (XIV) with at least a stoichiometric quantity of a aliphatic poly(oxyalkylene) amine (VIII) and an inorganic base at a temperature of from about 0° C. to about 100° C. to form a nitropoly(oxyalkylene) intermediate (XV).

The corresponding aromatic amine (XVI) is then prepared by conversion of the poly(oxyalkylene) nitro intermediate (XV) by catalytic reduction as described in Route 1 above.

Route 6 involves the condensation of a nitrosulfonyl chloride intermediate (XIV) with at least a stoichiometric quantity of an aromatic poly(oxyalkylene) amine (XI) and an inorganic base at a temperature of from about 0° C. to about 100° C. to form a nitropoly(oxyalkylene) intermediate (XVII).

The corresponding aromatic amine (XVIII) is then prepared by conversion of the poly(oxyalkylene) nitro intermediate (XVII) by catalytic reduction as described in Route 1 above.

In structures XII, XIII, XVII, XVIII, and XIX above, D' is selected from a covalent bond or a linking group selected from oxygen, sulfur, sulfonamide or amine.

The preferred aromatic amines finding special utility in the present invention are as follows:

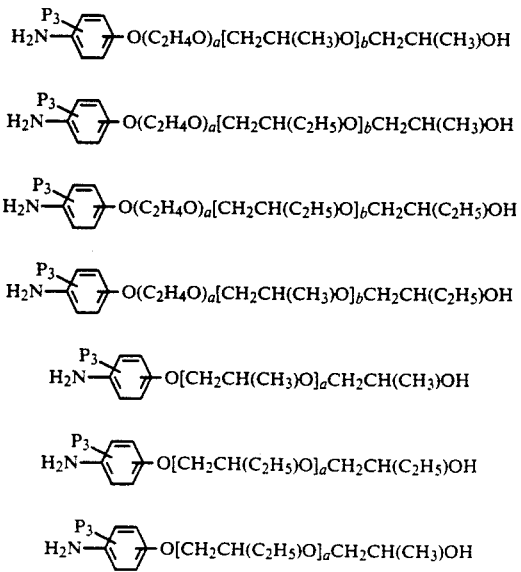

H₂N-[P₃-C₆H₄]-O[CH₂CH(CH₃)O]ₐCH₂CH(C₂H₅)OH

H₂N-[P₃-C₆H₄]-O(C₂H₄O)ₐCH₂CH₂OH

H₂N-[P₃-C₆H₄]-O(C₂H₄O)ₐCH₂CH(CH₃)OH

H₂N-[P₃-C₆H₄]-O(C₂H₄O)ₐCH₂CH(C₂H₅)OH

H₂N-[P₃-C₆H₄]-O(C₂H₄O)ₐ[CH₂CH(CH₃)O]ᵦCH₂CH₂OH

H₂N-[P₃-C₆H₄]-O(C₂H₄O)ₐ[CH₂CH(C₂H₅)O]ᵦCH₂CH₂OH

H₂N-[P₃-C₆H₄]-O[CH₂CH(CH₃)O]ₐCH₂CH₂OH

H₂N-[P₃-C₆H₄]-O[CH₂CH(C₂H₅)O]ₐCH₂CH₂OH wherein a=1-100; b=1-100; and P₃ is selected from CH₃, C₂H₅, n-C₃H₇, n-C₃H₇, n-C₄H₉, OCH₃, or OC₂H₅.

H₂N-[P₃-C₆H₄]-{N(C₂H₄O)ₐ[CH₂CH(CH₃)O]ᵦCH₂CH(CH₃)OH}₂

H₂N-[P₃-C₆H₄]-{N(C₂H₄O)ₐ[CH₂CH(C₂H₅)O]ᵦCH₂CH(CH₃)OH}₂

H₂N-[P₃-C₆H₄]-{N(C₂H₄O)ₐ[CH₂CH(C₂H₅)O]ᵦCH₂CH(C₂H₅)OH}₂

H₂N-[P₃-C₆H₄]-{N(C₂H₄O)ₐ[CH₂CH(CH₃)O]ᵦCH₂CH(C₂H₅)OH}₂

H₂N-[P₃-C₆H₄]-{N[CH₂CH(CH₃)O]ₐCH₂CH(CH₃)OH}₂

H₂N-[P₃-C₆H₄]-{N[CH₂CH(C₂H₅)O]ₐCH₂CH(C₂H₅)OH}₂

H₂N-[P₃-C₆H₄]-{N[CH₂CH(C₂H₅)O]ₐCH₂CH(CH₃)OH}₂

H₂N-[P₃-C₆H₄]-{N[CH₂CH(CH₃)O]ₐCH₂CH(C₂H₅)OH}₂

H₂N-[P₃-C₆H₄]-{N(C₂H₄O)ₐCH₂CH₂OH}₂

H₂N-[P₃-C₆H₄]-{N(C₂H₄O)ₐCH₂CH(CH₃)OH}₂

H₂N-[P₃-C₆H₄]-{N(C₂H₄O)ₐCH₂CH(C₂H₅)OH}₂

H₂N-[P₃-C₆H₄]-{N(C₂H₄O)ₐ[CH₂CH(CH₃)O]ᵦCH₂CH₂OH}₂

H₂N-[P₃-C₆H₄]-{N(C₂H₄O)ₐ[CH₂CH(C₂H₅)O]ᵦCH₂CH₂OH}₂

H₂N-[P₃-C₆H₄]-{N[CH₂CH*CH₃)O]ₐCH₂CH₂OH}₂

H₂N-[P₃-C₆H₄]-{N[CH₂CH(C₂H₅)O]ₐCH₂CH₂OH}₂ wherein a=1-100; b=1-100; and P₃ is selected from CH₃, C₂H₅, n-C₃H₇, n-C₃H₇, n-C₄H₉, OCH₃, or OC₂H₅.

H₂N-[P₃-C₆H₄]-SO₂NH-CH(CH₃)CH₂[OCH(CH₃)CH₂]b(OC₂H₄)a-OP₄

H₂N-[P₃-C₆H₄]-SO₂NH-CH(CH₃)CH₂[OCH(C₂H₅)CH₂]b(OC₂H₄)a-P₄

H₂N-[P₃-C₆H₄]-SO₂NH-CH(C₂H₅)CH₂[OCH(C₂H₅)CH₂]b(OC₂H₄)a-OP₄

H₂N-[P₃-C₆H₄]-SO₂NH-CH(C₂H₅)CH₂[OCH(CH₃)CH₂]b(OC₂H₄)a-OP₄

H₂N-[P₃-C₆H₄]-SO₂NH-CH(CH₃)CH₂[OCH(CH₃)CH₂]a-OP₄

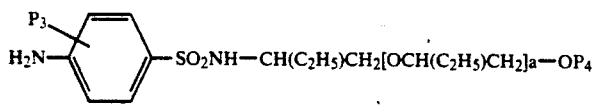
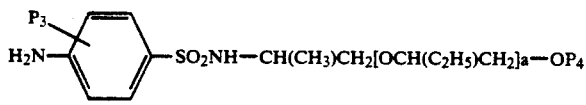
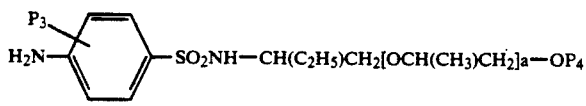
wherein a=1-19; b=2-31; and $P_4$ is selected from $CH_3$, $C_2H_5$, n-$C_3H_7$, n-$C_3H_7$, n-$C_4H_9$, n-$C_5H_{11}$, or n-$C_6H_{11}$ and $P_3$ is recited above.
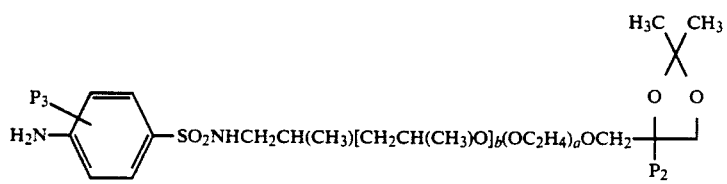
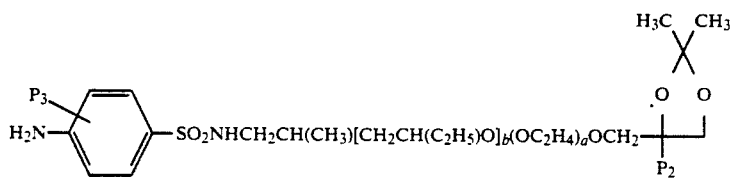
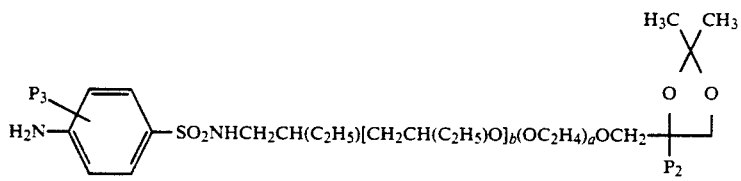
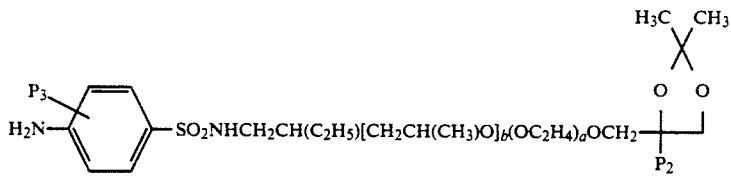
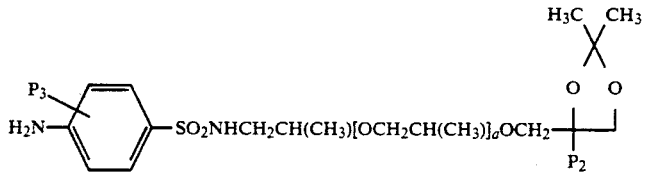
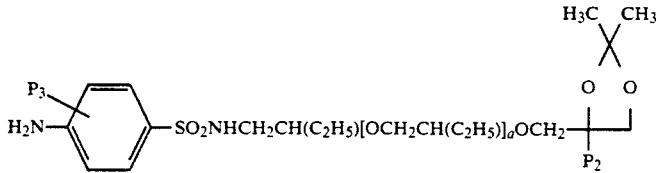

-continued
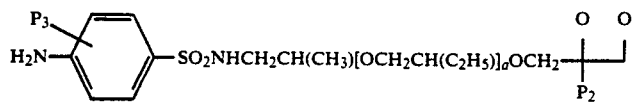
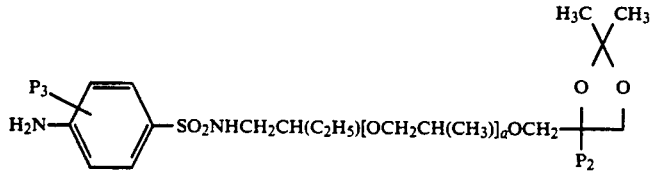
wherein a=1-19; b=2-31; and $P_2$ is selected from hydrogen, $CH_3$, or $C_2H_5$, and $P_3$ is recited above.
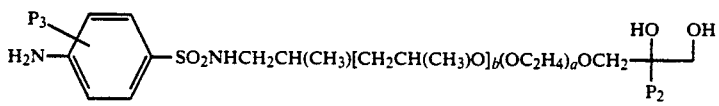
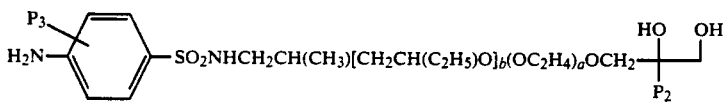
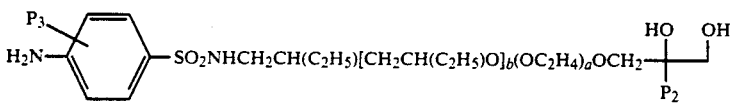
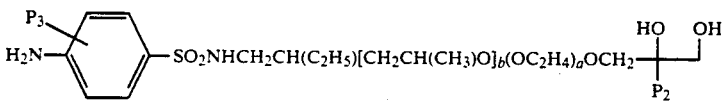
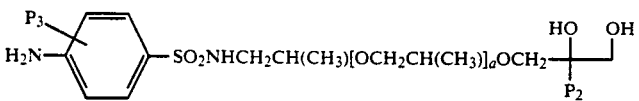
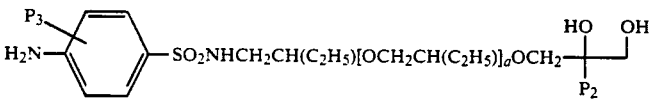
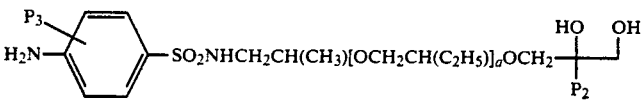
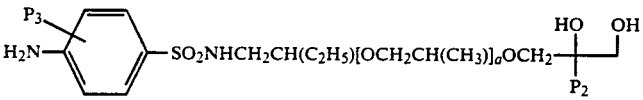
wherein a=1-19; b=2-31; $P_2$ and $P_3$ are recited above.
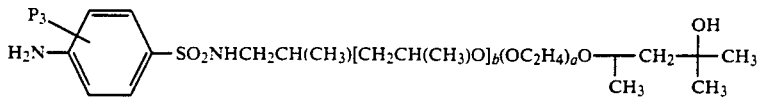

-continued
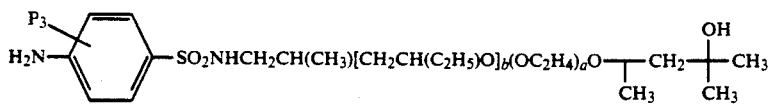
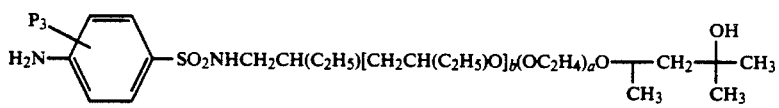
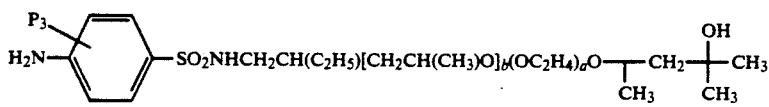
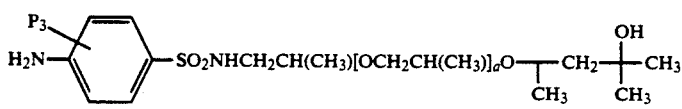
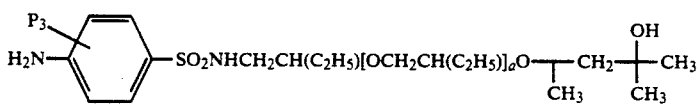
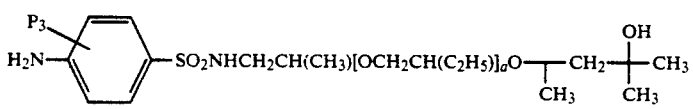
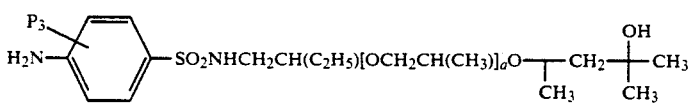
wherein $a=1-19$; and $b=2-31$; wherein $P_3$ is as recited above.
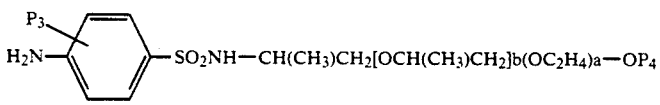
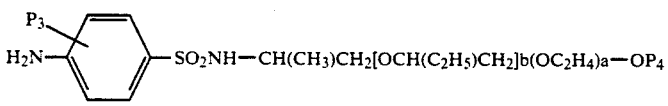
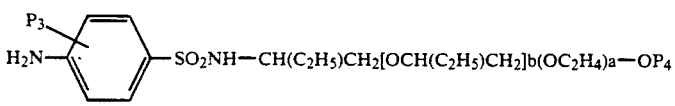
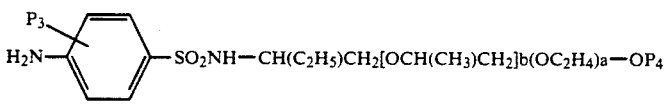
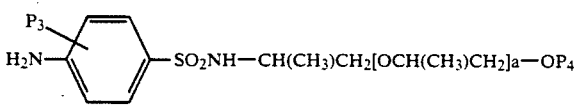
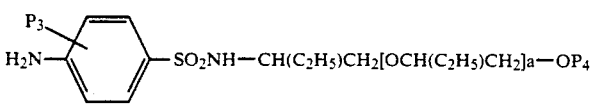

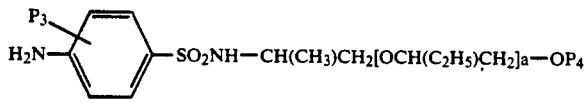
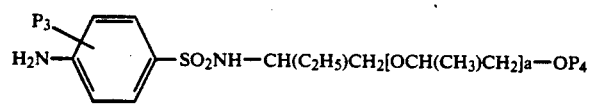
wherein a=4-132; and a+c=2-5; wherein $P_3$ and $P_4$ are recited above.
wherein a=1-19; and b=2-31; wherein $P_3$ and $P_4$ are recited above.
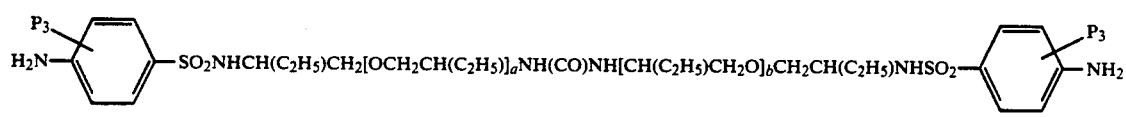
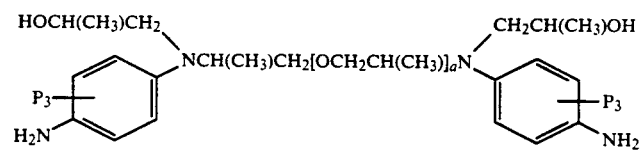
wherein a 2.6; wherein $P_3$ is recited above.
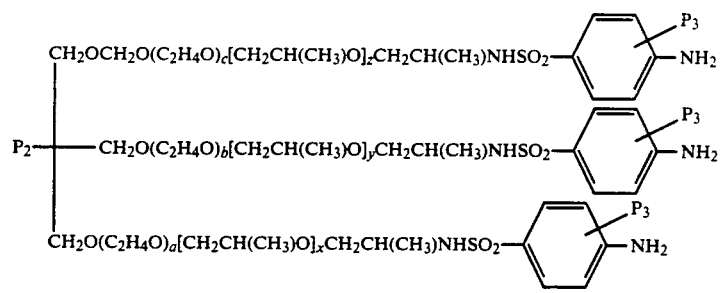
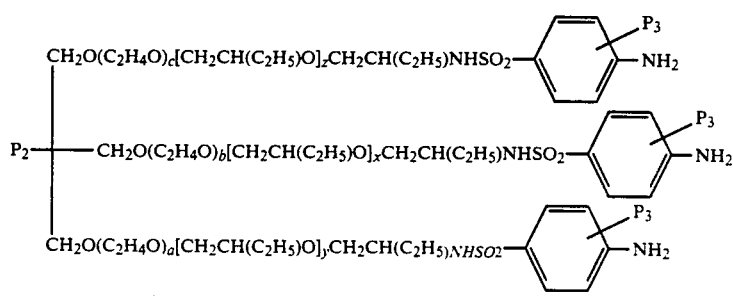

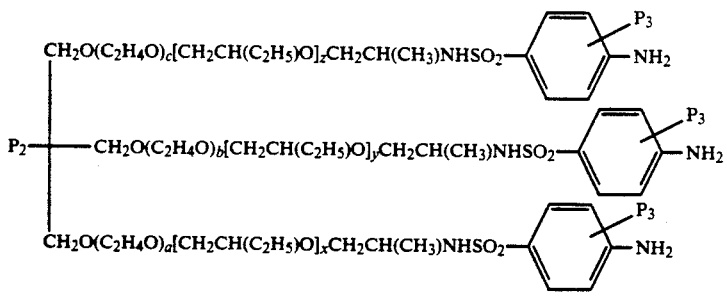
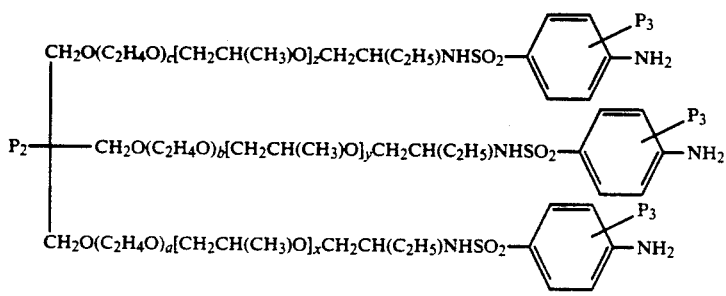
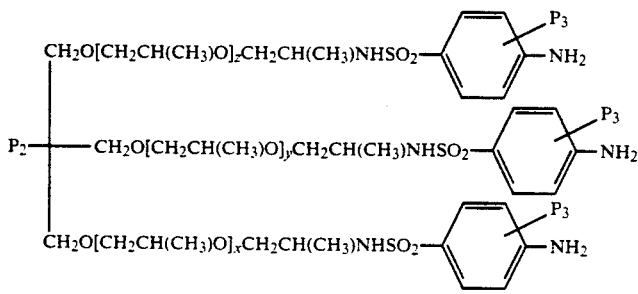
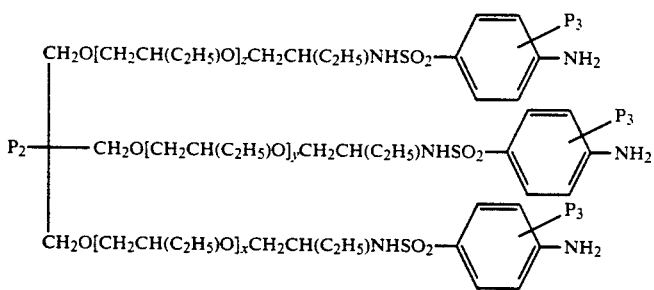
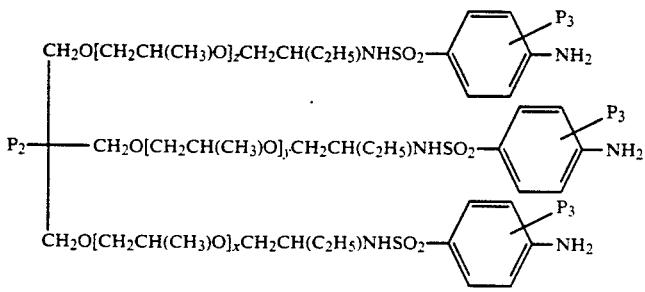

-continued

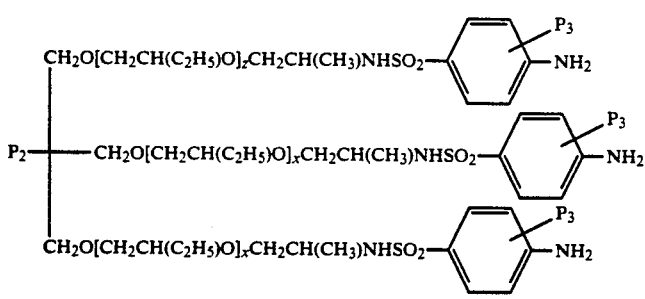

wherein a+b+c=1-80 and x+y+z=5-81; wherein $P_2$ and $P_3$ are recited above.

Thermoplastic resins which may be used according to the present invention include a wide range of resins and synthetic resin compositions which are known in the art as being essentially thermoplastic in nature. The term "thermoplastic" is used herein in its conventional sense to mean a resin "having the property of softening or fusing when heated and of hardening again when cooled" (see Webster's Seventh Collegiate Dictionary, G & C Merriam Co., 1965). Thermoplastic resins are to be clearly distinguished both in terms of their essential physical and chemical characteristics from thermosetting resins. The term "thermosetting" used herein is also used in its conventional sense to means a resin having the property of becoming permanently rigid when heated or cured.

Examples of thermoplastic resin systems which may be employed include a wide range of polyolefin polymers, e.g., polyethylene, linear low density polyethylene, polyproplene, polybutylene, and copolymers made from ethylene, propylene and/or butylene. Other thermoplastic polymers which may be employed according to the present invention include polyvinyl chloride, polyvinylidene chloride, cellulosic resins such as cellulose acetate, cellulose acetate butyrate and cellulose acetate propionate, acrylic resins such as polymethyl methacrylate, styrene acrylonitrile, polystyrene, polycarbonate and acrylonitrile butadiene styrene (therein ABS), polyamides such as nylon 6 and nylon 66 and polyesters such as polyethylene terephthalate, especially glycol modified polyethylene terephthalate and polybutylene terephthalate.

As mentioned above, the colorants may be employed in the thermoplastic resins in a minor amount sufficient to provide the desired degree of coloration in the resin. The actual amount used will, in addition to the desired depth of shade, depend upon the tinctorial strength of the chromophore used and the overall molecular weight of the colorant, e.g., chromophore plus poly(oxyalklene) chain length. Typically the amount of colorant employed may be from about 0.001 percent to about 10 percent, preferably from about 0.001 percent to about 3 percent, and most preferably from about 0.1 to about 1.0 percent by weight based upon the overall weight of the resin composition.

Other conventional additives may also be present in the resin compositions of the present invention. For instance, such additives may include plasticizers, antioxidants, stabilizers, lubricants, flame retardants, nucleating agents and other additives which will be readily identified by those skilled in the art. In general, the colorants have been observed to have little or no adverse interactions with these conventional additives.

Because the colorants if used properly ordinarily do not detract from the clarity of the resin, it has been found that additives which improve the clarity of such resins may be particularly desirable for use in combination with colorants as described herein to provide resin products that are both colored and which also have excellent clarity. One particular class of additives which have been found to be useful in this regard are the benzylidene sorbitols including substituted benzylidene sorbitols such as those described in U.S. Pat. No. 4,016,118 to Hamada, et al. (E. C. Chemical); U.S. Pat. No. 4,371,645 to Mahaffey (Milliken Research Corporation); and Japanese Pat. No. SHO [1977]53-117044 to Kobsyashi, et al. (New Japan Chemical); all of these patents being hereby incorporated herein by reference. The particular shade of the colorant will depend primarily upon the particular chromophore group selected. A large variety of colors and shades may be obtained by blending two or more colorants. Blending the colorants of the present invention can be readily accomplished as the colorants are polymeric materials which may have substantially identical solubility characteristics, which are dictated by the nature of the polymeric chain. Therefore, the colorants are in general soluble in one another, and are also in general completely compatible with each other.

According to the process of the invention, the colorant may be incorporated into the thermoplastic resin using conventional techniques such as those employed to incorporate other additives in such resins. For instance, the colorant may be incorporated into the resin by simply adding it to the resin while the resin is in a plasticized or molten state, typically prior to formation of the polymer into its final shape, e.g., by molding, extrusion, blow-molding and the like. For instance when the thermoplastic resin to be colored is a polyolefin resin the process may be carried out by adding a colorant comprised of a poly(oxyalkylene) substituted chromophore group directly to the molten polymer, by tumbling it onto a pre-extruded pelletized resin, or by mixing it into the resin powder prior to extrusion. The polymer may then be molded or extruded in the usual manner, i.e., in the same way as for polyolefin resins which are not colored. Details about these procedures may be found in the relevant literature.

Alternatively, a concentrate of the colorant in an appropriate resin or vehicle may first be prepared. Such concentrate may contain an appropriately high percentage of colorant. The concentrates may be in the form of liquids, solids, e.g., powders, pellets, etc., as may be desired. These concentrates may then incorporated into the thermoplastic resin as is well understood in the art.

The colorants used in the process and in the composition of the present invention are polymeric colorants which may according to one embodiment be in the liquid phase. Thus, if in the liquid phase, they may be added to the thermoplastic polymer melt in solvent-free form rather than in the form of solutions or dispersions in a suitable solvent or dispersing medium. Obviously, liquids may have certain processing advantages over solids, and moreover liquids may, if desired, be added directly to the molten polymer and therefore contain no extraneous solvent or dispersing agents. This process may, therefore, provide unusual and advantageous properties in the final thermoplastic resin product. Alternatively, however, the colorants may be premixed with minor amounts of or solvent or dispersing agent which is compatible with the resin, thus providing certain processing advantages.

According to the process of the invention, the liquid colorant may be incorporated into the thermosetting resins by simply adding it to the reaction mixture or to one of the components of the reaction mixture before or during the polyaddition reaction. For instance, when the thermosetting resin to be colored is a polyurethane resin the process may be carried out by adding the coloring agent in the form of a liquid to the polyol or even in some instances to the polyisocyanate component of the reaction mixture either before or during polyurethane formation. The subsequent reaction may be carried out in the usual manner, i.e., in the same way as for polyurethane resins which are not colored. Details about this procedure may be found in the relevant literature.

The present coloring agents of one embodiment of the present invention are polymeric, liquid, reactive coloring agents. Thus, they may be added to the reaction mixture or to one of the components thereof in solvent-free form rather than in the form of solutions or dispersions in suitable solvent or dispersing medium. Obviously liquids have significant processing advantages over solids, and moreover liquids of the present invention may, if desired, be added directly to the reaction mixture and therefore contain no extraneous nonreactive solvent or dispersing agent. This process may, therefore, provide unusual and advantageous properties in the final thermoset resin product. Alternatively, however, the coloring agent may be premixed with minor amounts of one or more of the precursors of the polymeric product, thus providing certain processing advantages.

The thermosetting resins to which the process of the present invention may be applied may be made by the reaction of a nucleophile with an electrophile. Examples of such resins include alkyds, allylics, the amines, e.g., melamine and urea, epoxies, phenolics, polyesters, silicones and urethanes. The thermosetting resin colored according to the present invention can be used in a variety of different end uses. e.g., as moldings, sealants, elastomers, films, fibers, lacquers, coating and foamed materials. It has been found in particular that the present colorants may quite advantageously be employed for the production of foams, such as polyurethane foams which may be soft, semi-rigid or rigid foams, or the so-called polyurethane integral skin and microcellular foams. Such foams are useful for producing shaped products by injection molding, extrusion or calendaring and may be obtained by adding the liquid coloring agent to the polyol or diol component of the reaction mixture, or to one of the other components, although addition to the polyol component is preferred. The polyols may be polyesters which contain hydroxyl groups, in particular reaction products of dihydric alcohols and dibasic carboxylic acids, or polyethers which contain hydroxyl groups, in particular products of the addition of ethylene oxide, propylene oxide, styrene oxide or epichlorohydrin to water, alcohols or amines, preferably dialcohols. The colorant may also be admixed with chain extending diols, e.g., ethylene glycol, diethylene glycol and butane diol. In general, it is desirable not to use more than about 20 percent by weight of colorant based on the weight of polyol. In most cases very strong colorations are produced with a small proportion of the colorant, for example, from about 0.1 to about 2 percent, preferably 0.5 to 1 percent by weight colorant based on the weight of polyol.

Because the present colorants are, in themselves, polymeric compounds, they may be soluble, for instance, in most polyols which would be used in polyurethane manufacture, in most epoxy formulations, in polyester formulations and themselves in admixtures. This property may be particularly valuable in that this solubility may permit rapid mixing and homogeneous distribution throughout the resin, thus eliminating shading differences and streaks when properly mixed, the colorant may have no tendency to settle as would be the base with pigment dispersions, and it is possible to prepare a blend of two or more colorants which provides a wide range of color availability.

The present liquid reactive coloring agents may also be of considerable value in reaction injection molding (RIM) applications. The RIM process is a method of producing molded polyurethanes and other polymers wherein the two reactive streams are mixed while being poured into a mold. Upon reaction, the polymer is "blown" by chemicals to produce a foam structure. This process may be hindered by the presence of solid particles, such as conventional pigments. The present invention may not cause this hinderance because there are no particles in the system and the colorant becomes part of the polymer through reaction with one of the components.

The following examples illustrate specific compounds of the present invention and their preparation with the various parts or percentages, unless otherwise stated, being by weight.

The abbreviations EO, PO, and BO refer to —CH$_2$CH$_2$—, —CH(CH$_3$)CH$_2$—, and —CH(C$_2$H$_5$)CH$_2$—, respectively. Also, referring to EXAMPLE #1, the terminology "9PO/1EO-Me" means that the hydroxyl from methyl alcohol has been reacted with at least one ethylene oxide moiety EO, and that each terminal EO has been reacted with an propylene oxide moiety PO being in stoichiometric excess in the reaction system. It is noted that numerical valves assigned to the EO, and PO units of EXAMPLE #1, represent the average of these units per reactive site of the poly(oxyalkylene)amine.

EXAMPLE #1

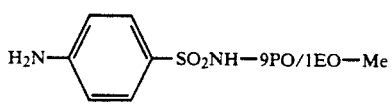

A mixture is prepared by adding 632.5 grams (1.05 mole) of Jeffamine M-600 primary amine with an amine equivalent weight of 1.66 meq/g) to 116.6 grams of sodium carbonate in 2000 ml of water. The mixture is cooled to 10°-15° C. and 233 grams (1 mole) of 4-acetamidobenzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #1A

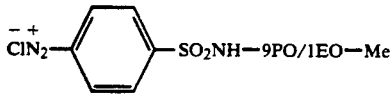

A solution of 94 grams (0.125 mole) of amine 9PO/1EO-Me sulfonamide intermediate of EXAMPLE #1, 45 milliliters concentrated hydrochloric acid, and 90 milliliters of water is added to a 500 milliliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

EXAMPLE #1B

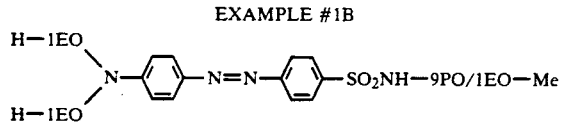

A 2000 ml milliliter beaker equipped with a thermometer, cooling bath, and mechanical stirrer is charged with 24 grams (0.131 mole) of aniline 2EO-H intermediate, 200 grams of water 200 grams of ice and 4 grams of urea. The mixture is cooled to below 0° C. The diazo solution (as prepared in Example #1A) is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #2

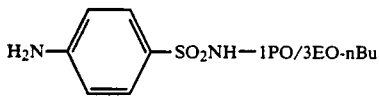

A mixture is prepared by adding 438.9 grams (1.05 mole) of primary amine with an amine equivalent weight of 1.66 meq/g) to 116.6 grams of sodium carbonate in 2000 ml of water. The mixture is cooled to 10°-15° C. and 233 grams (1 mole) of 4-acetamidobenzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #2A

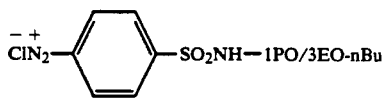

A solution of 73.5 grams (0.125 mole) of amine 1PO/3EO-nBu sulfonamide intermediate of EXAMPLE #2, 45 milliliters concentrated hydrochloric acid, and 90 milliliters of water is added to a 500 milliliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

EXAMPLE #2B

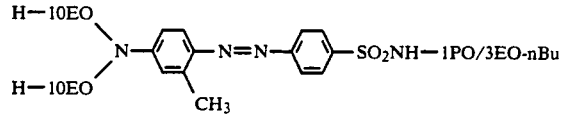

A 1000 ml milliliter beaker equipped with a thermometer, cooling bath, and mechanical stirrer is charged with 129.3 grams (0.131 mole) of m-toluidine 20EO-H intermediate, 200 grams of water, 200 grams of ice and 4 grams of urea. The mixture is cooled to below 0° C. The diazo solution (as prepared in Example #2A) is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #3

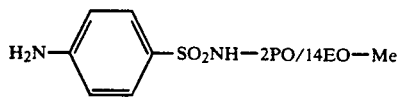

A mixture is prepared by adding 777 grams (1.05 mole) of primary amine with an amine equivalent weight of 1.35 meq/g) 116.6 grams of sodium carbonate in 2000 ml of water. The mixture is cooled to 10°-15° C. and 233 grams (1 mole) of 4-acetamido-benzenesulfonyl chloride are added to the mixture over one half hour.

After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #3A

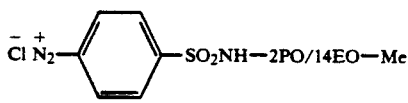

A solution of 113.9 grams (0.125 mole) of amine 2PO/14EO-Me sulfonamide intermediate of Example #3, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

EXAMPLE #3B

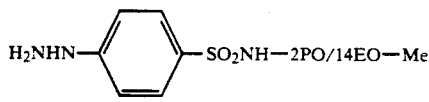

A solution of 113.9 grams (0.125 mole) of amine 2PO/14EO-Me sulfonamide intermediate of Example #3A, 45 milliters concentrated hydrochloric acid, and 90 milliters of water is added to a 500 milliter flask and cooled to 0°-5° C. Ten grams of sodium nitrite are added maintaining the mixture below 10° C. After several hours, the excess nitrite is destroyed with sulfamic acid. The diazo solution is then dripped into a solution of 94 grams of sodium sulfite in 250 grams of water, stirred for one hour at room temperature and then 50 grams of concentrated sulfuric acid are added and the mixture heated for one hour at 100° C. After cooling, the pH is adjusted with sodium hydroxide to 10. The organic layer is separated and extracted into methylene chloride. The methylene chloride solution is separated from the salt water solution, further washed several times with water to a neutral pH, and dried over anhydrous magnesium sulfate. The dried solution is filtered and stripped under reduced pressure at 90° C. to yield a liquid intermediate.

EXAMPLE #3C

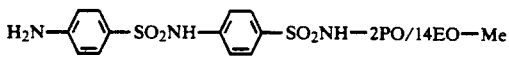

A mixture is prepared by adding 911 grams (1 mole) of the amino 2PO/14EO-Me sulfonamide intermediate of Example #3 to 122 grams sodium carbonate in 1000 ml of water. The mixture is cooled to 10°-15° C. and 233 grams (1 mole) of 4-acetamido-benzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #3D

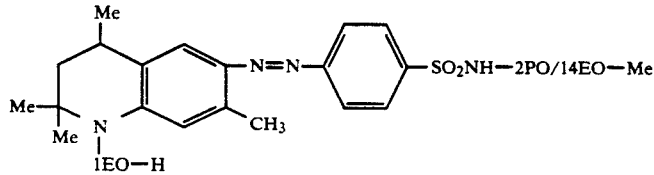

A 2000 ml milliliter beaker equipped with a thermometer, cooling bath, and mechanical stirreris charged with 30.5 grams (0.131 mole) of 2,2,4,7-tetramethyl-1,2,3,4-tetrahydroquinoline 1EO-H intermediate, 300 grams of water, 300 grams of ice and 8 grams of urea. The mixture is cooled to below 0° C. The diazo solution (as prepared in Example #3A) is added dropwise to the beaker over about 30 minute, maintaining he temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #3E

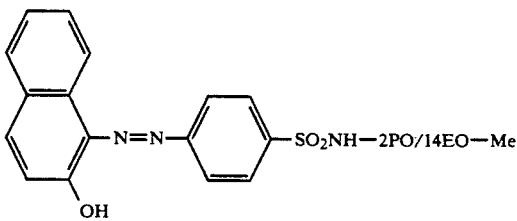

A 2000 ml milliliter beaker equipped with a thermometer, cooling bath, and mechanical stirrer is charged with 200 grams of water, 29.2 grams of 50 percent sodium hydroxide and 31.7 grams (0.22 mole) of 2-naphthol. The mixture is cooled to below 5° C. The diazo solution (as prepared in EXAMPLE #3A) is added slowly dropwise to the beaker, maintaining the temperature below 5° C. and the pH is kept in the range of 4–7 with caustic. The resulting mixture is stirred for three hours for post coupling. At the end of this period, the pH is adjusted to 7.0 with dilute hydrochloric acid keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid with a maximum absorbance at 483 nm.

EXAMPLE #3F

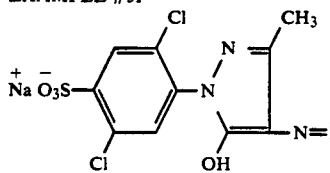

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 75.7 grams (0.22 mole) of 1-(2',5'-dichloro-4'-sulfophenyl)-3-methyl-5-pyrazolone. The mixture is cooled to below 5° C. The diazo solution (as prepared in Example #3A) is added slowly dropwise to the beaker, maintaining the temperature below 5° C. and the pH is kept in the range of 4–7 with Versene. A total of 148 additional grams of Versene are used. When the addition is complete, the resulting mixture is stirred for three hours for post coupling. At the end of this period, the pH is adjusted to 8.5 with 50 percent sodium hydroxide where the yellow colored layer phase separates from the aqueous salt layer. The yellow product has a maximum absorbance at 402 nm.

EXAMPLE #3G

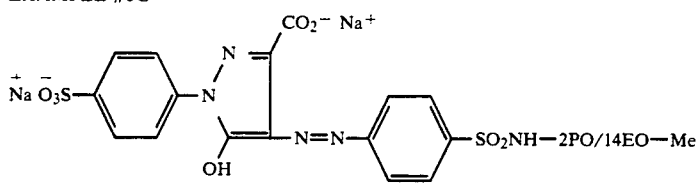

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 71.7 grams (0.22 mole) of 1-(-4'-sulfophenyl)-3-carboxy-5-pyrazolone.

The mixture is cooled to below 5° C. The diazo solution (as prepared in Example #3A) is added slowly dropwise to the beaker, maintaining the temperature below 5° C. and the pH is kept in the range of 4–7 with Versene. When the addition is complete, the resulting mixture is stirred for three hours for post coupling. At the end of this period, the pH is adjusted to 8.5 with 50 percent sodium hydroxide where the yellow colored layer phase separates from the aqueous salt layer. The yellow product has a maximum absorbance at 412 nm.

EXAMPLE #3H

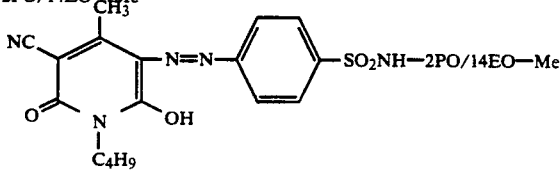

A 2000 ml milliliter beaker equipped with a thermometer, cooling bath, and mechanical stirrer is charged with 200 grams of water, 29.2 grams of 50 percent sodium hydroxide and 20.4 grams (0.22 mole) of pydridone. The mixture is cooled to below 5° C. The of diazo solution (as prepared in EXAMPLE #3A) is added slowly dropwise to the beaker, maintaining the temperature below 5° C. and the pH is kept in the range of 4–7 with caustic. The resulting mixture is stirred for three hours for post coupling. At the end of this period, the pH is adjusted to 7.0 with dilute hydrochloric acid keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a yellow liquid with a maximum absorbance at 431 nm.

EXAMPLE #3I

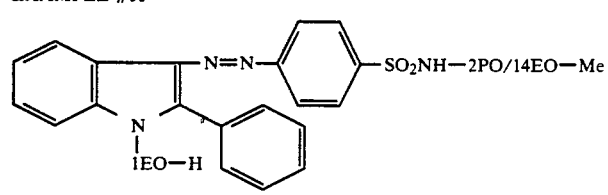

A 2000 ml milliliter beaker equipped with a thermometer, cooling bath, and mechanical stirreris charged with 30.9 grams (0.13 mole) of 2-phenylindole 1EO-H intermediate, 300 grams of water, 300 grams of ice and 4 grams of urea. The mixture is cooled to below 0° C. The diazo solution (as prepared in Example #3A) is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange-yellow liquid.

EXAMPLE #3J

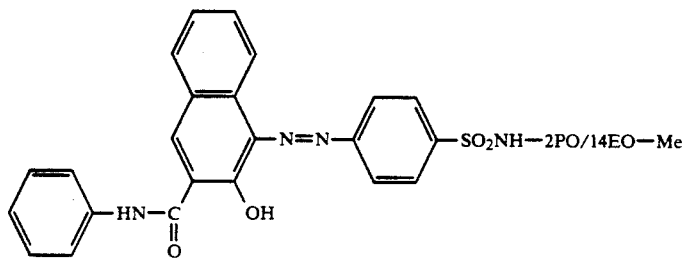

A 2000 ml milliliter beaker equipped with a thermometer, cooling bath, and mechanical stirrer is charged with 300 grams of water, 29.2 grams of 50 percent sodium hydroxide and 57.9 grams (0.22 mole) of Naphthol AS. The mixture is cooled to below 5° C. The diazo solution (as prepared in EXAMPLE #3A) is added slowly dropwise to the beaker, maintaining the temperature below 5° C. and the pH is kept in the range of 4-7 with caustic. The resulting mixture is stirred for three hours for post coupling. At the end of this period, the pH is adjusted to 7.0 with dilute hydrochloric acid keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange liquid with a maximum absorbance at 495 nm.

EXAMPLE #4

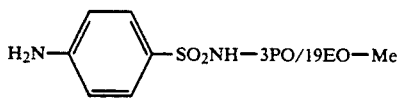

A mixture is prepared by adding 1235.3 grams (1.05 mole) of Jeffamine M-1000 primary amine with an amine equivalent weight of 0.85 meq/g), 116.6 grams of sodium carbonate in 2000 ml of water. The mixture is cooled to 10°-15° C. and 233 grams (1 mole) of 4-acetamidobenzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #4A

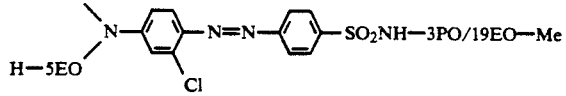

A solution of 168.4 grams (0.125 mole) of amine 3PO/19EO-Me sulfonamide intermediate of Example #4, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

A 2000 ml milliliter beaker equipped with a thermometer, cooling bath, and mechanical stirrer is charged with 75.6 grams (0.13 mole) of m-chloroaniline 10EO-H intermediate, 200 grams of water, 200 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange liquid.

EXAMPLE #5

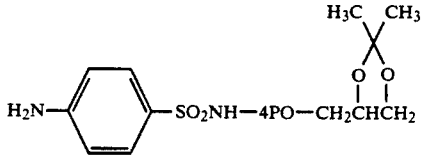

A mixture is prepared by adding 388.5 grams (1.05 mole) of a primary amine with an amine equivalent weight of 2.70 meq/g), 120 grams of sodium carbonate in 2000 ml of water. The mixture is cooled to 10°-15° C. and 233 grams (1 mole) of 4-acetamidobenzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #5A

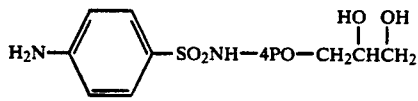

Sixty-four grams (0.12 mole) of the acetal prepared in EXAMPLE #5 are added along with 200 ml of water to a three necked 500 ml flask equipped with overhead stirrer, heating mantle, and Dean-Stark trap. The mixture is heated to 80° C. and 10 grams of 70% sulfuric acid are added. This reaction mixture is maintained at 80° C. until no more acetone can be detected overhead in the trap. The mixture is then cooled and the product was extracted into methylene chloride. The methylene chloride solution was separated, washed several times with water to neutral pH, and dried over anhydrous magnesium sulfate. The dried methylene chloride solution is filtered and stripped under reduced pressure at 90° C. to give a liquid product containing a hydroxyl band in the IR spectrum.

EXAMPLE #5B

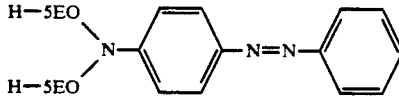

A solution of 62.7 grams (0.125 mole) of amine sulfonamide intermediate of Example #5A, 45 milliliters concentrated hydrochloric acid, and 90 milliliters of water is added to a 500 milliliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

A 2000 ml milliliter beaker equipped with a thermometer, cooling bath, and mechanical stirrer is charged with 590 grams (0.13 mole) of aniline 100EO-H intermediate, 500 grams of water, 500 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange liquid.

EXAMPLE #6

A mixture is prepared by adding 642.2 grams (1.05 mole) of a Jeffamine ED-600 di-primary amine with an amine equivalent weight of 3.27 meq/g) 240 grams of sodium carbonate in 2000 ml of water. The mixture is cooled to 10°-15° C. and 466 grams (2 mole) of 4-acetamidobenzenesulfonyl chloride are added to the mixture over one half hour. After the addition is complete, the mixture is warmed at 50° C. for an additional two hours to insure complete reaction. Eighty grams (2 moles) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #6A

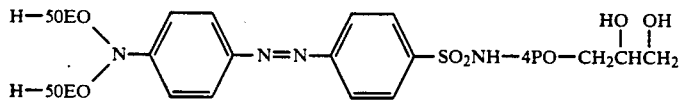 

A solution of 117.2 grams (0.125 mole) of amine 2PO/9EO/2PO disulfonamide intermediate of Example #6, 90 milliters concentrated hydrochloric acid, and 180 milliters of water is added to a 1000 milliter flask and cooled to 0°-5° C. Twenty grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

A 2000 ml milliliter beaker equipped with a thermometer, cooling bath, and mechanical stirrer is charged with 139.9 grams (0.26 mole) of aniline 10EO-H intermediate, 200 grams of water, 200 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #7

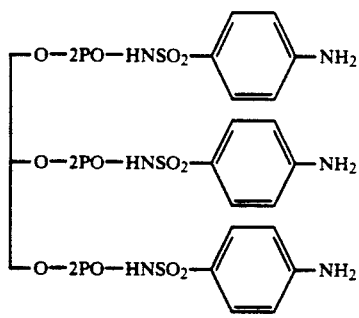

A mixture is prepared by adding 605.7 grams (1.05 mole) of a Jeffamine T-403 tri-primary amine with an amine equivalent weight of 0.52 meq/g) 360 grams of sodium carbonate in 2000 ml of water. The mixture is cooled to 10°-15° C. and 699 grams (3 mole) of 4-acetamidobenzenesulfonyl chloride are added to the mixture over one half hour. After the addition is complete, the mixture is warmed at 50° C. for an additional two hours to insure complete reaction. One hundred twenty grams (3 moles) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #7A

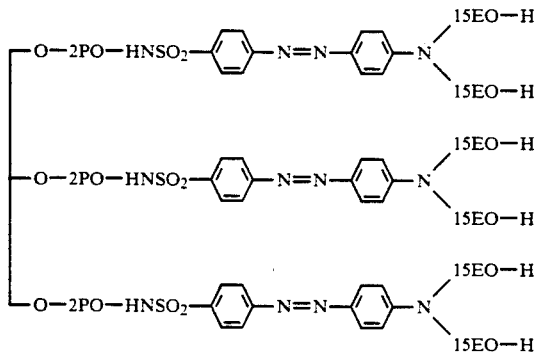

A solution of 135.9 grams (0.125 mole) of amine 6PO trisulfonamide intermediate of Example #7, 120 milliters concentrated hydrochloric acid, and 270 milliters of water is added to a 2000 milliter flask and cooled to 0°-5° C. Thirty grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

A 2000 ml milliliter beaker equipped with a thermometer, cooling bath, and mechanical stirrer is charged with 551 grams (0.39 mole) of aniline 30EO-H intermediate, 500 grams of water, 500 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #8

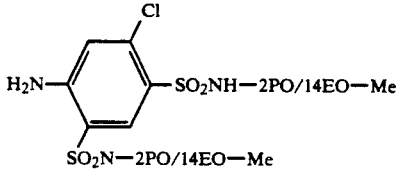

A mixture is prepared by adding 1555.6 grams (2.1 moles) of primary amine with an amine equivalent weight of 1.35 meq/g) 240 grams of sodium carbonate in 2000 ml of water. The mixture is cooled to 10°-15° C. and 233 grams (1 mole) of 3-chloro-2,4-dichlorosulfonylaniline are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #8A

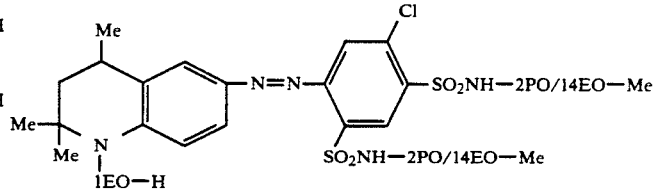

A solution of 220.6 grams (0.125 mole) of amine 2PO/14EO disulfonamide intermediate of Example #8, 80 milliters concentrated hydrochloric acid, and 180 milliters of water is added to a 1000 milliter flask and cooled to 0°-5° C. Twenty grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour. At this point the diazo intermediate is ready for further use.

A 2000 ml milliliter beaker equipped with a thermometer, cooling bath, and mechanical stirrer is charged with 57.5 grams (0.26 mole) of 2,2,4-trimethyl-1,2,3,4-tetrahydroquinone 1EO-H intermediate, 200 grams of water, 200 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

70% sulfuric acid are added. This reaction mixture is maintained at 80° C. until no more acetone could be detected overhead in the trap. The mixture is then cooled and the product is extracted into methylene chloride. The methylene chloride solution is separated, washed several times with water to neutral pH, and dried over anhydrous magnesium sulfate. The dried methylene chloride solution is filtered and stripped under reduced pressure at 90° C. to give a liquid product containing a hydroxyl band in the IR spectrum.

EXAMPLE #9B

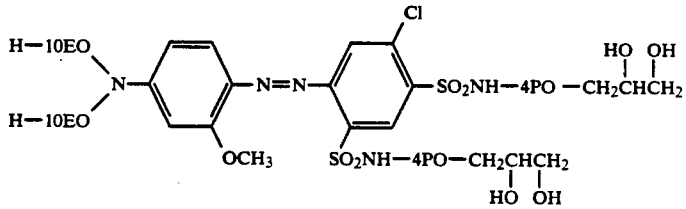

EXAMPLE #9

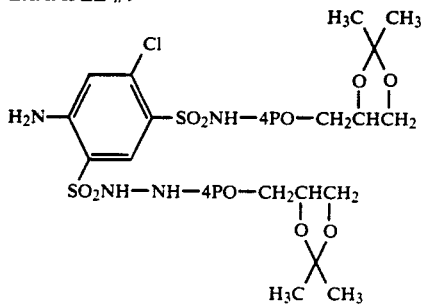

A mixture is prepared by adding 777 grams (2.1 moles) of primary amine with an amine equivalent weight of 2.70 meq/g), 240 grams of sodium carbonate in 2000 ml of water. The mixture is cooled to 10°–15° C. and 233 grams (1 mole) of 3-chloro-2,4-dichlorosulfonylaniline are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #9A

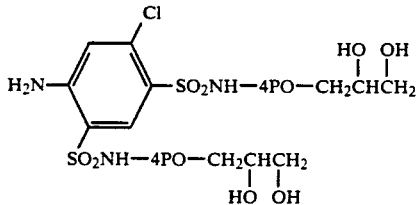

One hundred ten grams (0.12 mole) of the acetal prepared in EXAMPLE #9 are added along with 300 ml of water to a three necked 500 ml flask equipped with overhead stirrer, heating mantle, and Dean-Stark trap. The mixture is heated to 80° C. and 20 grams of A solution of 114.3 grams (0.125 mole) of amine disulfonamide intermediate of Example #9A, 90 milliters concentrated hydrochloric acid, and 180 milliters of water is added to a 1000 milliter flask and cooled to 0°–5° C. Twenty grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 1000 ml milliliter beaker equipped with a thermometer, cooling bath, and mechanical stirrer is charged with 132 grams (0.13 mole) of m-anisidine 20EO-H intermediate, 200 grams of water, 200 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

EXAMPLE #10

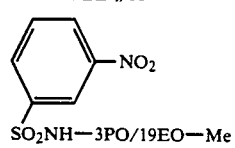

A mixture is prepared by adding 1235.3 grams (1.05 mole) of Jeffamine M-1000 primary amine with an amine equivalent weight of 0.85 meq/g), 259.8 grams of sodium carbonate in 2000 ml of water. The mixture is cooled to 10°–15° C. and 221 grams (1 mole) of m-nitrobenzenesulfonyl chloride are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield the intermediate.

EXAMPLE #10A

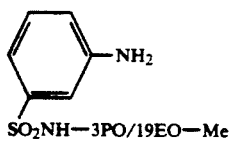

In a 2000 milliter autoclave are charged 681 grams (0.5 moles) of nitro 2PO/19PO-Me sulfonamide intermediate of Example #10, 1000 milliters of ethyl alcohol and 65 grams of wet Raney nickel catalyst. The autoclave is then purged three times with hydrogen gas and heated to 85°-90° C. at a pressure of about 1300 psi. After about two hours the hydrogen uptake ceases. A sample is removed and vacuum stripped of solvent. The IR spectrum of this sample shows no nitro bands and the presence of an amine band indicating that the reaction is complete. The autoclave is cooled and vented. The product is isolated by filtering the reaction mixture and stripping away the solvent under reduced pressure.

EXAMPLE #10B

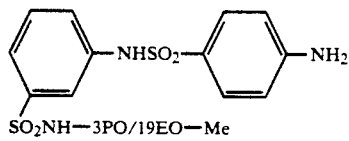

A mixture is prepared by adding 1332 grams (1 mole) of the amino 2PO/19EO-Me sulfonamide intermediate of Example #10A to 122 grams sodium carbonate in 2000 ml of water. The mixture is cooled to 10°-15° C. and 233 grams (1 mole) of 4-acetamidobenzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield the intermediate.

EXAMPLE #10C

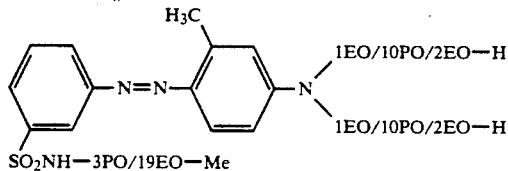

A solution of 166.5 grams (0.125 mole) of amine 3PO/19EO-Me sulfonamide intermediate of Example #10A, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 162.8 grams (0.13 mole) of m-toluidine 2EO/2-0PO/4EO-H intermediate, 200 grams of water, 200 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #11

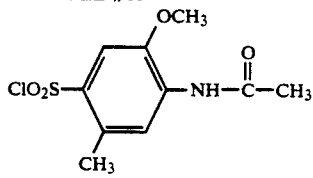

One hundred forty-seven grams (1.07 moles) of 2-methoxy-5-methylaniline, and 250 grams of toluene are charged into a two liter, three necked round bottomed flask equipped with thermometer, mechanical stirrer, heating mantle, and nitrogen (inlet/outlet). This slurry is heated to 80° C. where a homgeneous solution is results. One hundred thirteen grams (1.1 moles) of acetic anhydride are slowly added through an addition funnel to avoid violent exotherms. Upon completion of acetic anhydride addition, the temperature is increased to 95° C. for one hour. The temperature is then increased to 110° C. where the toluene and excess anhydride are removed under reduced pressure. The mixture is cooled to 100° C. and is poured slowly into cold water to precipitate the acetylated intermediate. The crystalline product (acetamido-2-methoxy-5-methylbenzene) is collected and washed with water on a sintered glass filter.

Three hundred ninety grams of chlorosulfonic acid are charged to a three liter, three necked, round bottomed flask equipped with mechanical stirrer, nitrogen (inlet/outlet), and ice bath.

Upon cooling to 15° C., 150 grams (0.84 mole) of acetamido-2-methoxy-5-methylbenzene are slowly added over 2 hours maintaining the temperature below 30° C. Upon complete addition of the acetylated material, the temperature is increased to 50° C. for one hour. At the end of the one hour reaction period, the reaction solution is quenched by slowly poured into ice water. The product is taken up in methylene chloride in a separatory funnel where is washed repeatedly with dilute sodium carbonate solution. The methylene chloride is then evaporated to dryness to yield the gray 4-acetamido-5-methoxy-2-methylbenzene sulfonyl chloride intermediate.

EXAMPLE #11A

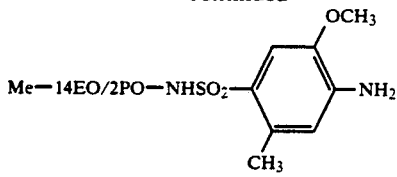

the pH is kept in the range of 4–7 with Versene. When the addition is complete, the resulting mixture is stirred for three hours for post coupling. At the end of this period, the pH is adjusted to 8.5 with 50 percent sodium hydroxide where the red colored layer phase separates from the aqueous salt layer. The red product has a maximum absorbance at 497 nm.

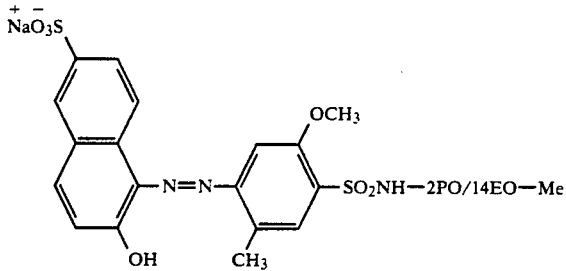

A mixture is prepared by adding 740 grams (1.05 mole) of primary amine with an amine equivalent weight of 1.35 meq/g) 120 grams of sodium carbonate in 2000 ml of water. The mixture is cooled to 10°–15° C. and 278 grams (1 mole) of 4-acetamido-5-methoxy-2-methylbenzene sulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #11B

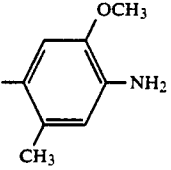

A solution of 117.5 grams (0.125 mole) of amine 2PO/14EO-Me sulfonamide intermediate of Example #11A, 45 milliters concentrated hydrochloric acid, and 90 milliters of water is added to a 500 milliter flask and cooled to 0°–5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 53.9 grams (0.22 mole) of 2-hydroxynaphthalene-6-sulfonic acid. The mixture is cooled to below 5° C. The diazo solution is added slowly dropwise to the beaker, maintaining the temperature below 5° C. and A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 75.7 grams (0.22 mole) of 1-(2′,5′-dichloro-4′-sulfophenyl)-3-methyl-5-pyrazolone. The mixture is cooled to below 5° C. The diazo solution (as prepared in Example #11B) is added slowly dropwise to the beaker, maintaining the temperature below 5° C. and the pH is kept in the range of 4–7 with Versene. When the addition is complete, the resulting mixture is stirred for three hours for post coupling. At the end of this period, the pH is adjusted to 8.5 with 50 percent sodium hydroxide where the yellow colored layer phase separates from the aqueous salt layer. The yellow product has a maximum absorbance at 431 nm.

EXAMPLE #12

Me—19EO/3PO—NHSO₂—[benzene ring with OCH₃, CH₃, NH₂]

A mixture is prepared by adding 1235.3 grams (1.05 mole) of Jeffamine M-1000 primary amine with an amine equivalent weight of 0.85 meq/g), 120 grams of sodium carbonate in 2000 ml of water. The mixture is cooled to 10°–15° C. and 278 grams (1 mole) of 4-acetamido-5-methoxy-2-methylbenzene sulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield the intermediate.

EXAMPLE #12A

-continued

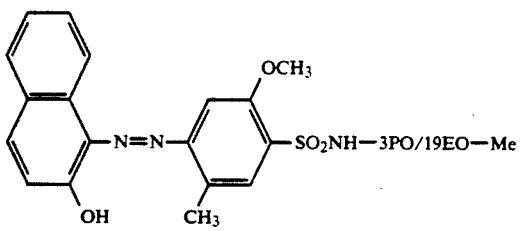

A solution of 165.8 grams (0.125 mole) of amine 3PO/19EO-Me sulfonamide intermediate of Example #12, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 200 grams of water, 29.2 grams of 50 percent sodium hydroxide and 31.7 grams (0.22 mole) of 2-naphthol. The mixture is cooled to below 5° C. The diazo solution is added slowly dropwise to the beaker, maintaining the temperature below 5° C. and the pH is kept in the range of 4-7 with caustic. The resulting mixture is stirred for three hours for post coupling. At the end of this period, the pH is adjusted to 7.0 with dilute hydrochloric acid keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a orange liquid.

EXAMPLE #13

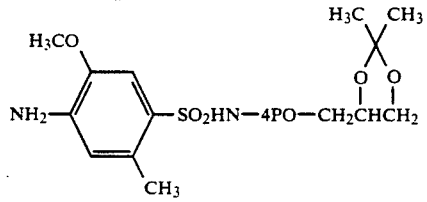

A mixture is prepared by adding 352.17 grams (1.05 mole) of a primary amine with an amine equivalent weight of 2.70 meq/g), 120 grams of sodium carbonate in 2000 ml of water. The mixture is cooled to 10°-15° C. and 278 grams (1 mole) of 4-acetamido-5-methoxy-2-methylbenzene sulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #13A

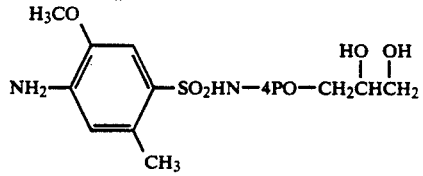

Sixty-eight grams (0.12 mole) of the acetal prepared in Example #13 are added along with 200 ml of water to a three necked 500 ml flask equipped with overhead stirrer, heating mantle, and Dean-Stark trap. The mixture is heated to 80° C. and 10 grams of 70% sulfuric acid are added. This reaction mixture was maintained at 80° C. until no more acetone can be detected overhead in the trap. The mixture is then cooled and the product is extracted into methylene chloride. The methylene chloride solution is separated, washed several times with water to neutral pH, and dried over anhydrous magnesium sulfate. The dried methylene chloride solution is filtered and stripped under reduced pressure at 90° C. to give a liquid product containing a hydroxyl band in the IR spectrum.

EXAMPLE #13B

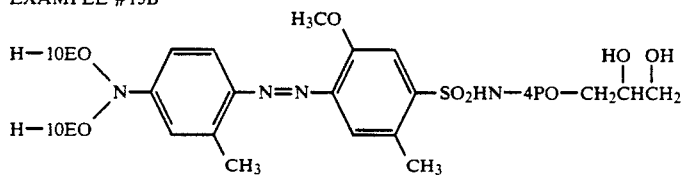

A solution of 66.25 grams (0.125 mole) of amine sulfonamide intermediate of Example #13A, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 128.3 grams (0.13 mole) of m-toluidine 20EO-H intermediate, 200 grams of water, 200 grams of ice and 4 grams of urea. The mixture is cooled to below 0° C. The diazo solution is added dropwise to the beaker over about 30 minutes, maintaining the temperature below 5° C. The resulting mixture is stirred for several hours and allowed to stand overnight, after which 50% sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange liquid.

EXAMPLE #14

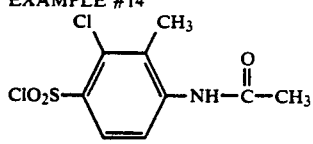

Two hundred two grams (1.43 moles) of 3-chloro-2-methylaniline, and 250 grams of toluene are charged into a two liter, three necked round bottomed flask equipped with thermometer, mechanical stirrer, heating mantle, and nitrogen (inlet/outlet). This slurry is heated to 80° C. where a homogeneous solution is results. One hundred sixty grams (1.5 moles) of acetic anhydride are slowly added through an addition funnel to avoid violent exotherms. Upon completion of acetic anhydride addition, the temperature is increased to 95° C. for one hour. The temperature is then increased to 110° C. where the toluene and excess anhydride are removed under reduced pressure. The mixture is cooled to 100° C. and is poured slowly into cold water to precipitate the acetylated intermediate. The crystalline product (1-acetamido-3-chloro-2-methylbenzene) is collected and washed with water on a sintered glass filter.

Four hundred eighty-two grams of chlorosulfonic acid are charged to a three liter, three necked, round bottomed flask equipped with mechanical stirrer, nitrogen (inlet/outlet), and ice bath.

Upon cooling to 15° C., 126 grams (0.69 mole) of 1-acetamido-3-chloro-2-methylbenzene are slowly added over 2 hours maintaining the temperature below 30° C. Upon complete addition of the acetylated material, the temperature is increased to 50° C. for one hour. At the end of the one hour reaction period, the reaction solution is quenched by slowly poured into ice water. The product is taken up in methylene chloride in a separatory funnel where it is washed repeatedly with dilute sodium carbonate solution. The methylene chloride is then evaporated to dryness to yield the 4-acetamido-2-chloro-3-methylbenzene sulfonyl chloride intermediate.

EXAMPLE #14A

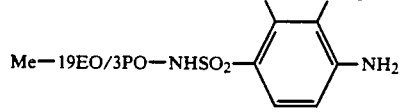

A mixture is prepared by adding 1235.3 grams (1.05 mole) of Jeffamine M-1000 primary amine with an amine equivalent weight of 0.85 meq/g, to 120 grams of sodium carbonate in 2000 ml of water. The mixture is cooled to 10°-15° C. and 282 grams (1 mole) of 4-acetamido-2-chloro-3-methylbenzenesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield the intermediate.

EXAMPLE #14B

A solution of 172.5 grams (0.125 mole) of amine sulfonamide 3PO/19EO-Me intermediate of Example #14A, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 53.9 grams (0.22 mole) of 2-hydroxynaphthalene-6-sulfonic acid. The mixture is cooled to below 5° C. The diazo solution is added slowly dropwise to the beaker, maintaining the temperature below 5° C. and the pH is kept in the range of 4–7 with Versene. When the addition is complete, the resulting mixture is stirred for three hours for post coupling. At the end of this period, the pH is adjusted to 8.5 with 50 percent sodium hydroxide where the orange-red colored layer phase separates from the aqueous salt layer.

EXAMPLE #14C

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 75.7 grams (0.22 mole) of 1-(2',5'-dichloro-4'-sulfophenyl)-3-methyl-5-pyrazolone. The mixture is cooled to below 5° C. the of diazo solution (as prepared in EXAMPLE #14B) is added slowly dropwise to the beaker, maintaining the temperature below 5° C. and the pH is kept in the range of 4–7 with Versene. When the addition is complete, the resulting mixture is stirred for three hours for post coupling. At the end of this period, the pH is adjusted to 8.5 with 50 percent sodium hydroxide where the yellow colored layer phase separates from the aqueous salt layer. The yellow product has a maximum absorbance at 393 nm.

EXAMPLE #15

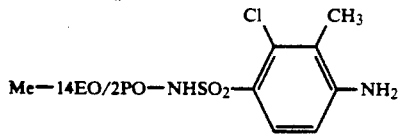

A mixture is prepared by adding 777.8 grams (1.05 mole) of primary amine with an amine equivalent weight of 1.35 meq/g) to 259.8 grams of sodium carbonate in 2000 ml of water. The mixture is cooled to 10°–15° C. and 282 grams (1 mole) of 4-acetamido-2-chloro-3-methylbenzenesulfonyl chloride are added to the mixture over one half hour. After the addition is complete, the mixture is warmed at 50° C. for an additional two hours to insure complete reaction. forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #15A

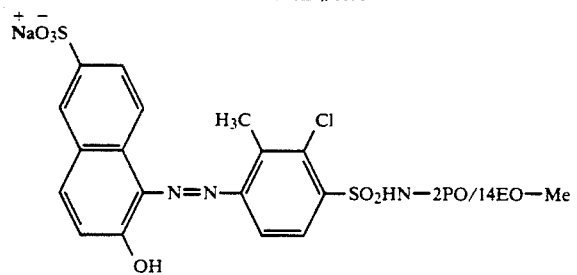

A solution of 117.8 grams (0.125 mole) of amine sulfonamide 2PO/14EO-Me intermediate of Example #15, 45 milliliters concentrated hydrochloric acid, and 90 milliliters of water is added to a 500 milliliter flask and cooled to 0°–5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 53.9 grams (0.22 mole) of 2-hydroxynaphthalene-6-sulfonic acid. The mixture is cooled to below 5° C. The diazo solution is added slowly dropwise to the beaker, maintaining the temperature below 5° C. and the pH is kept in the range of 4–7 with Versene. When the addition is complete, the resulting mixture is stirred for three hours for post coupling. At the end of this period, the pH is adjusted to 8.5 with 50 percent sodium hydroxide where the orange-red colored layer phase separates from the aqueous salt layer.

EXAMPLE #16

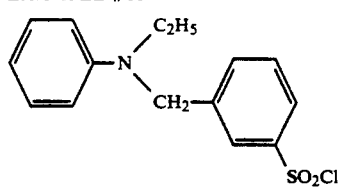

Five hundred thirty-two grams of chlorosulfonic acid are charged to a three liter, three neck, round bottomed flask equipped with mechanical stirrer, nitrogen (inlet/outlet), and ice bath.

Upon cooling to 20° C., 211 grams (1.0 mole) of N-ethyl-N-benzylaniline is slowly added over 1 hour maintaining the temperature below 30° C. Upon complete addition of the aniline compound, the temperature is increased to 55°–60° C. for one hour, and held at 100°–120° C. for four hours. Afterwards, the reaction solution is quenched by slowly poured into ice water. The product is taken up in methylene chloride in a separatory funnel where is washed repeatedly with dilute sodium carbonate solution. The methylene chloride is then evaporated to dryness to yield the pale green solid N-ethyl-N-benzylanilinesulfonyl chloride intermediate.

EXAMPLE #16A

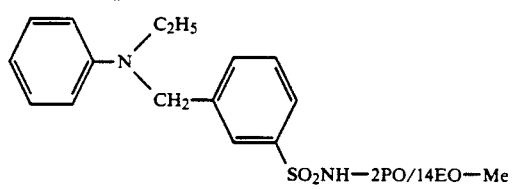

A mixture is prepared by adding 777 grams (1.05 mole) of primary amine with an amine equivalent weight of 1.35 meq/g) 120 grams of sodium carbonate in 2000 ml of water. The mixture is cooled to 10°–15° C. and 309 grams (1 mole) of N-ethyl-N-benzylanilinesulfonyl chloride are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #16B

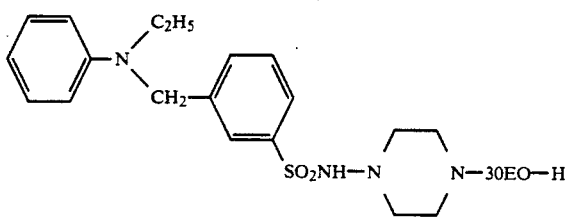

In a 1 gallon autoclave are charged 665 grams (1 mole) of the sulfonamide 1EO-H intermediate and 5 grams of potassium hydroxide catalyst. The reactor is purged three times to 60 psi with nitrogen and is then heated to 250° F. under 5 psi nitrogen pressure.

Next, 1276 grams (29 moles) of ethylene oxide (EO) are added at a rate to maintain a vapor pressure reading less than 80 psi. After the EO addition, the reaction mixture is post-heated at 120° C. for 2 hours.

After vacuum stripping at 200° F. for 15 minutes, the 30EO-H sulfonamide has an average gram molecular weight of 1985 and is ready for use.

EXAMPLE #16C

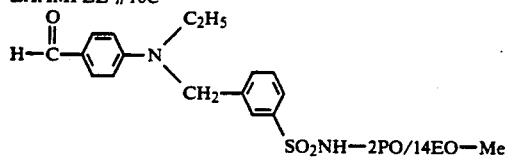

SO₂NH—2PO/14EO—Me

A dry 2000 ml three-neck flask is charged with 181 grams N,N-dimethylformamide under nitrogen and cooled to 0° C. One hundred ninety-two grams of phosphorous oxychloride are added dropwise with mechanical stirring and cooling over one hour. The resulting mixture is stirred for an additional two hours at 0°–5° C. Then 1104 grams (1 mole) of 2PO/14EO-Me sulfonamide intermediate (of Example #16a) are added dropwise. The reaction mixture is gradually heated to 90° C. and held at this temperature for an additional two hours to insure complete reaction. After cooling, the mixture is diluted with an equal amount of ice and 2.5 moles of sodium hydroxide (50 percent by weight). The resulting mixture is heated to 50°–60° C. until the formylated sulfonamide intermediate is hydrolyzed. The resulting mixture is then neutralized with acetic acid and the product extracted into methylene chloride. The methylene chloride layer is phase separated and dried over anhydrous magnesium sulfate. The methylene chloride solution is filtered and the solvent is removed by reduced vacuum at 90° C. An IR spectrum of the resulting liquid product displays the presence of characteristic carbonyl absorbance of the corresponding formyl intermediate.

One hundred thirteen grams of aldehyde (0.1 mole) from Example #16C, 11.3 grams of ethyl cyanoacetate (0.1 mole), two drops of piperidine catalyst and 300 milliliters of toluene are charged into a 500 milliliter three necked flask equipped with thermometer, reflux condenser, Dean-Stark trap, mechanical stirrer, and heating mantle. This mixture is heated at reflux until no more water condenses in the trap which takes about four hours. The resulting mixture is dissolved in methylene chloride and washed with water three times. The resulting methylene chloride solution is then dried over magnesium sulfate and filtered into a 500 milliliter round bottom flask. The solution is then stripped of all volatiles under reduced vacuum to give a yellow liquid.

EXAMPLE #16E

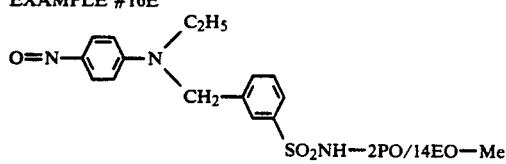

SO₂NH—2PO/14EO—Me

A mixture is prepared by charging 1104 grams (1 mole) of 2PO/14EO-Me sulfonamide intermediate (of EXAMPLE #16A), along with 400 ml of concentrated hydrochloric acid and 100 ml of water in a 3000 ml three neck flask. The mixture is stirred mechanically and cooled to 0° C. A solution of 76 grams (1.1 moles) of sodium nitrite dissolved in 300 ml of water is then added dropwise over one and a half hours maintaining the temperature below 0° C. The mixture is allowed to warm to room temperature and stirred for an additional two hours. The excess nitrite is then destroyed by pulling a vacuum for an additional 30 minutes. After cooling to 0° C., the mixture is neutralized with dilute sodium hydroxide solution and the product extracted into methylene chloride. The methylene chloride layer is phase separated and dried over anhydrous magnesium sulfate. The methylene chloride solution is filtered and the solvent is removed by reduced vacuum at 90° C. An IR spectrum of the resulting liquid product displays a

EXAMPLE #16D

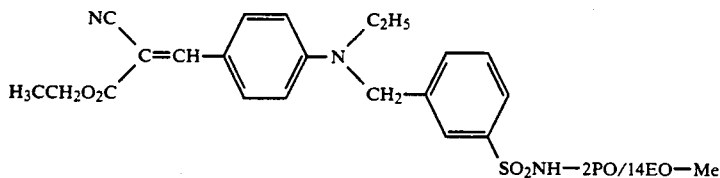

SO₂NH—2PO/14EO—Me characteristic nitroso absorbance.

EXAMPLE #16F

-continued

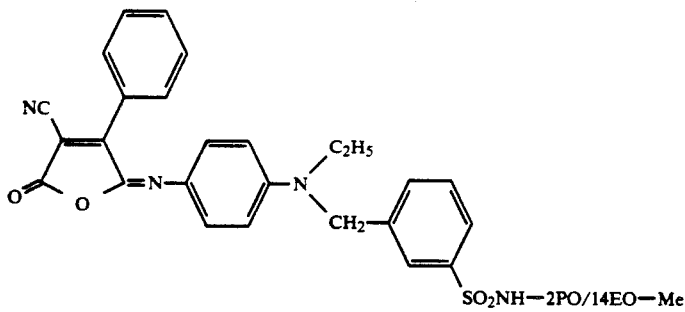

One hundred thirteen grams of nitrosoaniline 2PO/14EO-Me sulfonamide intermediate (0.1 mole from EXAMPLE #16E), 18.5 grams of 3-cyano-4-phenyl-2-(5H)-furanone and 300 milliters of toluene are charged into a 500 milliter three necked flask equipped with thermometer, reflux condenser, Dean-Stark trap, mechanical stirrer, and heating mantle. This mixture is heated at reflux until no more water condenses in the trap which takes about four hours. The resulting mixture is dissolved in methylene chloride and is washed with water three times. The resulting methylene chloride solution is then dried over magnesium sulfate and filtered into a 500 milliter round bottom flask. The solution is then stripped of all volatiles under reduced pressure to give a blue violet liquid.

EXAMPLE #16G

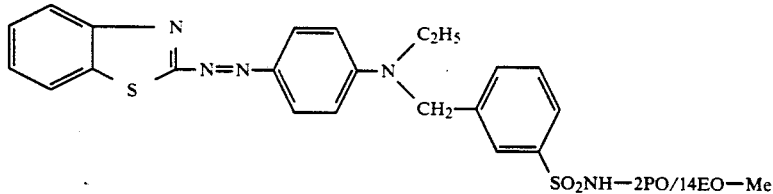

One hundred eighty grams acetic acid, 41 grams propionic acid, and 4 drops of 2-ethyl hexanol defoamer are added to a 500 milliliter three necked flask equipped with a thermometer, cooling bath, and mechanical stirrer. The mixture is cooled and 15.0 grams (0.1 mole) of 2-aminobenzothiazole are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 milliliter beaker is charged with 121 grams (0.11 mole) of 2PO/14EO-Me sulfonamide intermediate from EXAMPLE #16A, 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

EXAMPLE #16H

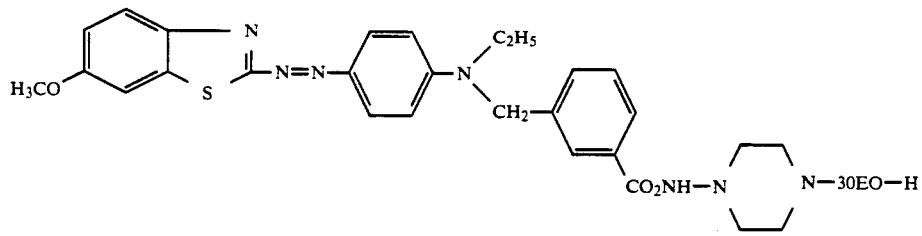

One hundred eighty grams acetic acid, 41 grams propionic acid, and 4 drops of 2-ethyl hexanol defoamer are added to a 500 milliliter three necked flask equipped with a thermometer, cooling bath, and mechanical stirrer. The mixture is cooled and 18.0 grams (0.1 mole) of 6-methoxy-2-aminobenzothiazole are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 milliliter beaker is charged with 218 grams (0.11 mole) of 30EO-H sulfonamide intermediate from EXAMPLE #16B, 300 grams of water, 300 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

EXAMPLE #16I

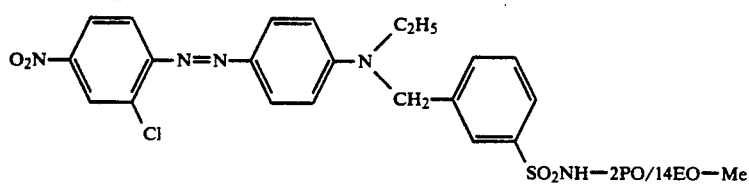

One hundred eighty grams acetic acid, 41 grams propionic acid, and 4 drops of 2-ethyl hexanol defoamer are added to a 500 milliliter three necked flask equipped with a thermometer, cooling bath, and mechanical stirrer. The mixture is cooled and 17.2 grams (0.1 mole) of 2-chloro-4-nitroaniline are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 milliliter beaker is charged with 121 grams (0.11 mole) of 2PO/14EO-Me sulfonamide intermediate from Example #16A, 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a bluish red liquid.

EXAMPLE #17

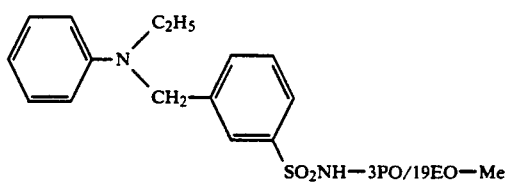

A mixture is prepared by adding 1235.3 grams (1.05 mole) of Jeffamine M-10000 primary amine with an amine equivalent weight of 0.85 meq/g), 259.8 grams of sodium carbonate in 2000 ml of water. The mixture is cooled to 10°-15° C. and 309 grams (1 mole) of N-ethyl-N-benzylanilinesulfonyl chloride (of EXAMPLE #16) are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield the intermediate.

EXAMPLE #17A

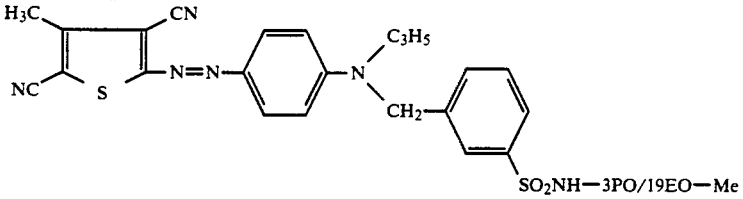

One hundred eighty-three grams of 85% phosphoric acid, 25 grams of 98% sulfuric acid, and 3 drops of 2-ethylhexanol defoamer are added to a 1000 milliliter three necked flask equipped with a thermometer, cooling bath, and mechanical stirrer. The mixture is cooled and 16.3 grams (0.1 mole) of 2-amino-3,5-dicyano-4-methylhiophene are added to the flask. The mixture is further cooled to below 0° C. after which 35 grams of 40% nitrosyl sulfuric acid are added while maintaining the temperature below 5° C. After three hours the mixture gives a positive nitrite test and 2.5 grams of sulfamic acid are added slowly keeping the temperature below 5° C. A negative nitrite test is evident after one further hour.

A 2000 milliliter beaker is charged with 159.5 grams of (0.11 mole) of 2PO/19EO-Me sulfonamide intermediate (of EXAMPLE #17), 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a violet liquid.

EXAMPLE #17B

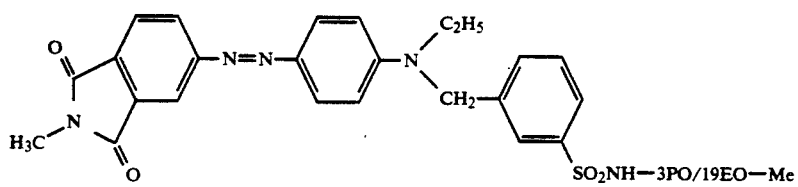

One hundred and eighty-three grams of 85% phosphoric acid, 25 grams of 98% sulfuric acid, and 3 drops of 2-ethylhexanol defoamer are added to a 500 milliliter three necked flask equipped with a thermometer, cooling bath, and mechanical stirrer. The mixture is cooled and 17.6 grams (0.1 mole) of 4-amino-N-methylphthalimide are added to the flask. The mixture is further cooled to below 0° C. after which 35 grams of 40% nitrosyl sulfuric acid are added while maintaining the temperature below 5° C. After three hours the mixture gives a positive nitrite test and 1 gram of sulfamic acid is added slowly keeping the temperature below 5° C. A negative nitrite test is evident after one further hour.

A 2000 milliliter beaker is charged with 159.5 grams of (0.11 mole) of 2PO/19EO-Me sulfonamide intermediate (of EXAMPLE #17), 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange liquid.

three hours. Thirteen grams of chloranil are added and the mixture is heated for an additional two hours. The heat is then removed and the mixture is then cooled to room temperature. The resulting mixture is stirred for several hours and allowed to stand overnight, after which sodium hydroxide is added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a blue liquid.

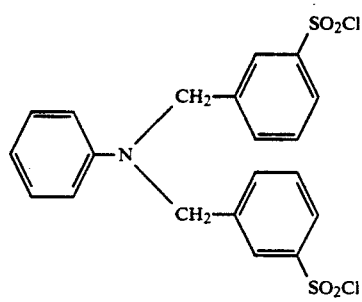

Five hundred thirty-two grams of chlorosulfonic acid are charged to a three liter, three necked, round bottomed flask equipped with mechanical stirrer, nitrogen (inlet/outlet), and ice bath.

Upon cooling to 20° C., 273 grams (1.0 mole) of N,N-dibenzylaniline are slowly added over 1 hour maintaining the temperature below 30° C. Upon complete addition of the aniline (compound), the temperature is increased to 9° C. for four hours. Afterwards the reaction solution is quenched by slowly poured into ice water. The product is taken up in methylene chloride in a separatory funnel where it is washed repeatedly with dilute sodium carbonate solution. The methylene chloride is then evaporated to dryness to yield the pale green solid dibenzylanilinedisulfonyl chloride intermediate.

EXAMPLE #17C

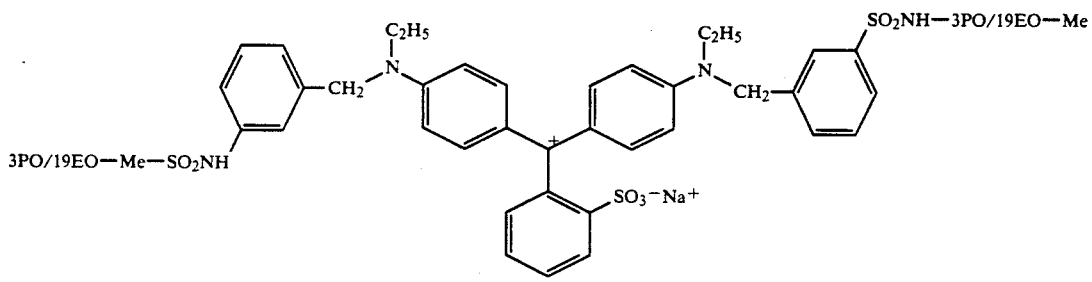

Twenty six grams (0.1 mole) 80% of o-formylbenzenesulfonic acid sodium salt (80% assay), 319 grams (0.22 mole) of the sulfonamide 3PO/19EO-Me intermediate from EXAMPLE #17, 1.4 grams of urea, and 12 grams of dilute mineral acid are added to a stirred 1000 milliliter flask. The contents are then heated to 90° C. for

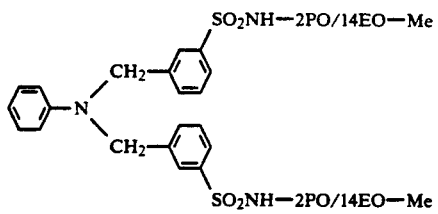

A mixture is prepared by adding 1554 grams (2.1 mole) of primary amine with an amine equivalent weight of 1.35 meq/g) 260 grams of sodium carbonate in 2000 ml of water. The mixture is cooled to 10°–15° C. and 469 grams (1 mole) of dibenzylanilinedisulfonyl chloride (of EXAMPLE #18) are added to the mixture over one half hour. After the addition is complete, the mixture is warmed at 50° C. for an additional two hours to insure complete reaction. Eighty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

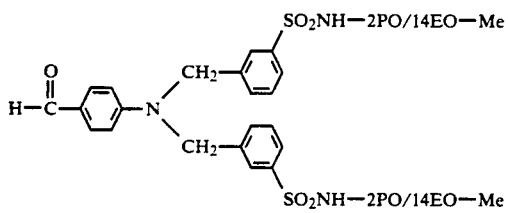

A dry 2000 ml three-neck flask is charged with 181 grams N,N-dimethylformamide under nitrogen and cooled to 0° C. One hundred ninety-two grams of phosphorous oxychloride are added dropwise with mechanical stirring and cooling over one hour. The resulting mixture is stirred for an additional two hours at 0°–5° C. Then 1877 grams (1 mole) of 2PO/14EO-Me disulfonamide intermediate (of Example #18A) are added dropwise. The reaction mixture is gradually heated to 90° C. and held at this temperature for an additional two hours to insure complete reaction. After cooling, the mixture is diluted with an equal amount of ice and 2.5 moles of sodium hydroxide (50 percent by weight). The resulting mixture is heated to 50°–60° C. until the formylated sulfonamide intermediate is hydrolyzed. The resulting mixture is then neutralized with acetic acid and the product extracted into methylene chloride. The methylene chloride layer is phase separated and dried over anhydrous magnesium sulfate. The methylene chloride solution is filtered and the solvent is removed by reduced vacuum at 90° C. An IR spectrum of the resulting liquid product displays the presence of the characteristic carbonyl absorbance of the corresponding formyl intermediate.

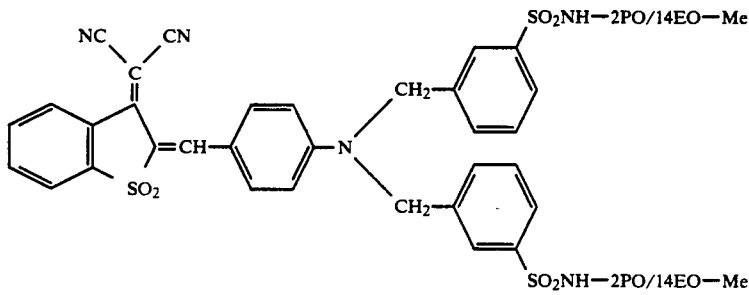

One hundred eighty seven grams of aldehyde (0.1 mole) from EXAMPLE #18B, 22.8 grams of substituted 3(2H)-thianaphthalenone (0.1 mole), two drops of piperidine catalyst and 300 milliters of toluene are charged into a 500 milliter three necked flask equipped with thermometer, reflux condenser, Dean-Stark trap, mechanical stirrer, and heating mantle. This mixture is heated at reflux until no more water condenses in the trap which takes about four hours. The resulting mixture is dissolved in methylene chloride and is washed with water three times. The resulting methylene chloride solution is then dried over magnesium sulfate and filtered into a 500 milliter round bottom flask. The solution is then stripped of all volatiles under reduced pressure to give a blue liquid.

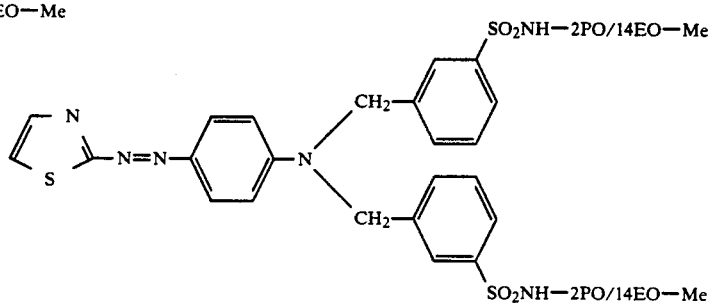

Five hundred and forty-nine grams of 85% phosphoric acid, 75 grams of 98% sulfuric acid, and 9 drops of 2-ethyl hexanol defoamer are added to a 1000 milliliter three necked flask equipped with a thermometer, cooling bath, and mechanical stirrer. The mixture is cooled and 30.9 grams (0.3 mole) of 2-aminothiazole are added to the flask. The mixture is further cooled to below 0° C. after which 105 grams of 40% nitrosyl sulfuric acid are added while maintaining the temperature below 5° C. After three hours the mixture gives a positive nitrite test and 2.5 grams of sulfamic acid are added slowly keeping the temperature below 5° C. A negative nitrite test is evident after one further hour.

A 4000 milliliter beaker is charged with 619.4 grams of (0.33 moles) of 2PO/14 EO-Me disulfonamide intermediate (of EXAMPLE #18A), 500 grams of water, 500 grams of ice and 12 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 780 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give an orange liquid.

weight of 2.70 meq/g), 519.6 grams of sodium carbonate in 2000 ml of water. The mixture is cooled to 10°–15° C. and 469 grams (1 mole) of dibenzyl-anilinedisulfonyl chloride of (EXAMPLE 18) are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

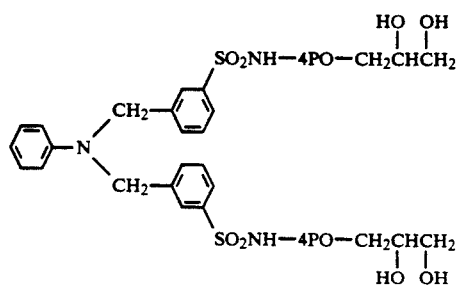

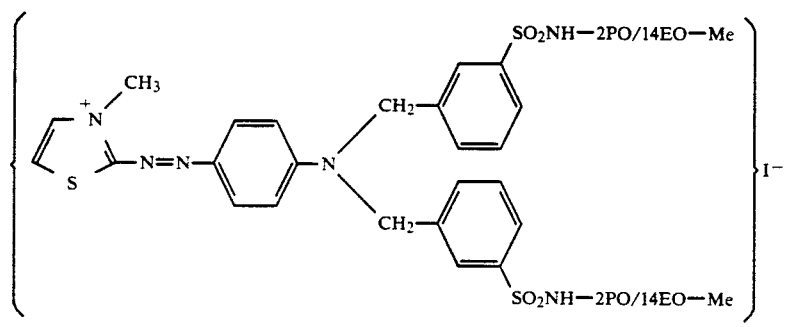

One hundred ninety nine grams (0.1 mole) of thiazole azo intermediate (prepared in EXAMPLE #18D) are added to a plastic encased bottle along with 35.5 grams (0.25 mole) methyl iodide at 5° C. The bottle is sealed with a stopper and copper wire and is placed in a steam bath for approximately two hours. At the end of this reaction period, the bottle is uncapped and any excess methyl iodide volatilized off to give a bluish violet liquid.

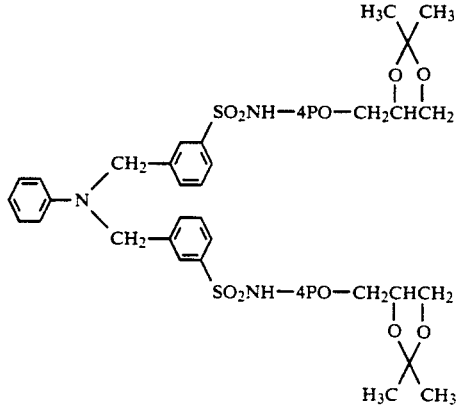

A mixture is prepared by adding 777 grams (2.1 moles) of primary amine with an amine equivalent One hundred thirty seven grams (0.12 mole) of the acetal prepared in Example #19 are added along with 100 ml of water to a three necked 500 ml flask equipped with overhead stirrer, heating mantle, and Dean-Stark trap. The mixture is heated to 80° C. and 20 grams of 70% sulfuric acid are added. This reaction mixture is maintained at 80° C. until no more acetone could be detected overhead in the trap. The mixture is then cooled and the product is extracted into methylene chloride. The methylene chloride solution is separated, washed several times with water to neutral pH, and dried over anhydrous magnesium sulfate. The dried methylene chloride solution is filtered and stripped under reduced pressure at 90° C. to give a liquid product containing a hydroxyl band in the IR spectrum.

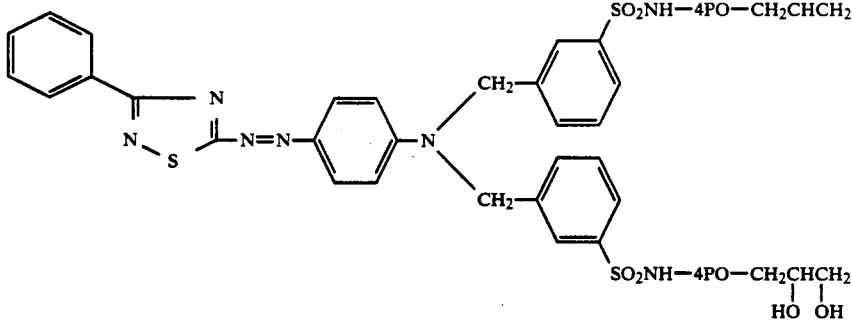

One hundred eighty-three grams of 85% phosphoric acid, 25 grams of 98% sulfuric acid, and 3 drops of 2-ethylhexanol defoamer are added to a 1000 milliliter three necked flask equipped with a thermometer, cooling bath, and mechanical stirrer. The mixture is cooled and 17.7 grams (0.1 mole) of 5-amino-3-phenyl-1,2,4-thiadiazole are added to the flask. The mixture is further cooled to below 0° C. after which 35 grams of 40% nitrosyl sulfuric acid are added while maintaining the temperature below 5° C. After three hours the mixture gives a positive nitrite test and 2.5 grams of sulfamic acid are added slowly keeping the temperature below 5° C. A negative nitrite test is evident after one further hour.

A 2000 milliliter beaker is charged with 116.5 grams (0.11 mole) of the amine disulfonamide intermediate from EXAMPLE #19A, 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

EXAMPLE #20

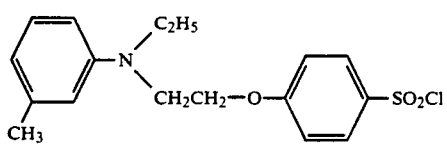

Five hundred thirty-two grams of chlorosulfonic acid are charged to a three liter, three neck, round bottomed flask equipped with mechanical stirrer, nitrogen (inlet/outlet), and ice bath. Upon cooling to 20° C., 254 grams (1.0 mole) of N-ethyl N-(2-phenoxyethyl)m-toluidine are slowly added over a period of 1 hour maintaining the temperature below 30° C. Upon complete addition of the aniline compound, the temperature is increased to 55°–60° C. for one hour, and 80° C. for four hours. Afterwards, the reaction solution is quenched by slowly poured into ice water. The product is taken up in methylene chloride in a separatory funnel where is washed repeatedly with dilute sodium carbonate solution. The methylene chloride is then evaporated to yield the N-ethyl N-(2-phenoxyethyl)m-toluidine sulfonyl chloride intermediate.

EXAMPLE #20A

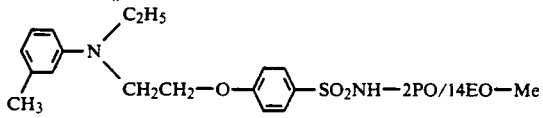

A mixture is prepared by adding 777 grams (1.05 mole) of primary amine with an amine equivalent weight of 1.35 meq/g) 120 grams of sodium carbonate in 2000 ml of water. The mixture is cooled to 10°–15° C. and 338 grams (1 mole) of N-ethyl N-(2-phenoxyethyl)m-toluidinesulfonyl chloride from EXAMPLE #20 are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #20B

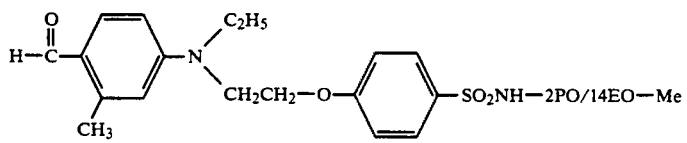

A dry 2000 ml three-neck flask is charged with 181 grams N,N dimethylformamide under nitrogen and cooled to 0° C. One hundred ninety-two grams of phosphorous oxychloride are added dropwise with mechanical stirring and cooling over one hour. The resulting mixture is stirred for an additional two hours at 0°–5° C. Then 1058 grams (1 mole) of 2PO/14EO-Me sulfonamide intermediate (of Example #20A) are added dropwise. The reaction mixture is gradually heated to 90° C.

and held at this temperature for an additional two hours to insure complete reaction. After cooling, the mixture is diluted with an equal amount of ice and 2.5 moles of sodium hydroxide (50 percent by weight). The resulting mixture is heated to 50°-60° C. until the formylated sulfonamide intermediate is hydrolyzed. The resulting mixture is then neutralized with acetic acid and the product extracted into methylene chloride. The methylene chloride layer is phase separated and dried over anhydrous magnesium sulfate. The methylene chloride solution is filtered and the solvent is removed by reduced vacuum at 90° C. An IR spectrum of the resulting liquid product displays the presence of the characteristic carbonyl absorbance of the corresponding formyl intermediate.

hours the mixture gives a positive nitrite test and 2.5 grams of sulfamic acid are added slowly keeping the temperature below 5° C. A negative nitrite test is evident after one further hour.

A 2000 milliliter beaker is charged with 116.4 grams (0.11 mole) of the amine sulfonamide 2PO/14EO-Me intermediate (from EXAMPLE 20A), 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt

EXAMPLE #20C

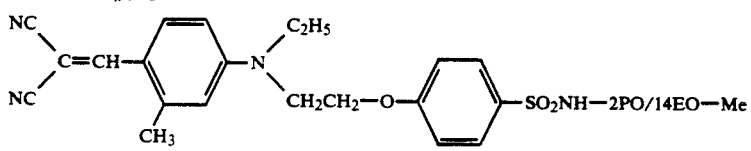

One hundred seven grams of aldehyde (0.1 mole) of EXAMPLE #20B, 6.6 grams of malononitrile (0.1 mole), two drops of piperidine catalyst and 300 milliters of toluene are charged into a 500 milliter three necked flask equipped with thermometer, reflux condenser, layer is removed and the product is dissolved in methylene chloride. The methylene chloride solution is washed four times with water and then dried over sodium sulfate. The methylene chloride solvent is then filtered and stripped to give a red liquid.

EXAMPLE #20E

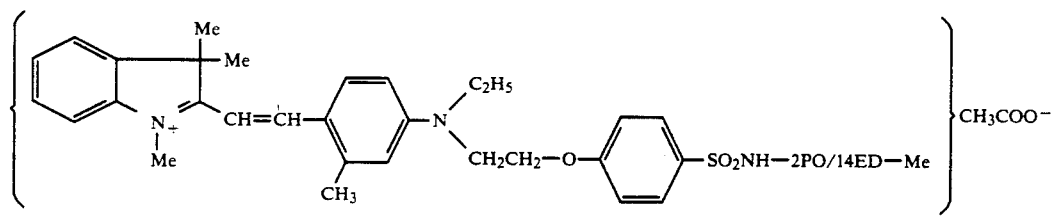

Dean-Stark trap, mechanical stirrer, and heating mantle. This mixture is heated at reflux until no more water condenses in the trap which takes about four hours. The resulting mixture is dissolved in methylene chloride and washed with water three times. The resulting methylene chloride solution is then dried over magnesium sulfate and filtered into a 500 milliter round bottom flask. The solution is then stripped of all volatiles under reduced pressure to give a yellow liquid.

Four hundred grams of acetic acid, 17.3 grams (0.1 mole) 2-methylene-1,3,3-trimethylindoline, and 114 grams (0.105 mole) of formylaniline sulfonamide 2PO/14EO-Me intermediate from EXAMPLE #20B are charged into a 2000 milliliter three necked flask equipped with a reflux condenser, thermometer, heating mantle, and mechanical stirrer. This mixture is heated to 95° C. with the heating mantle and is maintained at 95°-100° C. for an additional 6 hours. The reaction

EXAMPLE 20D

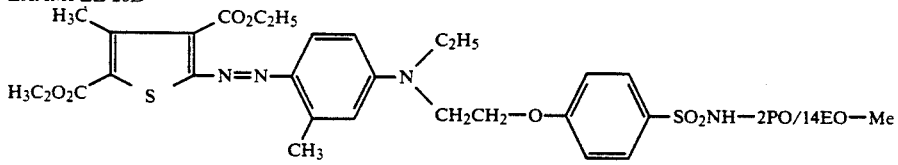

One hundred eighty-three grams of 85% phosphoric acid, 25 grams of 98% sulfuric acid, and 3 drops of 2-ethylhexanol defoamer are added to a 1000 milliliter three necked flask equipped with a thermometer, cooling bath, and mechanical stirrer. The mixture is cooled and 25.7 grams (0.1 mole) of 2-amino-3,5-dicarboethoxy-4-methylthiophene are added to the flask. The mixture is further cooled to below 0° C. after which 35 grams of 40% nitrosyl sulfuric acid are added while maintaining the temperature below 5° C. After three mixture is cooled and transferred to a 2000 milliliter round bottom flask and stripped of acetic acid. The pH of the resulting product is adjusted with 25% sodium hydroxide to 7 to give a bluish-red product.

EXAMPLE 20F

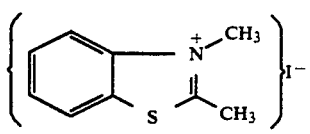

Seventy grams (0.47 mole) of 2-methylbenzothiazole are quickly added to a plastic encased bottle along with 133.2 grams (0.94 mole) methyl iodide at 5° C. The bottle is sealed with a stopper and copper wire and is placed in a steam bath for approximately two hours. At the end of this reaction period, the bottle is uncapped and any excess methyl iodide volatilized off. The product is isolated as a crushed solid.

EXAMPLE #20G

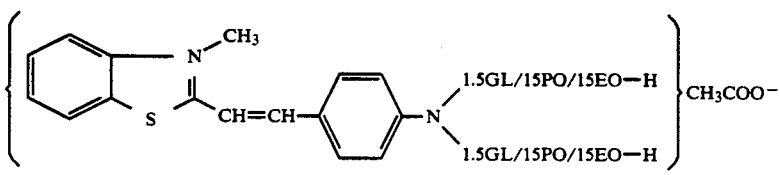

One hundred nineteen grams (0.14 mole) methylium methyl benzothiazole iodide (from EXAMPLE 20F), (0.11 mole) of formylaniline sulfonamide 2PO/14EO-Me intermediate from EXAMPLE #20B and 0.2 gram of morpholine catalyst are charged into a 1000 milliliter three necked flask equipped with a reflux condenser, thermometer, heating mantle, and mechanical stirrer. This mixture is heated to 85° C. with the heating mantle and is maintained at 85° C. for an additional 3 hours. The reaction mixture is cooled and transferred to a 1000 milliliter round bottom flask and stripped of all volatiles and collected to give a red liquid.

EXAMPLE #21

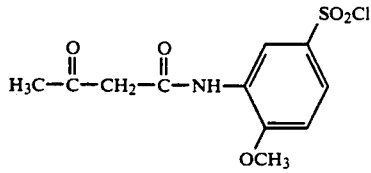

Six hundred thirty-two grams of chlorosulfonic acid are charged to a three liter, three neck, round bottomed flask equipped with mechanical stirrer, nitrogen (inlet/-outlet), and ice bath.

Upon cooling to 20° C., 207.2 grams (1.0 mole) of o-acetoacetanisidide are slowly added over 1 hour maintaining the temperature below 30° C. Upon complete addition of the compound, the temperature is increased to 55°-60° C. for one hour, and 80°-90° C. for four hours. Afterwards, the reaction solution is quenched by slowly poured into ice water. The product is taken up in methylene chloride in a separatory funnel where is washed to pH 7 with salt solution. The methylene chloride is then evaporated to yield the solid o-acetoacetanisididesulfonyl chloride intermediate.

EXAMPLE #21A

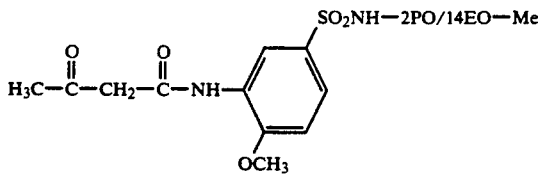

A mixture is prepared by adding 777 grams (1.05 mole) of primary amine with an amine equivalent weight of 1.35 meq/g) 129.9 grams of sodium carbonate in 2000 ml of water. The mixture is cooled to 10°-15° C. and 271 grams (1 mole) of o-acetoacetanisididesulfonyl chloride (from EXAMPLE 21) are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #21B

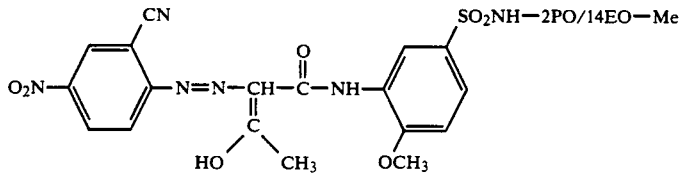

One hundred eighty grams acetic acid, 41 grams propionic acid, and 4 drops of 2-ethylhexanol defoamer are added to a 500 milliliter three necked flask equipped with a thermometer, cooling bath, and mechanical stirrer. The mixture is cooled and 16.3 grams (0.1 mole) of 2-cyano-4-nitroaniline are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 ml millititer beaker equipped with a thermometer, cooling bath, and mechanical stirrer is charged with 200 grams of water, 29.2 grams of 50 percent sodium hydroxide and 102.5 grams (0.105 mole) of the sulfonamide 2PO/14EO-Me intermediate of EXAMPLE #21A. The mixture is cooled to below 5° C. The diazo solution is added slowly dropwise to the beaker, maintaining the temperature below 5° C. and the pH is kept in the range of 4-7 with caustic. The resulting mixture is stirred for three hours for post coupling. At the end of this period, the pH is adjusted to 7.0 with dilute hydrochloric acid keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a yellow liquid.

EXAMPLE #22

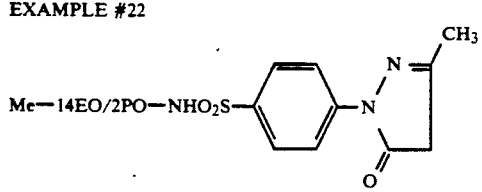

A mixture is prepared by adding 777 grams (1.05 mole) of primary amine with an amine equivalent weight of 1.35 meq/g) 129.9 grams of sodium carbonate in 2000 ml of water. The mixture is cooled to 10°-15° C. and 273 grams (1 mole) of 1-(-4'chlorosulfonyl-phenyl-)-3-methyl-5-pyrazolone are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #22A

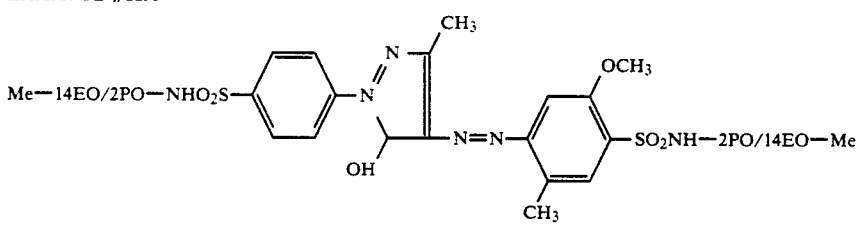

A 2000 ml milliliter beaker equipped with a thermometer, cooling bath, and mechanical stirrer is charged with 200 grams of water, 29.2 grams of 50 percent sodium hydroxide, 62 grams of Versene (sodium salt of EDTA), and 215.2 grams (0.22 mole) of the sulfonamide 2PO/14EO-Me intermediate from EXAMPLE #22. The mixture is cooled to below 5° C. The diazo solution (as prepared in Example #11B) is added slowly dropwise to the beaker, maintaining the temperature below 5° C. and the pH is kept in the range of 4-7 with Versene. When the addition is complete, the resulting mixture is stirred for three hours for post coupling. At the end of this period, the pH is adjusted to 8.5 with 50 percent sodium hydroxide where the yellow colored layer phase separates from the aqueous salt layer.

EXAMPLE #23

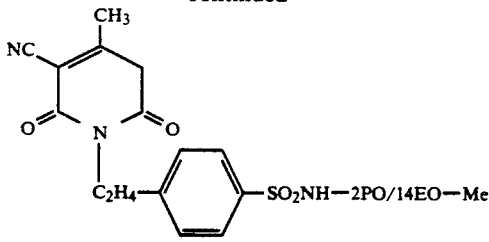

A mixture is prepared by adding 77 grams (1.05 mole) of primary amine with an amine equivalent weight of 1.35 meq/g) 129.9 grams of sodium carbonate in 2000 ml of water. The mixture is cooled to 10°-15° C. and 352 grams (1 mole) of pyridone sulfonyl chloride are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #23A

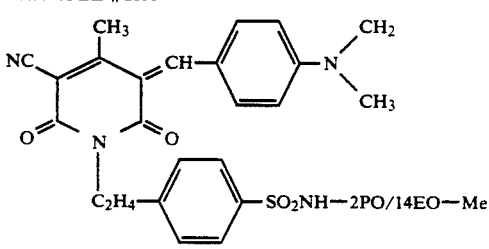

Fifteen grams (0.1 mole) dimethylaminobenzaldehyde, 105.7 grams (0.1 mole) of the sulfonamide 2PO/14EO-Me dione intermediate from EXAMPLE #23, two drops of piperidine catalyst and 300 milliters of toluene are charged into a 500 milliter three necked flask equipped with thermometer, reflux condenser, Dean-Stark trap, mechanical stirrer, and heating mantle. This mixture is heated at reflux until no more water condenses in the trap which takes about four hours. The resulting mixture is dissolved in methylene chloride and is washed with water three times. The resulting methylene chloride solution is then dried over magnesium sulfate and filtered into a 500 milliter round bottom flask. The solution is then stripped of all volatiles under reduced pressure to give a violet liquid.

EXAMPLE #23B

83

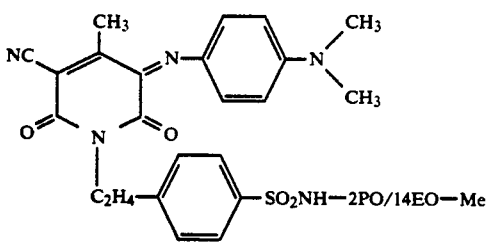

Fifteen grams (0.1 mole) dimethylaminonitrosoaniline, 105.7 grams (0.1 mole) of the sulfonamide 2PO/14EO-Me dione intermediate from EXAMPLE #23, and 300 milliters of toluene are charged into a 500 milliter three necked flask equipped with thermometer, reflux condenser, Dean-Stark trap, mechanical stirrer, and heating mantle. This mixture is heated at reflux until no more water condenses in the trap which takes about four hours. The resulting mixture is dissolved in methylene chloride and is washed with water three times. The resulting methylene chloride solution is then dried over magnesium sulfate and filtered into a 500 milliter round bottom flask. The solution is then stripped of all volatiles under reduced vacuum to give a blue liquid.

EXAMPLE #23C

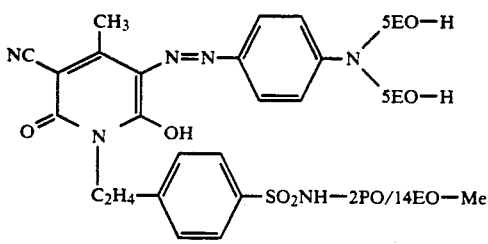

A solution of 68.3 grams (0.125 mole) of p-phenylenediamine 10EO-H intermediate, 45 milliters concentrated hydrochloric acid, and 90 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 200 grams of water, 29.2 grams of 50 percent sodium hydroxide and 137.4 grams (0.13 mole) of the sulfonamide 2PO/14EO-Me dione intermediate from EXAMPLE #23. The mixture is cooled to below 5° C. The diazo solution is added slowly dropwise to the beaker, maintaining the temperature below 5° C. and the pH is kept in the range of 4-7 with caustic. The resulting mixture is stirred for three hours for post coupling. At the end of this period, the pH is adjusted to 7.0 with dilute hydrochloric acid keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a yellow liquid.

EXAMPLE #24

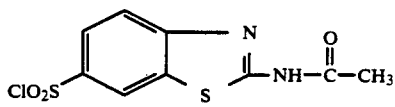

One hundred fifty grams (1.0 mole) of 2-aminobenzothiazole, and 250 grams of acetic acid are charged into a one liter, three necked round bottomed flask equipped with thermometer, mechanical stirrer, heating mantle, and nitrogen (inlet/outlet). This slurry is heated to 80° C. where a homgeneous solution is results. One hundred and sixty grams (1.5 moles) of acetic anhydride are slowly added through an addition funnel to avoid violent exotherms. Upon completion of acetic anhydride addition, the temperature is increased to 70° C. for two hours. The mixture is cooled and is poured slowly into cold water to precipitate the acetylated intermediate. The white crystalline product (2-acetamido-benzothiazole) is collected and washed with water on a sintered glass filter.

Five hundred thirty-two grams of chlorosulfonic acid are charged to a three liter, three neck, round bottomed flask equipped with mechanical stirrer, nitrogen (inlet/outlet), and ice bath.

Upon cooling to 15° C., 192 grams (1.0 mole) of 2-acetamido-benzothiazole are slowly added maintaining the temperature below 30° C. Upon complete addition of the acetylated material, the temperature is increased to 60° C. for three hours. At the end of the reaction period, the reaction solution is quenched by slowly poured into ice water. The product is taken up in methylene chloride in a separatory funnel where it is washed repeatedly with dilute sodium carbonate solution. The methylene chloride is then evaporated to dryness to yield the 2-acetamido-6-chlorosulfonylbenzothiazole intermediate.

EXAMPLE #24A

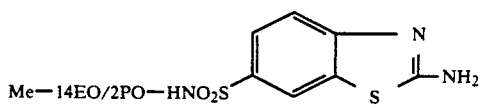

A mixture is prepared by adding 777 grams (1.05 mole) of primary amine with an amine equivalent weight of 1.35 meq/g) to 120 grams of sodium carbonate in 2000 ml of water. The mixture is cooled to 10°-15° C. and 290 grams (1 mole) of 2-acetamido-6-chlorosulfonylbenzothiazole intermediate are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #24B

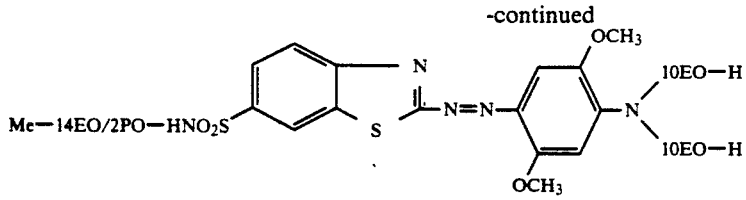

One hundred eighty grams acetic acid, 41 grams propionic acid, and 4 drops of 2-ethylhexanol defoamer are added to a 500 milliliter three necked flask equipped with a thermometer, cooling bath, and mechanical stirrer. The mixture is cooled and 98.8 grams (0.1 mole) of the 2-aminobenzothiazole 2PO/14EO-Me sulfonamide intermediate of EXAMPLE #24A are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 milliliter beaker is charged with 113.6 grams (0.11 mole) of 2,5-dimethoxyaniline 20EO-H intermediate, 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a violet liquid.

EXAMPLE #24C

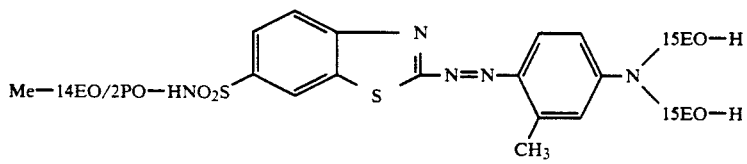

One hundred eighty grams acetic acid, 41 grams propionic acid, and 4 drops of 2-ethylhexanol defoamer are added to a 500 milliliter three necked flask equipped with a thermometer, cooling bath, and mechanical stirrer. The mixture is cooled and 98.8 grams (0.1 mole) of the 2-aminobenzothiazole 2PO/14EO-Me sulfonamide intermediate of EXAMPLE #24A are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 milliliter beaker is charged with 157 grams (0.11 mole) of m-toluidine 30EO-H intermediate, 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

EXAMPLE #25

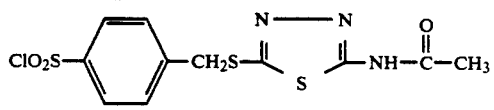

Two hundred twenty-three grams (1.0 mole) of 2-amino-5-benzylthio-1,3,4-thiadiazole, and 300 grams of acetic acid are charged into a one liter, three necked round bottomed flask equipped with thermometer, mechanical stirrer, heating mantle, and nitrogen (inlet/outlet). This slurry is heated to 80° C. where a homgeneous solution is results. One hundred sixty grams (1.5 moles) of acetic anhydride are slowly added through an addition funnel to avoid violent exotherms. Upon completion of acetic anhydride addition, the temperature is increased to 70° C. for two hours. The mixture is cooled and is poured slowly into cold water to precipitate the acetylated intermediate. The crystalline product 2-acetamido-5-(4-chlorosulfonylbenzylthio)-1,2,3-thiadiazole is collected and washed with water on a sintered glass filter.

Five hundred thirty-two grams of chlorosulfonic acid are charged to a three liter, three neck, round bottomed flask equipped with mechanical stirrer, nitrogen (inlet/outlet), and ice bath.

Upon cooling to 15° C., 132.5 grams (0.5 mole) of 2-acetamido-5-(4-chlorosulfonylbenzylthio)-1,3,4-thiadiazole are slowly added maintaining the temperature below 30° C. Upon complete addition of the acetylated material, the temperature is increased to 70° C. for four hours. At the end of the reaction period, the reaction solution is quenched by slowly poured into ice water. The product is taken up in methylene chloride in a separatory funnel where it is washed repeatedly with dilute sodium carbonate solution. The methylene chloride is then evaporated to dryness to yield the 2- acetamido-5-(4-chlorosulfonylbenzylthio)-1,3,4-thiadiazole intermediate.

EXAMPLE #25A

A mixture is prepared by adding 777 grams (1.05 mole) of primary amine with an amine equivalent weight of 1.35 meq/g), 129 grams of sodium carbonate in 2000 ml of water. The mixture is cooled to 10°–15° C. and 322 grams (1 mole) of 2-acetamido-5-(4-chlorosulfonylbenzylthio)-1,3,4-thiadiazole intermediate are added to the mixture over one half hour. After the addition is complete, the mixture is warmed at 50° C. for an additional two hours to insure complete reaction. Forty grams (1 mole) of sodium hydroxide are added to the mixture and the mixture is heated at reflux one hour. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #25B

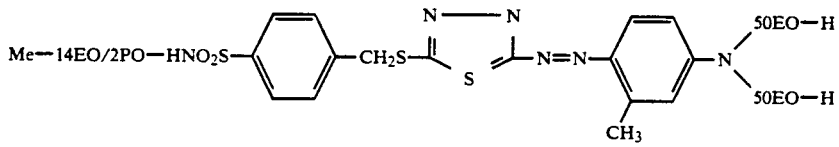

One hundred eighty grams acetic acid, 41 grams propionic acid, and 4 drops of 2-ethylhexanol defoamer are added to a 500 milliliter three necked flask equipped with a thermometer, cooling bath, and mechanical stirrer. The mixture is cooled and 98.5 grams (0.1 mole) of the 2-amino-5-(4-chlorosulfonyl benzylthio)-1,3,4-thiadiazole 2PO/14EO-Me sulfonamide intermediate of EXAMPLE #25A are added to the flask. The mixture is further cooled to below 5° C. after which 33 grams of 40% nitrosyl sulfuric acid are added while maintaining the temperature below 10° C. After three hours the mixture gives a positive nitrite test and 2 grams of sulfamic acid are added slowly keeping the temperature below 5° C. A negative nitrite test is evident after one further hour.

A 2000 milliliter beaker is charged with 496 grams (0.11 mole) of m-toluidine 100EO-H intermediate, 500 grams of water, 500 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a red liquid.

EXAMPLE #26

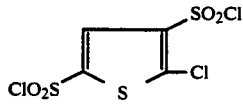

Two thousand five hundred ninety-six milliliters of chlorosulfonic acid are charged to a three liter, three neck, round bottomed flask equipped with mechanical stirrer, nitrogen (inlet/outlet), and ice bath.

Upon cooling to 20° C., 260 grams (2.19 moles) of 2-chlorothiophene are slowly added maintaining the temperature below 30° C. Upon complete addition of the chlorothiophene, the temperature is increased to 90° C. for six hours. Afterwards, the reaction solution is quenched by slowly poured into ice water. The product is taken up in methylene chloride in a separatory funnel where it is washed repeatedly with dilute sodium carbonate solution. The methylene chloride is then evaporated to dryness to yield the pale green solid 2-chloro-3,5-dichlorosulfonylthiophene intermediate.

EXAMPLE #26A

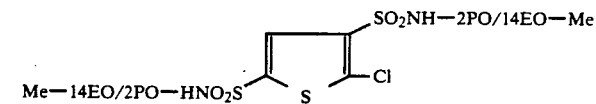

A mixture is prepared by adding 1554 grams (2.1 mole) of primary amine with an amine equivalent weight of 1.35 meq/g), 260 grams of sodium carbonate in 2000 ml of water. The mixture is cooled to 10°–15° C. and 469 grams (1 mole) of 2-chloro-3,5-dichlorosulfonylthiophene (of EXAMPLE 26) are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #26B

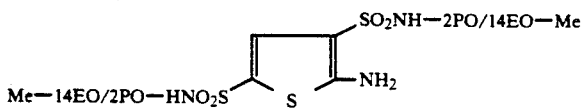

In a two liter autoclave are charged 187.9 grams (0.1 mole) of the disulfonamide 2PO/14EO-Me intermediate (of EXAMPLE 26A), 1000 milliliters of butyl Cellosolve and 300 grams of ammonia. The reactor is then heated to 140°-150° C. for 6 hours. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #26C

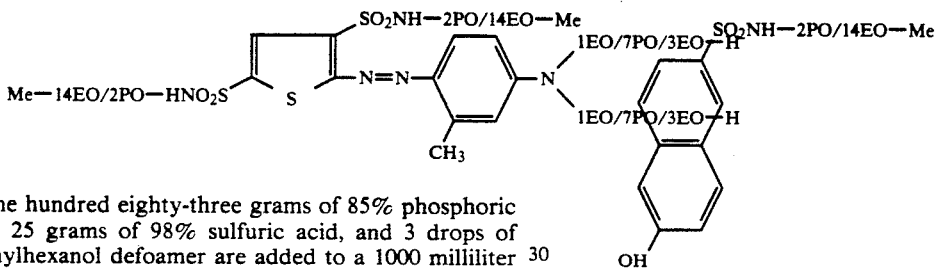

One hundred eighty-three grams of 85% phosphoric acid, 25 grams of 98% sulfuric acid, and 3 drops of 2-ethylhexanol defoamer are added to a 1000 milliliter three necked flask equipped with a thermometer, cooling bath, and mechanical stirrer. The mixture is cooled and 186 grams (0.1 mole) of amino disulfonamide 2PO/14EO-Me intermediate from EXAMPLE #26B are added to the flask. The mixture is further cooled to below 0° C. after which 35 grams of 40% nitrosyl sulfuric acid are added while maintaining the temperature below 5° C. After three hours the mixture gives a positive nitrite test and 2.5 grams of sulfamic acid are added slowly keeping the temperature below 5° C. A negative nitrite test is evident after one further hour.

A 2000 milliliter beaker is charged with 139.8 grams of (0.11 mole) of m-toluidine 2EO/14PO/6EO-H intermediate, 200 grams of water, 200 grams of ice and 4 grams of urea. This mixture is cooled to below 0° C. The diazo solution is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a violet liquid.

EXAMPLE #27

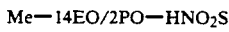

A mixture is prepared by adding 777 grams (1.05 mole) of primary amine with an amine equivalent weight of 1.35 meq/g) 129.9 grams of sodium carbonate in 2000 ml of water. The mixture is cooled to 10°-15° C. and 242 grams (1 mole) of 6-chlorosulfonyl-2-naphthol are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #27A

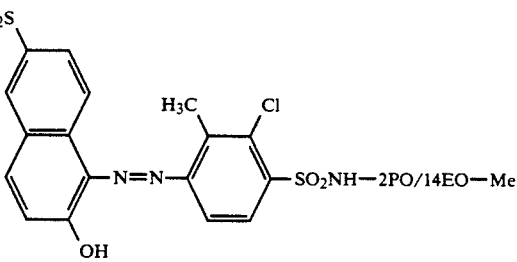

A 2000 ml milliliter beaker equipped with a thermometer, cooling bath, and mechanical stirrer is charged with 200 grams of water, 29.2 grams of 50 percent sodium hydroxide, and 208.3 grams (0.22 mole) of 2PO/14EO-Me sulfonamide intermediate from EXAMPLE #27. The mixture is cooled to below 5° C. The diazo solution (as prepared in Example #15A) is added slowly dropwise to the beaker, maintaining the temperature below 5° C. and the pH is kept in the range of 4-7 with caustic. When the addition is complete, the resulting mixture is stirred for three hours for post coupling. At the end of this period, the pH is adjusted to 8.5 with 50 percent sodium hydroxide where the orange red colored layer phase separates from the aqueous salt layer.

filtered and stripped under reduced pressure at 90° C. to yield a liquid intermediate.

EXAMPLE #28A

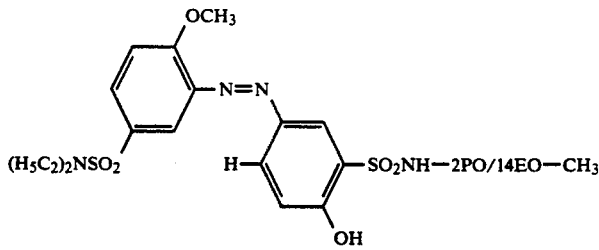

A solution of 32.3 grams (0.125 mole) of 2-methoxy-5-N,N-diethylsulfamoylaniline, 90 milliters concentrated hydrochloric acid, and 150 milliters of water is added to a 500 milliter flask and cooled to 0°-5° C. Ten grams of sodium nitrite are added maintaining the mixture below 10° C. After three hours, the mixture gives a positive nitrite test and 2 grams of sulfamic acid are added slowly keeping the temperature below 5° C. A negative nitrite test is evident after one further hour.

A 2000 ml milliliter beaker equipped with a thermometer, cooling bath, and mechanical stirrer is charged with 200 grams of water, 29.2 grams of 50 percent sodium hydroxide, and 200.9 grams (0.22 mole) of 2PO/14EO-Me sulfonamide intermediate from EXAMPLE #28. The mixture is cooled to below 5° C. The diazo solution is added slowly dropwise to the beaker, maintaining the temperature below 5° C. and the pH is kept in the range of 4-7 with caustic. When the addition is complete, the resulting mixture is stirred for three hours for post coupling. At the end of this period, the pH is adjusted to 8.5 with 50 percent sodium hydroxide where the orange colored layer phase separates from the aqueous salt layer.

EXAMPLE #27B

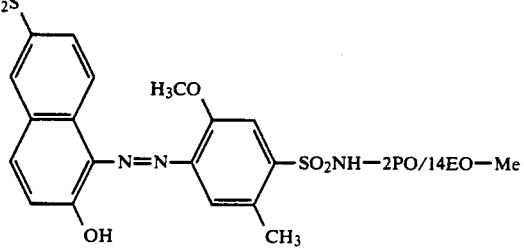

A 2000 ml milliliter beaker equipped with a thermometer, cooling bath, and mechanical stirrer is charged with 200 grams of water, 29.2 grams of 50 percent sodium hydroxide, and 208.3 grams (0.22 mole) of 2PO/14EO-Me sulfonamide intermediate from EXAMPLE #27. The mixture is cooled to below 5° C. The diazo solution (as prepared in Example #11B) is added slowly dropwise to the beaker, maintaining the temperature below 5° C. and the pH is kept in the range of 4-7 with caustic. When the addition is complete, the resulting mixture is stirred for three hours for post coupling. At the end of this period, the pH is adjusted to 8.5 with 50 percent sodium hydroxide where the red colored layer phase separates from the aqueous salt layer.

EXAMPLE #28

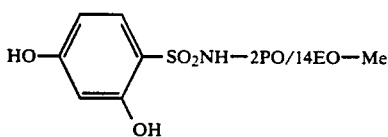

A mixture is prepared by adding 777 grams (1.05 mole) of primary amine with an amine equivalent weight of 1.35 meq/g) 129.9 grams of sodium carbonate in 2000 ml of water. The mixture is cooled to 10°-15° C. and 208 grams (1 mole) of 2-chlorosulfonylresorcinol are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is

EXAMPLE #29

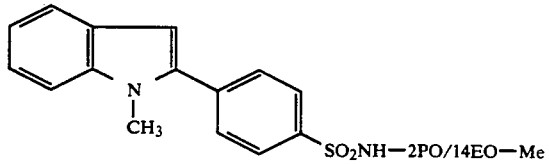

A mixture is prepared by adding 777 grams (1.05 mole) of primary amine with an amine equivalent weight of 1.35 meq/g) 129.9 grams of sodium carbonate in 2000 ml of water. The mixture is cooled to 10°-15° C. and 305 grams (1 mole) of 2-(chlorosulfonylphenyl)-1-methylindole are added to the mixture over one half hour. After the addition is complete, the mixture is warmed at 50° C. for an additional two hours to insure complete reaction. Afterwards, the mixture is cooled and the product is extracted into methylene chloride, further washed several times with water to a neutral pH, and dried over anhydrous magnesium sulfate. The dried solution is filtered and stripped under reduced pressure at 90° C. to yield a liquid intermediate.

EXAMPLE #29A

A 2000 milliliter beaker is charged with 111.1 grams (0.11 mole) of sulfonamide 2PO/14EO-Me intermediate from EXAMPLE #29, 200 grams of water, 200 grams of ice and 4 grams of urea. This mixture is cooled to below 0° C. The diazo solution (as prepared in EXAMPLE #3A) is added dropwise to the beaker over about 30 minutes, maintaining the temperature below 10° C. The resulting mixture is stirred for several hours and allowed to stand overnight, after which 260 grams of 50% sodium hydroxide are added to neutralize excess acid to a pH of about 7 keeping the temperature below 20° C. The bottom salt layer is removed and the product is dissolved in methylene chloride. The methylene chloride solution is washed four times with water and then dried over sodium sulfate. The methylene chloride solvent is then filtered and stripped to give a yellow-orange liquid.

EXAMPLE #30

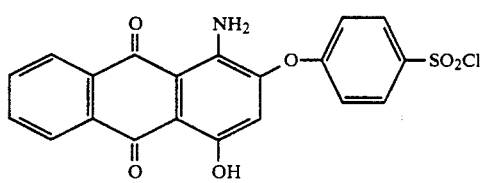

One hundred grams (0.32 mole) of 1-amino-2-phenoxy-4-hydroxyanthraquinone are dissolved at less than 25° C. in 423 grams of chlorosulfuric acid. The cooling bath is removed and the solution is allowed to warm to room temperature over two hours. The solution is further heated to 60° C. for about two hours after which the heat is removed and the solution is allowed to stir overnight at room temperature. The solution is then poured very gradually into a stirred mixture of water and ice. The red suspension of 1-amino-2-(4-chlorosulfonylphenoxy)-4-hydroxyanthraquinone is filtered and washed with ice water several times.

EXAMPLE #30A

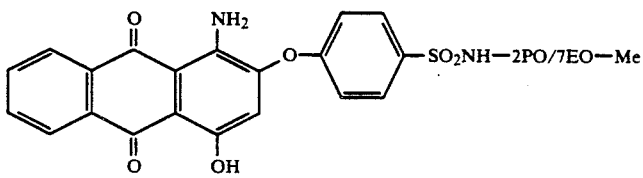

A mixture is prepared by adding 91.0 grams (0.19 mole) of a primary amine with an amine equivalent weight of 2.10 meq/g) to 44.5 grams sodium carbonate in 400 ml of THF and 200 ml of water. The mixture is cooled to 10°-15° C. and 0.18 mole of an aqueous wet cake of freshly prepared 1-amino-2-(4-chlorosulfonylphenoxy)-4-hydroxyanthraquinone from EXAMPLE #30 is added to the mixture. After the addition is complete, the mixture is warmed to 50° C. for an additional two hours to insure complete reaction. Three hundred milliliters of methylene chloride are added followed by 300 ml of water. The methylene chloride solution is separated from the salt water solution, further washed several times with water to neutral pH, and dried over anhydrous magnesium sulfate. The dried solution is filtered and stripped under reduced pressure at 90° C. to give a red product with maximum absorbance at 518 nm.

EXAMPLE #30B

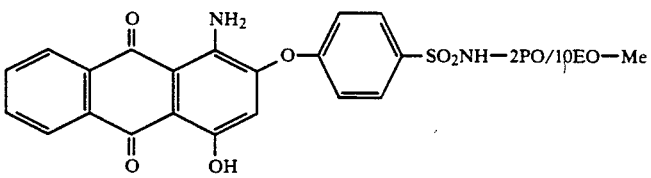

A mixture is prepared by adding 81.7 grams (0.14 mole) of a primary amine with an amine equivalent weight of 1.68 meq/g) to 33 grams sodium carbonate in 400 ml of THF and 200 ml of water. The mixture is cooled to 10°-15° C. and 0.13 mole of an aqueous wet cake of freshly prepared 1-amino-2-(4-chlorosulfonylphenoxy)-4-hydroxyanthraquinone from EXAMPLE #30 is added to the mixture. After the addition is complete, the mixture is warmed to 50° C. for an additional two hours to insure complete reaction. Three hundred milliliters of methylene chloride are added followed by 300 milliliters of water. The methylene chloride solution is separated from the salt water solution, further washed several times with water to neutral pH, and dried over anhydrous magnesium sulfate. The dried solution is filtered and stripped under reduced pressure at 90° C. to give a red product with maximum absorbance at 518 nm.

EXAMPLE #30C

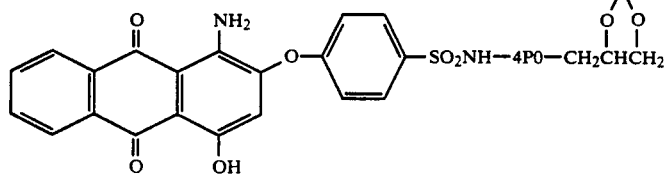

A mixture is prepared by adding 241.4 grams (0.28 mole) of a primary amine with an amine equivalent weight of 2.70 meq/g) to 64.7 grams sodium carbonate in 400 ml of THF and 200 ml of water. The mixture is cooled to 10°–15° C. and 0.26 mole of an aqueous wet cake of freshly prepared 1-amino-2-(4-chlorosulfonyl-phenoxy)-4-hydroxyanthraquinone from EXAMPLE #30 is added to the mixture. After the addition was complete, the mixture is warmed to 50° C. for an additional two hours to insure complete reaction. Three hundred milliliters of methylene chloride are added followed by 300 milliliters of water. The methylene chloride solution is separated from the salt water solution, further washed several times with water to neutral pH, and dried over anhydrous magnesium sulfate. The dried solution is filtered and stripped under reduced pressure at 90° C. to give a red product with maximum absorbance at 518 nm.

EXAMPLE #30D

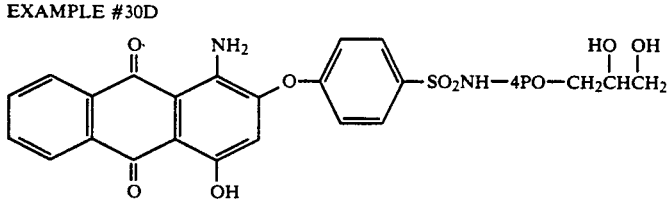

Eighty nine grams (0.12 mole) of the acetal prepared in EXAMPLE #30C are added along with 200 ml of water to a three necked 250 ml flask equipped with overhead stirrer, heating mantle, and Dean-Stark trap. The mixture is heated to 80° C. and 10 grams of 70% sulfuric acid are added. This reaction mixture is maintained at 80° C. until no more acetone can be detected overhead in the trap. The mixture is then cooled and the product is extracted into methylene chloride. The methylene chloride solution is separated, washed several times with water to neutral pH, and dried over anhydrous magnesium sulfate. The dried methylene chloride solution is filtered and stripped under reduced pressure at 90° C. to give a red product with maximum absorbance at 518 nm and containing a hydroxyl band in the IR spectrum.

EXAMPLE #30E

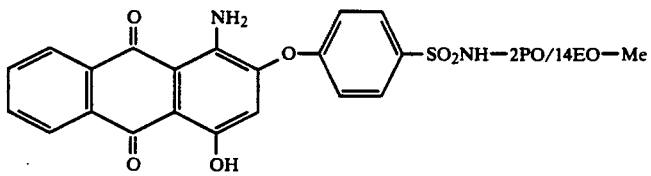

A mixture is prepared by adding 80.7 grams (0.11 mole) of a primary amine with an amine equivalent weight of 1.35 meq/g) to 25.7 grams sodium carbonate in 500 ml of water and 200 ml of THF. The mixture is cooled to 10°–15° C. and 0.10 mole of an aqueous wet cake of freshly prepared 1-amino-2-(4-chlorosulfonyl-phenoxy)-4-hydroxyanthraquinone from EXAMPLE #30 is added to the mixture. After the addition is complete, the mixture is warmed to 50° C. for an additional two hours to insure complete reaction. Three hundred milliliters of methylene chloride are added followed by 300 milliliters of water. The methylene chloride solution is separated from the salt water solution, further washed several times with water to neutral pH, and dried over anhydrous magnesium sulfate. The dried solution is filtered and stripped under reduced pressure at 90° C. to give a red product with maximum absorbance at 518 nm.

EXAMPLE #31

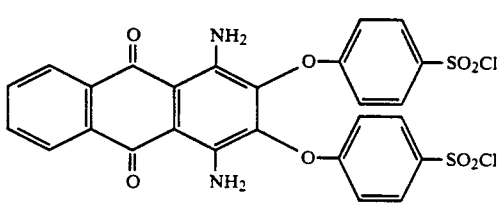

One hundred thirty-five grams (0.32 mole) of 1,4-diamino-2,3-diphenoxyanthraquinone are dissolved at less than 25° C. in 890 grams of chlorosulfuric acid. The cooling bath is removed and the solution is allowed to warm to room temperature over two hours. The solution is further heated to 60° C. for about two hours after which the heat is removed and the solution is allowed to stir overnight at room temperature. The solution is then poured very gradually into a stirred mixture of water and ice. The violet suspension of 1,4-diamino-2,3-(di-4-chlorosulfonylphenoxy) anthraquinone is filtered and washed with ice water several times.

EXAMPLE #31A

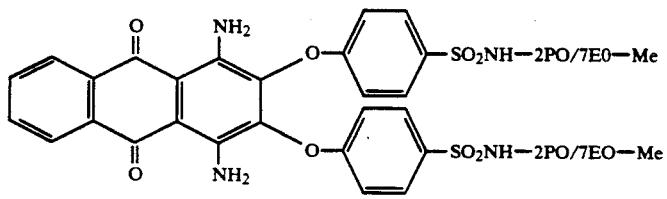

A mixture is prepared by adding 91.0 grams (0.19 mole) of a primary amine with an amine equivalent weight of 2.10 meq/g) to 44.5 grams sodium carbonate in 400 ml of THF and 200 ml of water. The mixture is cooled to 10°-15° C. and 0.095 mole of an aqueous wet cake of freshly prepared 1,4-diamino-2,3-(di-1'-chlorosulfonyl)phenoxyanthraquinone from EXAMPLE #31 is added to the mixture. After the addition was complete, the mixture is warmed to 50° C. for an additional two hours to insure complete reaction. Three hundred milliliters of methylene chloride are added followed by 300 ml of water. The methylene chloride solution is separated from the salt water solution, further washed several times with water to neutral pH, and dried over anhydrous magnesium sulfate. The dried solution is filtered and stripped under reduced pressure at 90° C. to give a violet liquid with maximum absorbance at 547 nm.

EXAMPLE #32

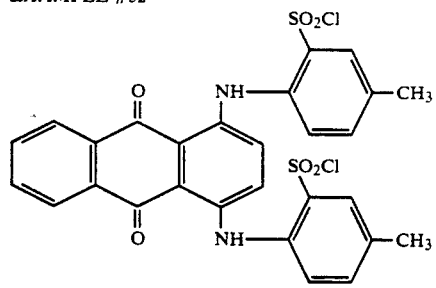

One hundred thirty-five grams (0.32 mole) of 1,4-di-p-tolylanthraquinone are dissolved at less than 25° C. in 890 grams of chlorosulfuric acid. The cooling bath is removed and the solution is allowed to warm to room temperature over two hours. The solution is further heated to 60° C. for about two hours after which the heat is removed and the solution is allowed to stir overnight at room temperature. The solution is then poured very gradually into a stirred mixture of water and ice. The blue suspension of 1,4-di-(-chlorosulfonyl-4-methylaniline) anthraquinone is filtered and washed with ice water several times.

EXAMPLE #32A

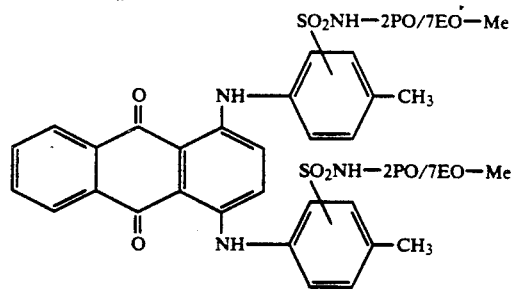

A mixture is prepared by adding 91.0 grams (0.19 mole) of a primary amine with an amine equivalent weight of 2.10 meq/g) to 44.5 grams sodium carbonate in 400 ml of THF and 200 ml of water. The mixture is cooled to 10°-15° C. and 0.095 mole of an aqueous wet cake of freshly prepared 1,4-di-(-chlorosulfonyl-4-methylaniline)anthraquinone from EXAMPLE #32 is added to the mixture. After the addition is complete, the mixture is warmed to 50° C. for an additional two hours to insure complete reaction. Three hundred milliliters of methylene chloride are added followed by 300 ml of water. The methylene chloride solution is separated from the salt water solution, further washed several times with water to neutral pH, and dried over anhydrous magnesium sulfate. The dried solution is filtered and stripped under reduced pressure at 90° C. to give a bluish green liquid with maximum absorbance at 660 nm.

EXAMPLE #33

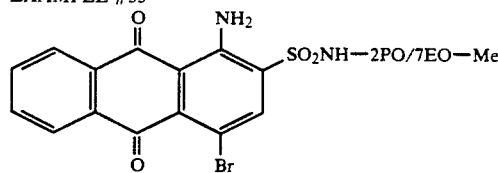

A mixture is prepared by adding 91.0 grams (0.19 mole) of a primary amine with an amine equivalent weight of 2.10 meq/g) to 44.5 grams sodium carbonate in 400 ml of THF and 200 ml of water. The mixture is cooled to 10°-15° C. and 0.18 mole of an aqueous wet cake of freshly prepared 1-amino-4-bromoanthraquinone-2-sulfonyl chloride is added to the mixture. After the addition is complete, the mixture is warmed to 50° C. for an additional two hours to insure complete reaction. Three hundred milliliters of methylene chloride are added followed by 300 ml of water. The methylene chloride solution is separated from the salt water solution, further washed several times with water to neutral pH, and dried over anhydrous magnesium sulfate. The dried solution is filtered and stripped under reduced pressure at 90° C. to give a orangish product with maximum absorbance at 482 nm.

EXAMPLE #33A

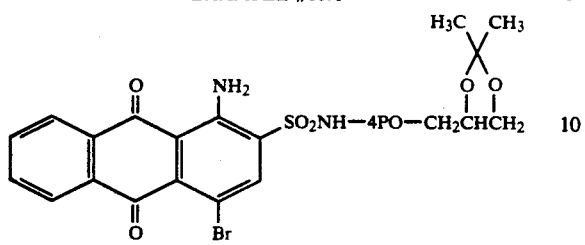

A mixture is prepared by adding 241.4 grams (0.28 mole) of a primary amine with an amine equivalent weight of 2.70 meq/g) to 64.7 grams sodium carbonate in 400 ml of THF and 200 ml of water. The mixture is cooled to 10°-15° C. and 0.26 mole of an aqueous wet cake of freshly prepared 1-amino-4-bromoanthraquinone-2-sulfonyl chloride are added to the mixture. After the addition is complete, the mixture is warmed to 50° C. for an additional two hours to insure complete reaction. Three hundred milliliters of methylene chloride are added followed by 300 milliliters of water. The methylene chloride solution is separated from the salt water solution, further washed several times with water to neutral pH, and dried over anhydrous magnesium sulfate. The dried solution is filtered and stripped under reduced pressure at 90° C. to give a orangish product with maximum absorbance at 482 nm.

EXAMPLE #33B

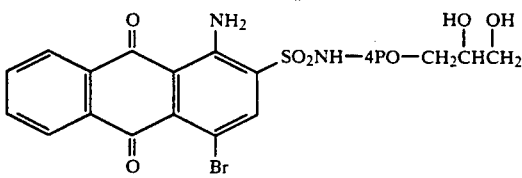

Eighty eight grams (0.12 mole) of the acetal prepared in EXAMPLE #33A are added along with 200 ml of water to a three necked 500 ml flask equipped with overhead stirrer, heating mantle, and Dean-Stark trap. The mixture is heated to 80° C. and 10 grams of 70% sulfuric acid are added. This reaction mixture is maintained at 80° C. until no more acetone can be detected overhead in the trap. The mixture is then cooled and the product is extracted into methylene chloride. The methylene chloride solution is separated, washed several times with water to neutral pH, and dried over anhydrous magnesium sulfate. The dried methylene chloride solution is filtered and stripped under reduced pressure at 90° C. to give a orangish product with maximum absorbance at 482 nm and containing a hydroxyl band in the IR spectrum.

EXAMPLE #34

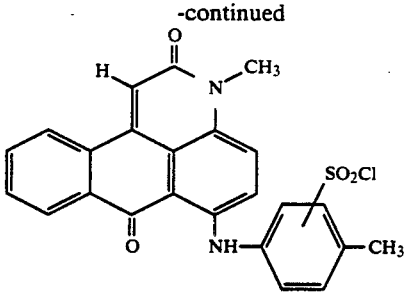

One hundred seventeen grams (0.32 mole) of 6-(p-toluidine)-anthrapyridone are dissolved at less than 25° C. in 890 grams of chlorosulfuric acid. The cooling bath is removed and the solution is allowed to warm to room temperature over two hours. The solution is further heated to 60° C. for about two hours after which the heat is removed and the solution is allowed to stir overnight at room temperature. The solution is then poured very gradually into a stirred mixture of water and ice. The red suspension of 6-(-chlorosulfonyl-4-methylaniline)-anthrapyridone is filtered and washed with ice water several times.

EXAMPLE #34A

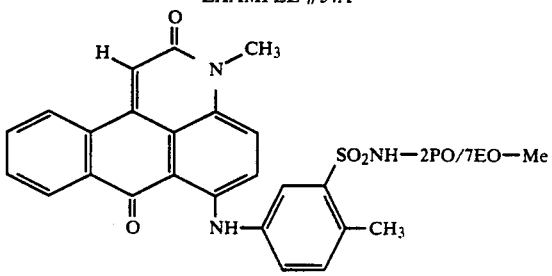

A mixture is prepared by adding 91.0 grams (0.19 mole) of a primary amine with an amine equivalent weight of 2.10 meq/g) to 44.5 grams sodium carbonate in 400 ml of THF and 200 ml of water. The mixture is cooled to 10°-15° C. and 0.18 mole of an aqueous wet cake of freshly prepared 6-(-chlorosulfonyl-4-methylaniline)-anthrapyridone from EXAMPLE #34 is added to the mixture. After the addition is complete, the mixture is warmed to 50° C. for an additional two hours to insure complete reaction. Three hundred milliliters of methylene chloride are added followed by 300 ml of water. The methylene chloride solution is separated from the salt water solution, further washed several times with water to neutral pH, and dried over anhydrous magnesium sulfate. The dried solution is filtered and stripped under reduced pressure at 90° C. to give a red product with maximum absorbance at 523 nm.

We claim:

1. A process for coloring a thermoplastic resin which comprises the step of incorporating into a thermoplastic resin selected from polyolefin, polystyrene, polyvinyl chloride, polyvinylidene chloride, ABS, polyamide, polyester, styrene acrylonitrile, polycarbonate, cellulose acetate, cellulose acetate butyrate, cellulose acetate propionate and acrylic resins, while said resin is in a molten state, from 0.001 to 3 wt. % of a colorant having the formula:

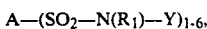

$A—(SO_2—N(R_1)—Y)_{1-6}$, wherein A is metal-free organic chromophore group;
wherein $R_1$ is hydrogen, $C_1$–$C_{12}$ alkyl or cycloalkyl, aryl or Y; and Y is a poly(oxyalkylene) moiety comprising 4 to 200 epoxide reactant residues of 2–4 carbons each;

where Y is terminated with a group selected from alkyl, cycloalkyl and acyl of a carboxylic acid containing up to 12 carbon atoms, phenyl and groups having the formula:

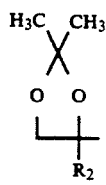

wherein $R_2$ is H, methyl or ethyl.

2. A process according to claim 1 wherein said thermoplastic resin is selected from polyolefin, polystyrene, polyvinyl chloride, polyvinylidene chloride, ABS, polyamide and polyester resins.

3. A process according to claim 2 wherein $R_1$ is selected from hydrogen or Y.

4. A process according to claim 3 wherein Y comprises greater than 12 of said epoxide reactant residues.

5. A process according to claim 2 wherein said organic chromophore group is selected from azo, triphenylmethane, methine, anthraquinone and anthrapyridone chromophores.

6. A process according to claim 5 wherein $R_1$ is selected from hydrogen or Y.

7. A process according to claim 6 wherein Y comprises 16 or greater of said epoxide reactant residues.

8. A process according to claim 6 wherein said thermoplastic resin is a polyolefin resin.

9. A colored thermoplastic resin composition which comprises a thermoplastic resin selected from polyolefin, polystyrene, polyvinyl chloride, polyvinylidene chloride, ABS, polyamide, polyester, styrene acrylonitrile, polycarbonate, cellulose acetate, cellulose acetate butyrate, cellulose acetate propionate and acrylic resins, and from 0.001 to 3 wt. % of a colorant incorporated and distributed throughout the mass of said thermoplastic resin whereby said colorant is essentially non-extractable from said resin, wherein said colorant has the formula:

$$A-(SO_2-N(R_1)-Y)_{1-6},$$

wherein A is metal-free organic chromophore group;
wherein $R_1$ is hydrogen, $C_1$–$C_{12}$ alkyl or cycloalkyl, aryl or Y; and Y is a poly(oxyalkylene) moiety comprising 4 to 200 epoxide reactant residues of 2–4 carbons each where Y is terminated with a group selected from alkyl, cycloalkyl and acyl of a carboxylic acid containing up to 12 carbon atoms, phenyl and groups having the formula:

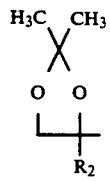

wherein $R_2$ is H, methyl or ethyl.

10. The colored resin composition of claim 9 wherein said thermoplastic resin is selected from polyolefin, polystyrene, polyvinyl chloride, polyvinylidene chloride, ABS, polyamide and polyester resins.

11. The colored resin composition of claim 10 wherein $R_1$ is selected from hydrogen or Y.

12. The colored resin composition of claim 11 wherein Y comprises greater than 12 of said epoxide reactant residues.

13. The colored resin composition of claim 10 wherein said organic chromophore group is selected from azo, triphenylmethane, methine, anthraquinone and anthrapyridone chromophores.

14. The colored resin composition of claim 13 wherein $R_1$ is selected from hydrogen or Y.

15. The colored resin composition of claim 14 wherein Y comprises 16 or greater of said epoxide reactant residues.

16. The colored resin composition of claim 14 wherein said thermoplastic resin is a polyolefin resin.

17. The colored resin composition of claim 12 wherein said colorant is added to said thermoplastic resin while said thermoplastic resin is in a molten state.

18. The colored thermoplastic resin composition of claim 16 wherein said colorant is added to said thermoplastic resin while said thermoplastic resin is in a molten state.

* * * * *